(12) United States Patent
Querfurth

(10) Patent No.: US 9,618,511 B2
(45) Date of Patent: *Apr. 11, 2017

(54) METHODS AND COMPOSITIONS FOR TREATING ALZHEIMER'S DISEASE

(71) Applicant: Eleanore Bennett Charitable Trust #2, Waltham, MA (US)

(72) Inventor: Henry W. Querfurth, Wellesley, MA (US)

(73) Assignee: Eleanore Bennett Charitable Trust #2, Waltham, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/609,845

(22) Filed: Jan. 30, 2015

(65) Prior Publication Data

US 2015/0247857 A1  Sep. 3, 2015

Related U.S. Application Data

(63) Continuation of application No. 12/997,154, filed as application No. PCT/US2009/003519 on Jun. 10, 2009, now Pat. No. 8,969,023.

(60) Provisional application No. 61/060,469, filed on Jun. 10, 2008.

(51) Int. Cl.
| | | |
|---|---|---|
| G01N 33/53 | (2006.01) | |
| G01N 33/542 | (2006.01) | |
| G01N 33/573 | (2006.01) | |
| C12Q 1/48 | (2006.01) | |

(52) U.S. Cl.
CPC .......... *G01N 33/573* (2013.01); *C12Q 1/485* (2013.01); *G01N 2333/4709* (2013.01); *G01N 2333/912* (2013.01); *G01N 2333/91215* (2013.01); *G01N 2440/14* (2013.01); *G01N 2500/02* (2013.01); *G01N 2500/04* (2013.01); *G01N 2500/10* (2013.01); *G01N 2800/2821* (2013.01)

(58) Field of Classification Search
None
See application file for complete search history.

(56) References Cited

U.S. PATENT DOCUMENTS

| 8,969,023 B2 * | 3/2015 | Querfurth | ............... C12Q 1/485 435/7.1 |
|---|---|---|---|
| 2011/0165598 A1 | 7/2011 | Querfurth | |

FOREIGN PATENT DOCUMENTS

| EP | 1 486 488 A1 | 12/2004 |
|---|---|---|
| EP | 1 837 034 A1 | 6/2006 |
| EP | 2 177 510 A1 | 4/2010 |
| EP | 2 182 058 A1 | 5/2010 |
| WO | WO 2008/019890 A2 | 2/2008 |
| WO | WO 2010/043711 A1 | 4/2010 |
| WO | WO 2010/043719 A1 | 4/2010 |

OTHER PUBLICATIONS

Invitation to Pay Additional Fees mailed Nov. 2, 2009 for PCT/US2009/003519.
International Preliminary Report on Patentability mailed Dec. 23, 2010 for PCT/US2009/003519.
Abbott et al., Abeta(1-42) modulation of Akt phosphorylation via alpha7 nAChR and NMDA receptors. Neurobiol Aging. Jul. 2008;29(7):992-1001. Epub Feb. 9, 2007.
Abbott et al., The insulin receptor tyrosine kinase substrate p58/53 and the insulin receptor are components of CNS synapses. J Neurosci. Sep. 1, 1999;19(17):7300-8.
Biondi et al., High resolution crystal structure of the human PDK1 catalytic domain defines the regulatory phosphopeptide docking site. EMBO J. Aug. 15, 2002;21(16):4219-28.
Casamayor et al., Phosphorylation of Ser-241 is essential for the activity of 3-phosphoinositide-dependent protein kinase-1: identification of five sites of phosphorylation in vivo. Biochem J. Sep. 1, 1999;342 ( Pt 2):287-92.
Chen et al., Insulin stimulates increased catalytic activity of phosphoinositide-dependent kinase-1 by a phosphorylation-dependent mechanism. Biochemistry. Oct. 2, 2001;40(39):11851-9.
Cheng et al., Insulin-like growth factor 1 regulates developing brain glucose metabolism. Proc Natl Acad Sci U S A. Aug. 29, 2000;97(18):10236-41.
Craft et al., Intranasal insulin therapy for Alzheimer disease and amnestic mild cognitive impairment: a pilot clinical trial. Arch Neurol. Jan. 2012;69(1):29-38. doi: 10.1001/archneurol.2011.233. Epub Sep. 12, 2011.
Datta et al., Akt phosphorylation of BAD couples survival signals to the cell-intrinsic death machinery. Cell. Oct. 17, 1997;91(2):231-41.
De Felice et al., Protection of synapses against Alzheimer's-linked toxins: insulin signaling prevents the pathogenic binding of Abeta oligomers. Proc Natl Acad Sci U S A. Feb. 10, 2009;106(6):1971-6. doi:10.1073/pnas.0809158106. Epub Feb. 2, 2009. Erratum in: Proc Natl Acad Sci U S A.May 5, 2009;106(18):7678.
De La Monte et al., Therapeutic rescue of neurodegeneration in experimental type 3 diabetes: relevance to Alzheimer's disease. J Alzheimers Dis. Sep. 2006;10(1):89-109.
Gao et al., PHLPP: a phosphatase that directly dephosphorylates Akt, promotes apoptosis, and suppresses tumor growth. Mol Cell. Apr. 1, 2005;18(1):13-24.
Gasparini et al., Does insulin dysfunction play a role in Alzheimer's disease? Trends Pharmacol Sci. Jun. 2002;23(6):288-93.
Gouras et al., Intraneuronal Abeta accumulation and origin of plaques in Alzheimer's disease. Neurobiol Aging. Oct. 2005;26(9):1235-44.
Griffin et al., Activation of Akt/PKB, increased phosphorylation of Akt substrates and loss and altered distribution of Akt and PTEN are features of Alzheimer's disease pathology. J Neurochem. Apr. 2005;93(1):105-17.

(Continued)

*Primary Examiner* — Olga N Chernyshev
(74) *Attorney, Agent, or Firm* — Wolf, Greenfield & Sacks, P.C.

(57) ABSTRACT

Aspects of the invention relate to methods and compositions for treating Alzheimer's disease (AD). In some embodiments, the invention provides methods for screening and identifying compounds that selectively inhibit the targeting of the insulin-Akt signaling pathway by Aβ oligomers.

6 Claims, 32 Drawing Sheets

(56) References Cited

OTHER PUBLICATIONS

Horwood et al., Signalling mechanisms mediated by the phosphoinositide 3-kinase/Akt cascade in synaptic plasticity and memory in the rat. Eur J Neurosci. Jun. 2006;23(12):3375-84.

Hou et al., Activation of the phosphoinositide 3-kinase-Akt-mammalian target of rapamycin signaling pathway is required for metabotropic glutamate receptor-dependent long-term depression. J Neurosci. Jul. 14, 2004;24(28):6352-61.

Hresko et al., mTOR.RICTOR is the Ser473 kinase for Akt/protein kinase B in 3T3-L1 adipocytes. J Biol Chem. Dec. 9, 2005;280(49):40406-16. Epub Oct. 11, 2005.

Jimenez et al., Age-dependent accumulation of soluble amyloid beta (Abeta) oligomers reverses the neuroprotective effect of soluble amyloid precursor protein-alpha (sAPP(alpha)) by modulating phosphatidylinositol 3-kinase (PI3K)/Akt-GSK-3beta pathway in Alzheimer mouse model. J Biol Chem. May 27, 2011;286(21):18414-25. doi: 10.1074/jbc.M110.209718. Epub Apr. 1, 2011.

Jo et al., Aβ(1-42) inhibition of LTP is mediated by a signaling pathway involving caspase-3, Akt1 and GSK-3β. Nat Neurosci. May 2011;14(5):545-7. doi: 10.1038/nn.2785. Epub Mar. 27, 2011.

Kern et al., Improving influence of insulin on cognitive functions in humans. Neuroendocrinology. Oct. 2001;74(4):270-80.

Kobayashi et al., Activation of serum- and glucocorticoid-regulated protein kinase by agonists that activate phosphatidylinositide 3-kinase is mediated by 3-phosphoinositide-dependent protein kinase-1 (PDK1) and PDK2. Biochem J. Apr. 15, 1999;339 ( Pt 2):319-28.

Kubo et al., 6-Ethyl-N,N'-bis(3-hydroxyphenyl)[1,3,5]triazine-2,4-diamine (RS-0466) enhances the protective effect of brain-derived neurotrophic factor on amyloid beta-induced cytotoxicity in cortical neurones. Pharmacol Toxicol. Dec. 2003;93(6):264-8.

Lee et al., Insulin promotes dendritic spine and synapse formation by the PI3K/Akt/mTOR and Rac1 signaling pathways. Neuropharmacology. Sep. 2011;61(4):867-79. doi: 10.1016/j.neuropharm.2011.06.003. Epub Jun. 12, 2011.

Lee et al., Insulin rescues amyloid beta-induced impairment of hippocampal long-term potentiation. Neurobiol Aging. Mar. 2009;30(3):377-87. Epub Aug. 10, 2007.

Lee et al., The insulin/Akt signaling pathway is targeted by intracellular beta-amyloid. Mol Biol Cell. Mar. 2009;20(5):1533-44. doi: 10.1091/mbc.E08-07-0777. Epub Jan. 14, 2009.

Lu et al., Development of a fluorescence polarization bead-based coupled assay to target different activity/conformation states of a protein kinase. J Biomol Screen. Jun. 2004;9(4):309-21.

Luo et al., Akt as a mediator of cell death. Proc Natl Acad Sci U S A. Sep. 30, 2003;100(20):11712-7. Epub Sep. 22, 2003.

Magrané et al., Intraneuronal beta-amyloid expression downregulates the Akt survival pathway and blunts the stress response. J Neurosci. Nov. 23, 2005;25(47):10960-9.

Man et al., Activation of PI3-kinase is required for AMPA receptor insertion during LTP of mEPSCs in cultured hippocampal neurons. Neuron. May 22, 2003;38(4):611-24.

Martín et al., Effect of the Alzheimer amyloid fragment Abeta(25-35) on Akt/PKB kinase and survival of PC12 cells. J Neurochem. Sep. 2001;78(5):1000-8.

McClean et al., The diabetes drug liraglutide prevents degenerative processes in a mouse model of Alzheimer's disease. J Neurosci. Apr. 27, 2011;31(17):6587-94. doi:10.1523/JNEUROSCI.0529-11.2011.

Messier et al., The role of insulin, insulin growth factor, and insulin-degrading enzyme in brain aging and Alzheimer's disease. Neural Plast. 2005;12(4):311-28.

Nakagami et al., A novel beta-sheet breaker, RS-0406, reverses amyloid beta-induced cytotoxicity and impairment of long-term potentiation in vitro. Br J Pharmacol. Nov. 2002;137(5):676-82.

Nakagami et al., A novel compound RS-0466 reverses beta-amyloid-induced cytotoxicity through the Akt signaling pathway in vitro. Eur J Pharmacol. Dec. 13, 2002;457(1):11-7.

Nakagami, Inhibitors beta-amyloid-induced toxicity by modulating the Akt signaling pathway. Drug News Perspect. Dec. 2004;17(10):655-60.

Nishimura et al., RS-4252 inhibits amyloid beta-induced cytotoxicity in HeLa cells. Pharmacol Toxicol. Jul. 2003;93(1):29-32.

Nisticó et al., Insulin receptor β-subunit haploinsufficiency impairs hippocampal late-phase LTP and recognition memory. Neuromolecular Med. Dec. 2012;14(4):262-9. doi: 10.1007/s12017-012-8184-z. Epub Jun. 3, 2012.

Oakley et al., Intraneuronal beta-amyloid aggregates, neurodegeneration, and neuron loss in transgenic mice with fivefamilial Alzheimer's disease mutations: potential factors in amyloid plaque formation. J Neurosci. Oct. 4, 2006;26(40):10129-40.

Opazo et al., Phosphatidylinositol 3-kinase regulates the induction of long-term potentiation through extracellular signal-related kinase-independent mechanisms. J Neurosci. May 1, 2003;23(9):3679-88.

Pei et al., Role of protein kinase B in Alzheimer's neurofibrillary pathology. Acta Neuropathol. Apr. 2003;105(4):381-92. Epub Dec. 18, 2002.

Querfurth et al., Beta-amyloid peptide expression is sufficient for myotube death: implications for human inclusion body myopathy. Mol Cell Neurosci. May 2001;17(5):793-810.

Rickle et al., Akt activity in Alzheimer's disease and other neurodegenerative disorders. Neuroreport. Apr. 29, 2004;15(6):955-9.

Sanna et al., Phosphatidylinositol 3-kinase is required for the expression but not for the induction or the maintenance of long-term potentiation in the hippocampal CA1 region. J Neurosci. May 1, 2002;22(9):3359-65.

Sarbassov et al., Phosphorylation and regulation of Akt/PKB by the rictor-mTOR complex. Science. Feb. 18, 2005;307(5712):1098-101.

Schubert et al., Role for neuronal insulin resistance in neurodegenerative diseases. Proc Natl Acad Sci U S A. Mar. 2, 2004;101(9):3100-5. Epub Feb. 23, 2004.

Skeberdis et al., Insulin promotes rapid delivery of N-methyl-D-aspartate receptors to the cell surface by exocytosis. Proc Natl Acad Sci U S A. Mar. 13, 2001;98(6):3561-6.

Steen et al., Impaired insulin and insulin-like growth factor expression and signaling mechanisms in Alzheimer's disease—is this type 3 diabetes? J Alzheimers Dis. Feb. 2005;7(1):63-80.

Sui et al., Role of the phosphoinositide 3-kinase-Akt-mammalian target of the rapamycin signaling pathway in long-term potentiation and trace fear conditioning memory in rat medial prefrontal cortex. Learn Mem. Oct. 2, 2008;15(10):762-76. doi: 10.1101/lm.1067808. Print Oct. 2008.

Tessier et al., Serum and glucocorticoid-regulated protein kinases: variations on a theme. J Cell Biochem. Aug. 15, 2006;98(6):1391-407.

Toker et al., Akt/protein kinase B is regulated by autophosphorylation at the hypothetical PDK-2 site. J Biol Chem. Mar. 24, 2000;275(12):8271-4.

Tong et al., Beta-amyloid peptide at sublethal concentrations downregulates brain-derived neurotrophic factor functions in cultured cortical neurons. J Neurosci. Jul. 28, 2004;24(30):6799-809.

Townsend et al., Soluble Abeta inhibits specific signal transduction cascades common to the insulin receptor pathway. J Biol Chem. Nov. 16, 2007;282(46):33305-12. Epub Sep. 13, 2007.

Townsend et al., Effects of secreted oligomers of amyloid beta-protein on hippocampal synaptic plasticity: a potent role for trimers. J Physiol. Apr. 15, 2006;572(Pt 2):477-92. Epub Feb. 9, 2006.

Ugi et al., Protein phosphatase 2A negatively regulates insulin's metabolic signaling pathway by inhibiting Akt (protein kinase B) activity in 3T3-L1 adipocytes. Mol Cell Biol. Oct. 2004;24(19):8778-89.

Van Der Heide et al., Insulin modulates hippocampal activity-dependent synaptic plasticity in a N-methyl-d-aspartate receptor and phosphatidyl-inositol-3-kinase-dependent manner. J Neurochem. Aug. 2005;94(4):1158-66.

Wang et al., Metformin activates an atypical PKC-CBP pathway to promote neurogenesis and enhance spatial memory formation. Cell Stem Cell. Jul. 6, 2012;11(1):23-35. doi: 10.1016/j.stem.2012.03.016.

(56) References Cited

OTHER PUBLICATIONS

Wang et al., Control of synaptic strength, a novel function of Akt. Neuron. Jun. 9, 2003;38(6):915-28.

Watson et al., Preserved cognition in patients with early Alzheimer disease and amnestic mild cognitive impairment during treatment with rosiglitazone: a preliminary study. Am J Geriatr Psychiatry. Nov. 2005;13(11):950-8.

Wei et al., Signaling events in amyloid beta-peptide-induced neuronal death and insulin-like growth factor I protection. J Biol Chem. May 17, 2002;277(20):17649-56. Epub Mar. 6, 2002.

Xie et al., Alzheimer's beta-amyloid peptides compete for insulin binding to the insulin receptor. J Neurosci. May 15, 2002;22(10):RC221. Epub May 10, 2002.

Zheng et al., Insulin-like growth factor-1-induced phosphorylation of the forkhead family transcription factor FKHRL1 is mediated by Akt kinase in PC12 cells. J Biol Chem. Dec. 15, 2000;275(50):39152-8.

* cited by examiner

RFU: relative fluorescence units

Figure 3B. TruLight™ assay for PDK dependent–Akt activation. Immunoprecipitated PDK1 and Akt were incubated with and without synthetic Ab in the presence ATP, kinase buffer, lipid and peptide substrate conjugated to a quencher moiety.

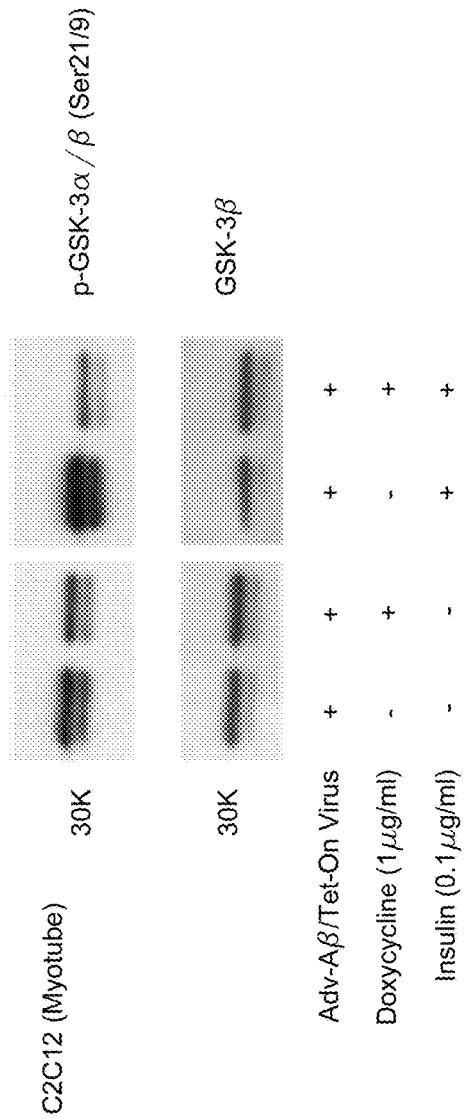

FIG. 3D

Testing the expression of intracellular Aβ against Akt activation in cell lysates by *in vitro* Akt kinase assay. Total Akt was immunoprecipitated (IP) from C2C12 myotubes that were infected with Adv-Aβ/Tet-On virus and then induced or not with doxycycline to express Aβ. One group was treated with insulin to enhance Akt activation. Akt was IP and tested in vitro for its ability to phosphorylate the GSK-3β synthetic substrate. Anti-total and pGSK antibodies peptide are from Cell Signaling. Aβ levels follow doxycycline induction (not shown), Akt activation by insulin was followed using anti-pS473 Akt (not shown).

FIG. 5C (con't)
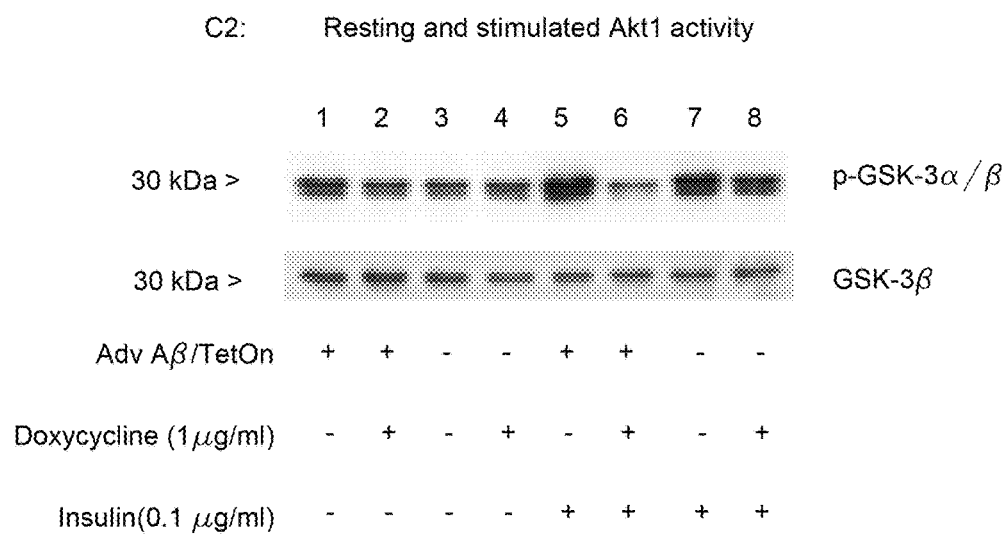
FIG. 5D
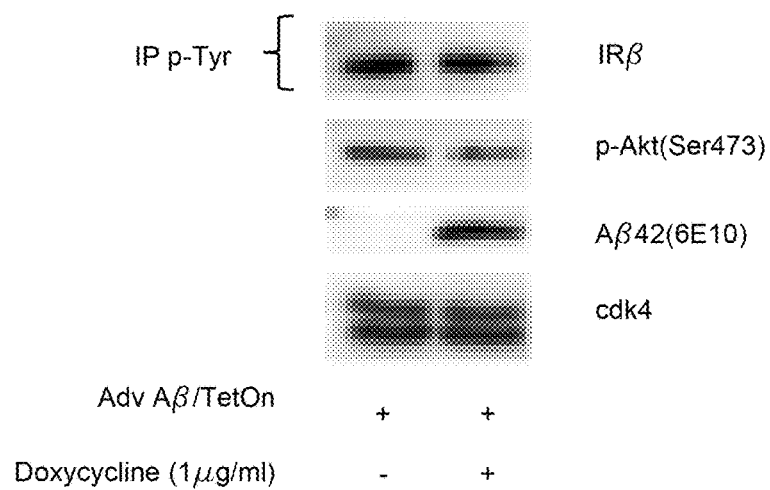

METHODS AND COMPOSITIONS FOR TREATING ALZHEIMER'S DISEASE

RELATED APPLICATIONS

This continuation application claims the benefit under 35 U.S.C. §120 of U.S. application Ser. No. 12/997,154, entitled "METHODS AND COMPOSITIONS FOR TREATING ALZHEIMER'S DISEASE" filed Mar. 21, 2011, which is a national stage filing under U.S.C. §371 of PCT Application PCT/US2009/003519, entitled "METHODS AND COMPOSITIONS FOR TREATING ALZHEIMER'S DISEASE" filed on Jun. 10, 2009, which claims priority under 35 U.S.C. §119(e) to U.S. Provisional Application Ser. No. 61/060,469, entitled "METHODS AND COMPOSITIONS FOR TREATING ALZHEIMER'S DISEASE" filed on Jun. 10, 2008, which are herein incorporated by reference in their entirety.

GOVERNMENT INTEREST

This work was funded in part by the NIH grant (NINDS 41373). The government has certain rights in this invention.

FIELD OF THE INVENTION

The invention relates to methods and compositions for treating Alzheimer's disease (AD).

BACKGROUND OF THE INVENTION

Intraneuronal β-amyloid (Aβ) factors significantly in the early pathogenesis of Alzheimer's disease (AD), (Gouras, G. K., Almeida, C. G., and Takahashi, R. H., 2005, Intraneuronal Abeta accumulation and origin of plaques in Alzheimer's disease, *Neurobiol Aging* 26:1235-1244; Gouras, G. K., Tsai, J., Naslund, J., Vincent, B., Edgar, M., Checler, F., Greenfield, J. P., Haroutunian, V., Buxbaum, J. D., Xu, H., et al., 2000, Intraneuronal Abeta42 accumulation in human brain, *Am J Pathol* 156:15-20; Hartman, T., 2005, Cholesterol and Alzheimer's disease: statins, cholesterol depletion in APP processing and Abeta generation, *Subcell Biochem* 38:365-380; and LaFerla, F. M., Green, K. N., and Oddo, S., 2007, Intracellular amyloid-beta in Alzheimer's disease, *Nat Rev Neurosci* 8:499-509) which historically is more recognized for the occurrence of extracellular plaques comprised of Aβ42, ubiquitin and numerous chaperones. Inclusion body myositis (IBM), another disorder associated with intracellular Aβ deposits, is a major cause of skeletal muscle inflammation and degeneration in the elderly. Cytosolic Aβ has been shown to induce programmed cell death (apoptosis) in a number of experimental and transgenic models involving several cell types (LaFerla, F. M., Green, K. N., and Oddo, S., 2007, Intracellular amyloid-beta in Alzheimer's disease, *Nat Rev Neurosci* 8:499-509; Magrane, J., Rosen, K. M., Smith, R. C., Walsh, K., Gouras, G. K., and Querfurth, H. W., 2005, Intraneuronal beta-amyloid expression downregulates the Akt survival pathway and blunts the stress response, *J Neurosci* 25:10960-10969; Oakley, H., Cole, S. L., Logan, S., Maus, E., Shao, P., Craft, J., Guillozet-Bongaarts, A., Ohno, M., Disterhoft, J., Van Eldik, L., et al., 2006, Intraneuronal beta-amyloid aggregates, neurodegeneration, and neuron loss in transgenic mice with five familial Alzheimer's disease mutations: potential factors in amyloid plaque formation, *J Neurosci* 26:10129-10140; Querfurth, H. W., Suhara, T., Rosen, K. M., McPhie, D. L., Fujio, Y., Tejada, G., Neve, R. L., Adelman, L. S., and Walsh, K., 2001, Beta-amyloid peptide expression is sufficient for myotube death: implications for human inclusion body myopathy, *Mol Cell Neurosci* 17:793-810; Link, C. D., 1995, Expression of human beta-amyloid peptide in transgenic Caenorhabditis legans, *Proc Natl Acad Sci U S A* 92:9368-9372; and Zhang, Y., McLaughlin, R., Goodyer, C., and LeBlanc, A., 2002, Selective cytotoxicity of intracellular amyloid beta peptide1-42 through p53 and Bax in cultured primary human neurons, *J Cell Biol* 156:519-529). The serine-threonine kinase Akt maintains post-mitotic cell viability through phosphorylation of pro-apoptotic mediators, thereby inactivating them. These factors include the transcription factor forkhead (FOXO), the tau kinase GSK-3β, and the Bcl2 antagonist BAD proteins (Brunet, A., Bonni, A., Zigmond, M. J., Lin, M. Z., Juo, P., Hu, L. S., Anderson, M. J., Arden, K. C., Blenis, J., and Greenberg, M. E., 1999, Akt promotes cell survival by phosphorylating and inhibiting a Forkhead transcription factor, *Cell* 96:857-868; Cross, D. A., Alessi, D. R., Cohen, P., Andjelkovich, M., and Hemmings, B. A., 1995, Inhibition of glycogen synthase kinase-3 by insulin mediated by protein kinase B, *Nature* 378:785-789; Datta, S. R., Dudek, H., Tao, X., Masters, S., Fu, H., Gotoh, Y., and Greenberg, M. E., 1997, Akt phosphorylation of BAD couples survival signals to the cell-intrinsic death machinery, *Cell* 91:231-241; and Zheng, W. H., Kar, S., and Quirion, R., 2000, Insulin-like growth factor-1-induced phosphorylation of the Forkhead family transcription factor FKHRL1 is mediated by Akt kinase in PC12 cells, *J Biol Chem* 275:39152-39158). Conversely, dephosphorylation of Akt decreases its activity, derepresses pro-apoptotic proteins and results in the sensitization of the cell to environmental stressors and initiation of processes leading to death (Gao, T., Furnari, F., and Newton, A. C., 2005, PHLPP: a phosphatase that directly dephosphorylates Akt, promotes apoptosis, and suppresses tumor growth, *Mol Cell* 18:13-24; and Ugi, S., Imamura, T., Maegawa, H., Egawa, K., Yoshizaki, T., Shi, K., Obata, T., Ebina, Y., Kashiwagi, A., and Olefsky, J. M., 2004, Protein phosphatase 2A negatively regulates insulin's metabolic signaling pathway by inhibiting Akt (protein kinase B) activity in 3T3-L1 adipocytes, *Mol Cell Biol* 24:8778-8789). Akt has multiple additional metabolic and trophic actions, such as the stimulation of the glucose transporter (glut-4), on mitochondrial function and synaptic plasticity (Horwood, J. M., Dufour, F., Laroche, S., and Davis, S., 2006, signaling mechanisms mediated by the phosphoinositide 3-kinase/Akt cascade in synaptic plasticity and memory in the rat, *Eur J Neurosci* 23:3375-3384; Tapodi, A., Debreceni, B., Hanto, K., Bognar, Z., Wittmann, I., Gallyas, F., Jr., Varbiro, G., and Sumegi, B., 2005, Pivotal role of Akt activation in mitochondrial protection and cell survival by poly(ADP-ribose) polymerase-1 inhibition in oxidative stress, *J Biol Chem* 280:35767-35775; and Uchiyama, T., Engelman, R. M., Maulik, N., and Das, D. K., 2004, Role of Akt signaling in mitochondrial survival pathway triggered by hypoxic preconditioning, *Circulation* 109:3042-3049).

Interference with or alteration of the Akt signaling pathway has emerged as an important feature in several neurodegenerative diseases characterized by neuronal attrition including AD and schizophrenia (Griffin, R. J., Moloney, A., Kelliher, M., Johnston, J. A., Ravid, R., Dockery, P., O'Connor, R., and O'Neill, C., 2005, Activation of Akt/PKB, increased phosphorylation of Akt substrates and loss and altered distribution of Akt and PTEN are features of Alzheimer's disease pathology, *J Neurochem* 93:105-117; Pei, J. J., Khatoon, S., An, W. L., Nordlinder, M., Tanaka, T., Braak, H., Tsujio, I., Takeda, M., Alafuzoff, I., Winblad, B., et al., 2003, Role of protein kinase B in Alzheimer's neurofibrillary pathology, *Acta Neuropathol* (Berl) 105:381-392; and Rickle, A., Bogdanovic, N., Volkman, I., Winblad, B., Ravid, R., and Cowbum, R.F., 2004, Akt activity in Alzheimer's disease and other neurodegenerative disorders, *Neuroreport* 15:955-959.

The PI3K-Akt signaling pathway is a major site of control for numerous cellular response mechanisms to environmental stress, and growth and differentiation signals. This pathway is pivotally affected in the opposing processes of tumorigenesis and apoptosis (Martelli, A. M., Faenza, I., Billi, A. M., Manzoli, L., Evangelisti, C., Fala, F., and Cocco, L., 2006, Intranuclear 3'-phosphoinositide metabolism and Akt signaling: new mechanisms for tumorigenesis and protection against apoptosis? *Cell Signal* 18:1101-1107; and Asano, T., Yao, Y., Shin, S., McCubrey, J., Abbruzzese, J. L., and Reddy, S. A., 2005, Insulin receptor substrate is a mediator of phosphoinositide 3-kinase activation in quiescent pancreatic cancer cells, *Cancer Res* 65:9164-9168). Once stimulated, insulin- and IGF-receptor tyrosine kinases next phosphorylate insulin receptor substrate (IRS), which then initiates the PI3K-Akt signaling cascade (Myers, M. G., Jr., Sun, X. J., and White, M. F., 1994, The IRS-1 signaling system, *Trends Biochem Sci* 19:289-293; Shpakov, A. O., and Pertseva, M. N., 2000, Structural and functional characterization of insulin receptor substrate proteins and the molecular mechanisms of their interaction with insulin superfamily tyrosine kinase receptors and effector proteins, *Membr Cell Biol* 13:455-484; and Andjelkovic, M., Alessi, D. R., Meier, R., Fernandez, A., Lamb, N. J., Frech, M., Cron, P., Cohen, P., Lucocq, J. M., and Hemmings, B. A., 1997, Role of translocation in the activation and function of protein kinase B, *J Biol Chem* 272:31515-31524). PI3K activation, in turn, results in the 3'-phosphorylation of second messenger, membrane-bound signaling inositol lipids. These lipids (e.g., PtdIns P3 (PIP3)) bring together PDK and Akt in a sub-membrane complex through interaction with each of their pleckstrin homology (PH) domains (Brunet, A., Datta, S. R., and Greenberg, M. E., 2001, Transcription-dependent and independent control of neuronal survival by the PI3K-Akt signaling pathway, *Curr Opin Neurobiol* 11:297-305). After sequential activation by PDK and another kinase, Akt phosphorylates a number of cellular targets, regulating their function (Alessi, D. R., James, S. R., Downes, C. P., Holmes, A. B., Gaffney, P. R., Reese, C. B., and Cohen, P., 1997, Characterization of a 3-phosphoinositide-dependent protein kinase which phosphorylates and activates protein kinase B alpha, *Curr Biol* 7:261-269).

Akt is activated through phosphorylations at Thr308 in the catalytic domain and Ser473 in the regulatory domain upon translocation from cytosol to the plasma membrane. PhosphoThr308 is essential while Ser 473 phosphorylation is required for full activation of Akt. Phosphoinositide-dependent protein kinase 1 (PDK1) was identified as the protein kinase responsible for the phosphorylation of Thr308 on Akt (Stokoe, D., Stephens, L. R., Copeland, T., Gaffney, P. R., Reese, C. B., Painter, G. F., Holmes, A. B., McCormick, F., and Hawkins, P. T., 1997, Dual role of phosphatidylinositol-3,4,5-trisphosphate in the activation of protein kinase B, *Science* 277:567-570; and Balendran, A., Casamayor, A., Deak, M., Paterson, A., Gaffney, P., Currie, R., Downes, C. P., and Alessi, D. R., 1999, PDK1 acquires PDK2 activity in the presence of a synthetic peptide derived from the carboxyl terminus of PRK2, *Curr Biol* 9:393-404). The protein kinase candidates for the Ser473 phosphorylation include: MAPKAP kinase-2 (PDK2), protein kinase Cα (PKCα) isoforms, integrin-linked kinase (ILK), DNA-dependent protein kinase (DNA-PK), ataxia telangiectasia mutated (ATM) gene product, mammalian target of rapamycin (mTOR), PDK1 itself, a still unknown kinase or an autophosphorylation event (Bayascas, J. R., and Alessi, D. R., 2005, Regulation of Akt/PKB Ser473 phosphorylation, *Mol Cell* 18:143-145; Feng, J., Park, J., Cron, P., Hess, D., and Hemmings, B. A., 2004, Identification of a PKB/Akt hydrophobic motif Ser473 kinase as DNA-dependent protein kinase, *J Biol Chem* 279:41189-41196; Leslie, N. R., Biondi, R. M., and Alessi, D. R., 2001, Phosphoinositide-regulated kinases and phosphoinositide phosphatases, *Chem Rev* 101:2365-2380; Sarbassov, D. D., Guertin, D. A., Ali, S. M., and Sabatini, D. M., 2005, Phosphorylation and regulation of Akt/PKB by the rictor-mTOR complex, *Science* 307:1098-1101; Toker, A., and Newton, A. C., 2000, Akt/protein kinase B is regulated by autophosphorylation at the hypothetical PDK-2 site, *J Biol Chem* 275:8271-8274; and Hresko, R. C., and Mueckler, M., 2005, mTOR.RICTOR is the Ser473 kinase for Akt/protein kinase B in 3T3-L1 adipocytes, *J Biol Chem* 280:40406-40416). The lack of consensus is illustrated by one study in 3T3-L1 adipocytes in which depletion of DNA-PK, ATM, or ILK had no effect on insulin-stimulated Akt Ser473 phosphorylation, whereas the depletion of Rictor resulted in inhibition (de la Monte, S. M., Tong, M., Lester-Coll, N., Plater, M., Jr., and Wands, J. R., 2006, Therapeutic rescue of neurodegeneration in experimental type 3 diabetes: relevance to Alzheimer's disease, *J Alzheimers Dis* 10:89-109).

Previous studies of the effects of intracellular β-amyloid on this pathway have suggested that intraneuronal Aβ1-42 expression leads to a sequential decrease in the levels of p-Akt, an increase in activation of GSK-3β, and induction of apoptosis (Magrane, J., Rosen, K. M., Smith, R. C., Walsh, K., Gouras, G. K., and Querfurth, H. W., 2005, Intraneuronal beta-amyloid expression downregulates the Akt survival pathway and blunts the stress response, *J Neurosci* 25:10960-10969).

There is widening recognition that AD is closely linked to a relative state of insulin resistance in the brain, so-called type III diabetes (Messier, C., and Teutenberg, K., 2005, The role of insulin, insulin growth factor, and insulin-degrading enzyme in brain aging and Alzheimer's disease, *Neural Plast* 12:311-328). Levels of insulin-like growth factor I (IGF-I), insulin and cognate receptors are significantly dysregulated in AD brain (Steen, E., Terry, B. M., Rivera, E. J., Cannon, J. L., Neely, T. R., Tavares, R., Xu, X. J., Wands, J. R., and de la Monte, S. M., 2005, Impaired insulin and insulin-like growth factor expression and signaling mechanisms in Alzheimer's disease—is this type 3 diabetes? *J Alzheimers Dis* 7:63-80; and Hoyer, S., 2004, Causes and consequences of disturbances of cerebral glucose metabolism in sporadic Alzheimer disease: therapeutic implications, *Adv Exp Med Biol* 541:135-152). In normal brain, IGF-I and insulin promote glucose utilization, energy metabolism and neuronal survival (Bondy, C. A., and Cheng, C. M., 2004, Signaling by insulin-like growth factor 1 in brain, *Eur J Pharmacol* 490:25-31), in large part through PI3K/Akt/GSK-30 signaling (Abbott, M. A., Wells, D. G., and Fallon, J. R., 1999, The insulin receptor tyrosine kinase substrate p58/53 and the insulin receptor are components of CNS synapses, *J Neurosci* 19:7300-7308). Insulin receptors populate neuronal synapses and astrocytes in memory-processing brain regions (Lee, C. C., Huang, C. C., Wu, M. Y., and Hsu, K. S., 2005, Insulin stimulates postsynaptic density-95 protein translation via the phosphoinositide 3-kinase-Akt-mammalian target of rapamycin signaling pathway, *J Biol Chem* 280:18543-18550). Acute insulin treatment increased memory function in rats on a passive-avoidance task (Park, C. R., Seeley, R. J., Craft, S., and Woods, S. C., 2000, Intracerebroventricular insulin enhances memory in a passive-avoidance task, *Physiol Behav* 68:509-514) and in small studies involving normal adults and AD patients (Kern, W., Peters, A., Fruehwald-Schultes, B., Deininger, E., Born, J., and Fehm, H. L., 2001, Improving influence of insulin on cognitive functions in humans, *Neuroendocrinology* 74:270-280; Zhao, L., Teter, B., Morihara, T., Lim, G. P., Ambegaokar, S. S., Ubeda, O. J., Frautschy, S. A., and Cole, G. M., 2004, Insulin-degrading enzyme as a downstream target of insulin receptor signaling cascade: implications for Alzheimer's disease intervention, *J Neurosci* 24:11120-11126; and Ho, L., Qin, W., Pompl, P. N., Xiang, Z., Wang, J., Zhao, Z., Peng, Y., Cambareri, G., Rocher, A., Mobbs, C. V., et al., 2004. Diet-induced insulin resistance promotes amyloidosis in a transgenic mouse model of Alzheimer's disease, *Faseb J* 18:902-904).

Primary hippocampal neurons treated with insulin show an inductive effect on insulin degrading enzyme (IDE) protein levels. The feed forward effect is mediated by PI3K/Akt (Zhao, L., Teter, B., Morihara, T., Lim, G. P., Ambegaokar, S. S., Ubeda, O. J., Frautschy, S. A., and Cole, G. M., 2004, Insulin-degrading enzyme as a downstream target of insulin receptor signaling cascade: implications for Alzheimer's disease intervention, *J Neurosci* 24:11120-11126). IDE is a metalloprotease enzyme also held responsible for Aβ monomer degradation. Thus, IDE deficiency (IDE −/− mice) resulted in a decrease degradation in both brain membrane fractions and primary neuronal cultures and in the cerebral accumulation of Aβ (Farris, W., Mansourian, S., Chang, Y., Lindsley, L., Eckman, E. A., Frosch, M. P., Eckman, C. B., Tanzi, R. E., Selkoe, D. J., and Guenette, S., 2003, Insulin-degrading enzyme regulates the levels of insulin, amyloid beta-protein, and the beta-amyloid precursor protein intracellular domain in vivo, *Proc Natl Acad Sci USA* 100:4162-4167). Similarly, insulin resistance and IDE deficiencies created in Tg2576 mice fed and oil-enriched diet, or one high in fat, were associated with increased Aβ monomer buildup and plaque burden (Zhao, L., Teter, B., Morihara, T., Lim, G. P., Ambegaokar, S. S., Ubeda, O. J., Frautschy, S. A., and Cole, G. M., 2004, Insulin-degrading enzyme as a downstream target of insulin receptor signaling cascade: implications for Alzheimer's disease intervention, *J Neurosci* 24:11120-11126; and Ho, L., Qin, W., Pompl, P. N., Xiang, Z., Wang, J., Zhao, Z., Peng, Y., Cambareri, G., Rocher, A., Mobbs, C. V., et al., 2004, Diet-induced insulin resistance promotes amyloidosis in a transgenic mouse model of Alzheimer's disease, *Faseb J* 18:902-904).

From knock-down models that test the IGF-I, IR and IRS axis, the loss of insulin signaling is expected to increase tau phosphorylation at AD-relevant GSK-3β and cdk5 sites (Cheng, C. M., Reinhardt, R. R., Lee, W. H., Joncas, G., Patel, S. C., and Bondy, C. A., 2000, Insulin-like growth factor 1 regulates developing brain glucose metabolism, *Proc Natl Acad Sci U S A* 97:10236-10241; and Schubert, M., Gautam, D., Surjo, D., Ueki, K., Baudler, S., Schubert, D., Kondo, T., Alber, J., Galldiks, N., Kustermann, E., et al., 2004, Role for neuronal insulin resistance in neurodegenerative diseases, *Proc Natl Acad Sci U S A* 101:3100-3105) and impair insulin-mediated inhibition of apoptosis as well as the stimulation of glucose uptake. Animal models in which brain insulin is depleted by intracerebral streptozotocin also have loss of the same insulin signaling components and show neurodegenerative changes in common with AD (Lester-Coll, N., Rivera, E. J., Soscia, S. J., Doiron, K., Wands, J. R., and de la Monte, S. M., 2006, Intracerebral streptozotocin model of type 3 diabetes: relevance to sporadic Alzheimer's disease, *J Alzheimers Dis* 9:13-33). Although the results argue for activation of insulin signaling in AD therapeutics, chronic insulin stimulation may have negative consequences such as the development of peripheral insulin resistance and the accumulation of Aβ through competition for a limited pool of IDE in AD brain.

Therefore, different targets should be sought.

SUMMARY OF THE INVENTION

Aspects of the invention relate to compositions and methods for treating disorders associated with specific beta-amyloid inhibition of PDK1-dependent Akt activation.

Aspects of the invention are based, at least in part, on the discovery that intracellular β-amyloid (Aβ) selectively interferes with the association of PDK1 and Akt. In some embodiments, the invention provides methods of screening for compounds that protect the PDK1/Akt association from intracellular Aβ. In some embodiments, compounds selectively prevent intracellular Aβ from disrupting PDK1-dependent Akt activation without significantly affecting the activity of PDK1 and/or Akt in the absence of intracellular Aβ. In some embodiments, the invention provides methods for treating Alzheimer's disease and/or any other condition associated with Aβ-mediated disruption of PDK1/Akt interactions. In some embodiments, the invention provides methods and compositions for protecting CNS cells (e.g., neural cells), muscle cells, and/or other cell types from the effects of intracellular Aβ accumulation. In some embodiments, the invention provides methods and compositions for restoring normal levels (or improving the level) of insulin/Akt signaling in CNS cells (e.g., neural cells), muscle cells, and/or other cell types that express intracellular Aβ (e.g., at above-normal levels).

In some embodiments, the invention relates to a method of identifying a compound that reduces β-amyloid (Aβ) inhibition of Akt kinase activation by a PDK kinase domain. Assays disclosed herein can be protein binding assays, substrate binding assays, substrate activation assays, other in vitro or in vivo assays, or any combination thereof.

In some embodiments, a method includes evaluating a compound (e.g., a first compound) in an assay including a molecule containing an Akt kinase domain (e.g., an AKT holoprotein, a fragment of the full-length protein that retains an Akt kinase domain, a recombinant protein that contains an Akt kinase domain, a recombinant protein that contains an Akt regulatory domain, etc., or any combination thereof) and a molecule containing a PDK kinase domain (e.g., a PDK holoprotein, a fragment of the full length protein that retains the PDK kinase doamin, a recombinant protein that contain a PDK kinase domain, etc., or any combination thereof) in the presence of an Aβ polypeptide.

Accordingly, in some embodiments, an assay involves contacting a first compound with a preparation comprising an Akt kinase domain, a PDK1 kinase domain, and an Aβ polypeptide; determining a first amount of active Akt; and comparing the first amount to a reference amount of active Akt in the absence of the first compound, wherein a significantly higher amount of active Akt in the presence of the first compound identifies the first compound as a candidate for reducing Aβ mediated inhibition of Akt activation by PDK1. However, in some embodiments, an assay involves contacting a first compound with a preparation comprising an Akt regulatory domain, a PDK1 kinase domain, and an Aβ polypeptide; determining a first amount of active Akt; and comparing the first amount to a reference amount of active Akt in the absence of the first compound, wherein a significantly higher amount of active Akt in the presence of the first compound identifies the first compound as a candidate for reducing Aβ mediated inhibition of Akt activation by PDK1.

In some embodiments, activation of an Akt regulatory domain may be evaluated by detecting the level of phospho S473 on the regulatory domain. However, it should be appreciated that an assay that involves detecting substrate phosphorylation requires a kinase domain. Accordingly, in a functional assay involving an Akt regulatory domain, the regulatory domain is fused to a kinase domain (e.g.,. an Akt kinase domain or other suitable kinase domain) in order to be able to measure the effect on the Akt regulatory domain by determining the level of substrate activation (e.g., phosphorylation).

In some embodiments, the Akt kinase domain comprises a T-loop including Threonine 308 of the full length Akt protein. In some embodiments, the Akt kinase domain is provided as part of the full length Akt protein.

In some embodiments, an Akt kinase domain is provided in a fusion protein. The fusion protein may be a chimeric protein that includes a regulatory domain (RD—also referred to as a hydrophobic motif: HM) from a different protein. For example, the regulatory domain may be from PRK2 (e.g., the full length PRK2 regulatory domain, a fragment of the PRK2 regulatory domain, for example a 24 amino acid long PIF peptide also known as a PIFtide), SGK, PKA, PKB, or any other AGC protein that has a regulatory domain (e.g., that has a regulatory domain that fits into a pocket on the PDK kinase domain), or any other protein that has a regulatory domain that is similar to the Akt regulatory domain.

In some embodiments, an Akt regulatory domain is provided in a fusion protein. The fusion protein may be a chimeric protein that includes a kinase domain from a different protein. For example, the kinase domain may be from PRK2, SGK, PKA, PKB, or any other AGC protein that has a kinase domain (e.g., that has a kinase domain that can be regulated like an Akt kinase domain when fused to an Akt regulatory domain).

Examples of regulatory domains that interact with PDK and that can be used in a fusion protein comprising an Akt kinase domain are described, for example, in Biondi et al., EMBO J., August 2002, 21(16) pages 4219-28: High resolution crystal structure of the human PDK1 catalytic domain defines the regulatory phosphopeptide docking site; and Biondi et al., EMBO J., August 2001, 20(16) pages 4380-90.

In some embodiments, the Aβ polypeptide is a recombinant or synthetic Aβ polypeptide. In some embodiments, the recombinant Aβ polypeptide is isolated from a cell that expresses the recombinant Aβ polypeptide. In some embodiments, the cell is from a cell line that stably expresses the recombinant Aβ polypeptide when grown in culture in vitro. In some embodiments, the cell is a bacterial or eukaryotic cell. In some embodiments, the cell is transiently transfected with a viral or cDNA construct encoding the recombinant Aβ polypeptide. In some embodiments, the Aβ polypeptide is the major 42 amino acid long pathogenic Aβ protein, a shorter 40 amino acid long Aβ40 protein, or a longer C99 variant comprising the Aβ42 sequence, a fragment consisting of residues 25-35 of the full length Aβ protein, or the full length APP. However, it should be appreciated that other Aβ variants also may be used provided they have substantially the same inhibitory properties as described herein in the context of the different assays.

In some embodiments, the reference amount of active Akt is determined in the presence of an inactive control compound. In some embodiments, the amount of active Akt is detected as an amount of phosphorylated Akt kinase domain, an amount of phosphorylated Akt regulatory domain, an amount of phosphorylated Serine or Threonine on a heterologous protein fused to an Akt regulatory domain or kinase domain in a recombinant Akt hybrid protein, an amount of phosphorylated Akt substrate polypeptide, an amount of intramitochondrial Akt, or a combination thereof. In some embodiments, the amount of phosphorylated Akt domain is determined by ELISA. In some embodiments, the Akt substrate polypeptide is based on a GSK3β, BAD, TAU, eNOS, CREB, Caspase-9, IκB, or FOXO polypeptide, or a combination thereof. In some embodiments, the amount of phosphorylated substrate polypeptide is determined by ELISA.

It should be appreciated that the different Akt, PDK, and Aβ proteins and domains described above may be used in connection with any suitable in vitro (e.g., a substrate phosphorylation or other functional assay, a direct detection assay, or any combination thereof) or in vivo assay described herein.

In some aspects, the interaction between Akt and PDK may be detected directly (as opposed to determining the level of substrate activation). In some embodiments, the level of association between the Akt regulatory domain and the PDK kinase domain may be evaluated. Accordingly, aspects of the invention relate to a method of identifying a compound that reduces Aβ inhibition of Akt activation by PDK1, by contacting a first compound with a preparation comprising an Akt regulatory domain, a PDK1 kinase domain, and an Aβ protein; determining a first amount of a complex comprising the Akt regulatory domain associated with the PDK1 kinase domain; and comparing the first amount to a reference amount of complex comprising the Akt regulatory domain associated with the PDK1 kinase domain in the absence of the first compound, wherein a significantly higher amount of complex in the presence of the candidate compound identifies the first compound as a candidate for reducing Aβ inhibition of Akt activation by PDK1.

In some embodiments, any association between the PDK kinase domain and the Akt kinase domain may be assayed. Accordingly, aspects of the invention relate to a method of identifying a compound that reduces Aβ inhibition of Akt activation by PDK1, by contacting a first compound with a preparation comprising an Akt kinase domain, a PDK1 kinase domain, and an Aβ protein; determining a first amount of a complex comprising the Akt kinase domain associated with the PDK1 kinase domain; and comparing the first amount to a reference amount of complex comprising the Akt kinase domain associated with PDK1 kinase domain in the absence of the first compound, wherein a significantly higher amount of complex in the presence of the first compound identifies the first compound as a candidate for reducing Aβ inhibition of Akt activation by PDK1.

In any of the assay configurations described herein, the reference amount of complex may be determined in the presence of an inactive control compound. In some embodiments, the first amount of the complex is determined by ELISA. In some embodiments, the Akt domain (e.g., the regulatory domain or kinase domain, either alone or in the context of a full length protein, portion thereof, or fusion protein) is immobilized. In some embodiments, the Akt domain is immobilized via a biotin-streptavidin interaction. In some embodiments, the Akt domain is immunologically immobilized. In some embodiments, the Akt domain is immobilized on a solid substrate or on beads in a solution. In some embodiments, the PDK1 domain (e.g, kinase domain, either alone or in the context of a full length protein, portion thereof, or fusion protein) is immobilized. In some embodiments, the PDK1 domain is immobilized via a biotin-streptavidin interaction. In some embodiments, the PDK1 domain is immunologically immobilized. In some embodiments, the PDK1 domain is immobilized on a solid substrate or on beads in a solution. In some embodiments, the phosphorylated substrate is immobilized. In some embodiments, the phosphate sensor is immobilized. In some embodiments, the phosphate sensor is a fluorescent sensor immobilized on a bead.

It should be appreciated that any of the Akt and/or PDK proteins, domains, or variants thereof described herein may be fused to a suitable pleckstrin homology domain (PHD). For example, an Akt domain (e.g., regulatory and/or kinase) may be fused to an Akt PHD. Similarly, a PDK domain may be fused to a PDK PHD. However, other suitable PHDs may be used. It should be appreciated that a PHD may be useful when an assay is performed in the context of a natural or reconstituted membrane. A PHD may be included in any other assay. However, a PHD may be excluded from the Akt and/or PDK molecules in certain assays (e.g., when the molecules are provided in the absence of a membrane or lipid for an assay in solution or an assay involving one or more immobilized components.

Aspects of the invention relate to a method of identifying a compound that reduces Aβ mediated inhibition of Akt activation by PDK1, by: contacting a first compound with a preparation comprising a pleckstrin homology domain (PHD), a 3' phosphorylated phosphoinositide, and an Aβ polypeptide; detecting a first amount the pleckstrin homology domain associated with the 3' phosphorylated phosphoinositide; and comparing the first amount to a reference amount of the pleckstrin homology domain associated with the 3' phosphorylated phosphoinositide in the absence of the first compound, wherein a significantly higher amount of pleckstrin homology domain associated with the 3' phosphorylated phosphoinositide in the presence of the first compound identifies the first compound as a candidate for reducing Aβ inhibition of Akt activation by PDK1.

In some embodiments, the pleckstrin homology domain is specifically an Akt pleckstrin homology domain, a PDK1 pleckstrin homology domain, or a homologous pleckstrin homology domain that has similar PI(3,4)P2 and PI(3,4,5)P3 binding properties as the Akt pleckstrin homology domain, or similar PI(3,4)P2 and PI(3,4,5)P3 binding properties as the PDK pleckstrin homology domain. According to aspects of the invention, Akt has a standard group 3 or (type 3) PH domain that only binds to PIP2 and PIP3 and undergoes a conformational change when it binds to the lipids; and PDK has a group 2 PH domain that that binds PIP3 and PI45 and does not undergo a conformational change upon lipid binding.

In some embodiments, the 3' phosphorylated phosphoinositide is a PI(3,4,5)P3, PI(3,4)P2, or PI(1,3,4,5)P4 lipid. In some embodiments, the 3' phosphorylated phosphoinositide is a synthetic lipid. In some embodiments, the synthetic lipid is in a free or vesicle form. In some embodiments, the 3' phosphorylated phosphoinositide is provided in a cell derived membrane lipid preparation in an activated form. In some embodiments, the 3' phosphorylated phosphoinositide is immobilized. In some embodiments, the 3' phosphorylated phosphoinositide is immobilized on a membrane. In some embodiments, the pleckstrin homology domain is immobilized.

As used herein, Akt refers to Akt-1. However, it should be appreciated that the assays described in the context of Akt or Akt-1 also may be performed using Akt-2 or Akt-3 or similar domains or recombinant variants thereof as described in the context of Akt or Akt-1. Akt-1 and Akt-2 are expressed throughout the body and have overlapping functions. Akt-1 and Akt-2 are known to have similar kinase functions. According to aspects of the invention, the Akt-1 (PKB-1) domains are as follows: PHD from residues 1 to 123, catalytic (or kinase domain) residues from 154 to 446, and regulatory (HM) residues from 469 to 475.

Similarly, as used herein PDK refers to PDK-1. However, similar assays may be performed using PDK related proteins or domains. According to aspects of the invention, the PDK-1 domains are as follows: catalytic (or kinase domain) residues 71 to 359, and PHD from 459 to 550.

However, it should be appreciated that a recombinant Akt or PDK domain described herein may include a few additional or fewer amino acids provided that the presence or absence of these amino acids does not significantly impair the function of the domain in the assay.

It should be appreciated that any polypeptide described herein may be chemically synthesized, recombinant (e.g., purified from a recombinant cell), or isolated from natural sources. Polypeptides (with and without a tag) obtained from recombinant cells may be isolated or purified immunologically or on an affinity column or using any suitable chromatographic technique such as size filtration or any other technique or any combination of techniques. Recombinant cells may be cells that stably express a protein or polypeptide of interest (e.g., recombinant bacterial cells or immortalized mammalian cells). A bacterial cell may be any suitable cell (e.g., *E. coli*, etc.). In some embodiments, a cell that expresses a recombinant protein or polypeptide may be transiently transfected with a recombinant nucleic acid. For example, a cell may be transfected with a viral nucleic acid, a cDNA, or any other nucleic acid that encodes the polypeptide of interest.

These and other aspects of the invention are described in more detail in the following detailed description and examples.

BRIEF DESCRIPTION OF THE DRAWINGS

—FIGS. 2A-2D illustrate different non-limiting assay configurations;

FIGS. 3A-3D show non-limiting examples of experimental readouts that can be used to evaluate compounds according to methods of the invention—FIG. 3A shows the results of an in vitro Akt kinase assay, FIG. 3B shows the results of a TruLight™ assay for PDK1 dependent-Akt activation, FIG. 3C shows the results of an in vitro Akt/PDK1 interaction assay, and FIG. 3D shows the results of a coupled in vivo and in vitro Akt kinase assay that can be used to determine the impact of intracellular Aβ expression in live culture cells on Akt activation in their lysates;

—FIG. 4A shows Akt1 levels, activity, and interaction with PDK in normal and AD brain, FIG. 4B shows co-immunoprecipitation of β-amyloid with PDK and Akt1 in AD brain, and FIG. 4C shows IRβ, p85, and IRS-1 levels and interactions in AD brain;

FIGS. 5A-5D illustrate the cellular toxicity and prevention of Akt activation by intracellular Aβ1-42 expression in $C_2C_{12}$ myotubes—FIG. 5A shows adenovirus-mediated expression of $Aβ_{1-42}$, FIG. 5B shows viability assays, FIG. 5C shows Akt activation is partially prevented following Aβ expression, and FIG. 5D shows that autophosphorylation of the insulin receptor is unchanged;

—FIG. 6A shows in vitro Akt phosphorylation and activity assays, FIG. 6B shows Aβ specificity and dose dependence of inhibition in neuronal cells, FIG. 6C shows ADDL and fibril preparation, and FIG. 6D shows the relative effects of these amyloid conformers on PDK-dependent activation of Akt;

—FIG. 7A shows the quantification of PDK-dependent Akt1 phosphorylation ($K_i50 \approx 10$ μM) and activation ($K_i50 \approx 1$ μM) under in vitro Aβ conditions, indicating the 10× greater sensitivity of the activity assay, FIG. 7B shows the role of second messenger, PIP3, FIG. 7C shows that Aβ mediated inhibition can be washed out (is reversible) whereas PTEN effect is not, so Aβ is not acting like a phosphatase, and FIG. 7D shows Aβ effects on PDK-SGK, Rictor-Akt or PKA activities;

—FIG. 8A shows cell based interaction assay in $C_2C_{12}$ myotubes, FIG. 8B shows cell-free interaction assays, and FIG. 8C also shows in vitro interaction assay but using combined PDK or Akt-depleted cell extracts (relatively enriched for the other);

—FIG. 9A shows pre-activated Akt (by insulin) is not inhibited by Aβ42 from phosphorylating a GSK-3β consensus substrate, FIG. 9B shows pre-activated Akt is however dephosphorylated and inhibited by protein phosphatase 2A (PP2A), thus Aβ does not act like this phosphatase either, FIG. 9C shows extracellular Aβ has no effect on Akt signaling, FIG. 9D shows an insulin dose response stimulation of Akt phosphorylation is similarly unaffected by extracellular Aβ, and FIG. 9E shows that the phosphorylation status of PDK (pSer241) is unaffected by extracellular Aβ;

—FIG. 10A shows the time-dependence of PI3K activity, FIG. 10B shows that PI3K activity is maintained in the presence of Aβ, FIG. 10C shows dephosphorylation of P13P by phospholipase A2(PLA2) but not Aβ42, and FIG. 10D shows that PTEN, but not Aβ, inhibits PI3K as expected.

DETAILED DESCRIPTION OF THE INVENTION

Aspects of the invention relate to methods and compositions for treating Alzheimer's disease (AD). According to aspects of the invention, compounds that prevent intracellular Aβ from interfering with (e.g., inhibiting) PDK1-dependent Akt activation are useful for treating Alzheimer's disease and/or preventing or slowing the development of symptoms associated with Alzheimer's disease.

Aspects of the invention are based, at least in part, on the discovery that intracellular Aβ specifically interferes with the interaction between PDK1 and Akt. Previous studies have suggested that Aβ may interfere with many different physiological processes. However, the precise site of action of intracellular Aβ has not been identified until now. Aspects of the invention relate to methods and compositions that specifically protect PDK1/Akt interactions from the inhibitory effects of intracellular Aβ. In some embodiments, methods of the invention relate to assays for identifying compounds that prevent intracellular Aβ from interfering with (e g , inhibiting) the association between Akt and PDK (e.g., the PDK-mediated activation of Akt).

According to aspects of the invention, one or more of the pathogenic symptoms of Alzheimer's disease that are associated with increased intraneuronal levels of Aβ result from the inhibitory effect of intracellular Aβ on Akt activation, for instance when stimulated by insulin receptors, and particularly from the specific inhibitory effect of intracellular Aβ on a discrete step, the PDK-mediated activation of Akt. Accordingly, aspects of the invention relate to identifying compounds that can reestablish Akt signaling in subjects having high levels of intracellular (e.g., intraneuronal) Aβ by identifying compounds that can relieve the inhibitory effects of Aβ on interactions between PDK1 and Akt. In some embodiments, compounds identified according to methods of the invention are useful for preventing and/or treating one or more pathogenic symptoms of Alzheimer's disease.

Figure 1:
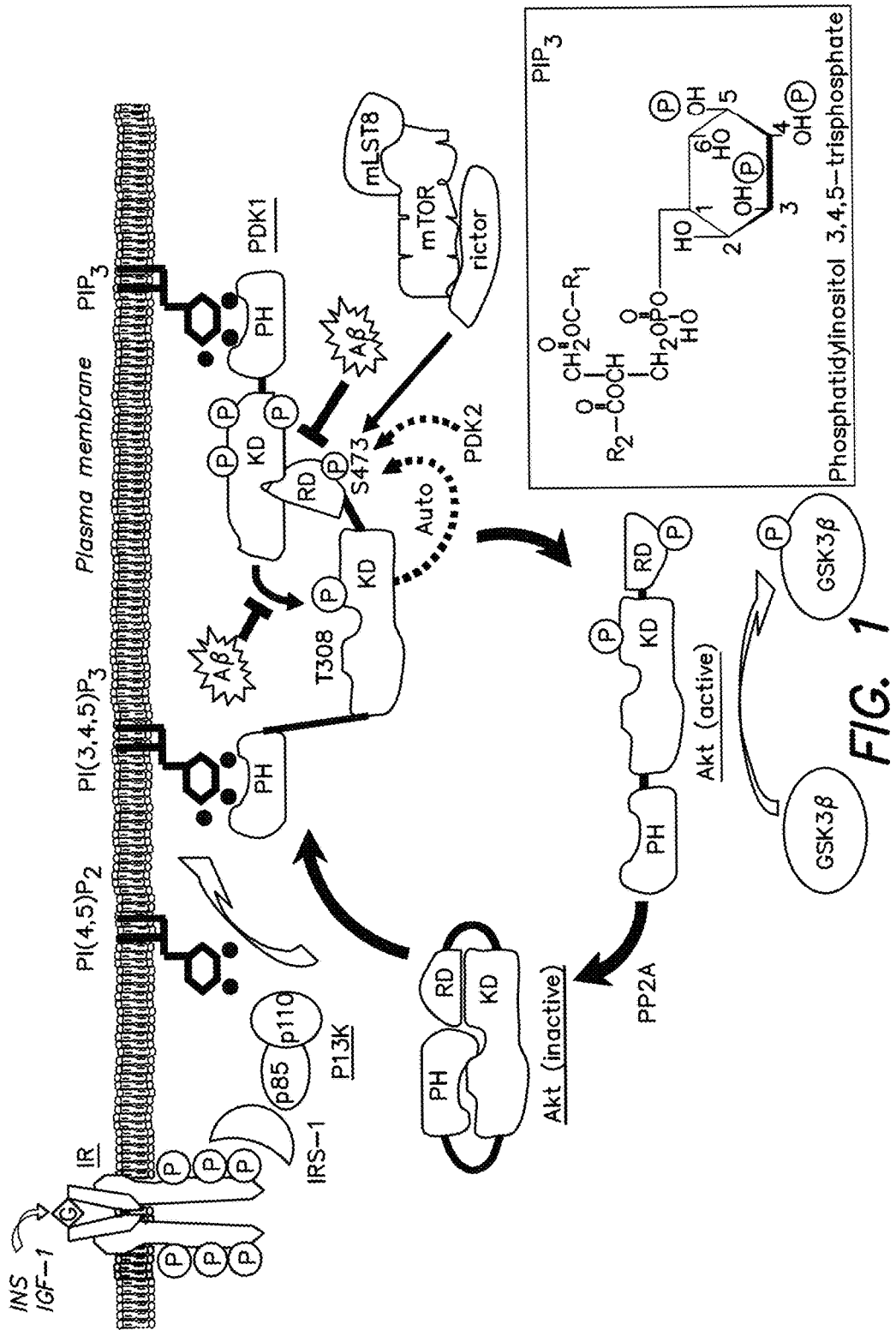
FIG. 1 illustrates non-limiting embodiments of interactions between Akt-1 and PDK-1, GSK phosphorylation is shown as a non-limiting example of a downstream reporter of Akt activation.

FIG. 1 is a non-limiting illustration of Aβ inhibition sites in the context of PDK1-dependent activation of Akt, as believed to occur under the lipid membrane. Pleckstrin homology domains (PH domains) are illustrated for both Akt and PDK1. Akt is illustrated as having a PH domain, a kinase domain (KD), and a regulatory domain (RD). PDK1 is illustrated as having a PH domain and a kinase domain (KD). It should be appreciated that the PH domains of PDK1 and Akt are different. The PH domains bind to PIP3 (PI(3,4,5)P3) in the lipid membrane. PIP3 is generated via the PI3K-dependent phosphorylation of PIP2 (PI(4,5)P2) as illustrated. Activation of PI3K by stimulation of the IR (e.g., in response to INS or IGF-1) is also illustrated.

According to aspects of the invention, Aβ directly interferes with PDK1-dependent activation of Akt by interfering with PDK1-dependent phosphorylation of T308 on Akt and/or by interfering with the interaction between the Akt's hydrophobic motif (HM) (also known as the regulatory domain RD) and the PDK1 kinase or catalytic domain (KD) as illustrated in FIG. 1.

According to aspects of the invention, in some embodiments Aβ interferes with the association between membrane PIP3 and the PH domain(s) of Akt and/or PDK1. Without wishing to be bound by theory, an Aβ-mediated disruption of the association between membrane PIP3 and one or both of the PH domains is expected to reduce the amount of PDK-dependent Akt activation.

Aspects of the invention relate to in vitro and/or in vivo assays for identifying compounds that reduce the inhibitory effects of Aβ on interactions between PDK1 and Akt (e.g., the direct association of PDK1 and Akt). In some embodiments, compounds are identified that do not significantly inhibit or activate PDK-mediated activation of Akt. In some embodiments, a candidate compound that is identified in a first assay as protecting the levels of Akt activation from intracellular Ab. The compound may be further evaluated to determine whether it selectively protects PDK-dependent Akt activation from intracellular Aβ without significantly changing this process in the absence of intracellular Aβ. According to the invention, selective compounds are useful, because they will not have unwanted side-effects associated with aberrant (e.g., increased or reduced) PDK-dependent Akt activation in cells that do not express Aβ (or that express normal levels of Aβ. Over-activation is undesirable as it may lead to tumorigenesis, enlarged heart (cardiac hypertrophy), enlarged skeletal muscle, and/or other undesirable side-effects. Reduced action in the absence of Aβ may be counter-productive and may aggravate AD. In some embodiments, useful compounds are expected to act as allosteric modulators of the Akt-PDK interaction and non-competitively neutralize the amyloid effect. It should be noted that in some embodiments, Aβ binds to both proteins in AD as indicated in FIG. 4B.

Assay Configurations

Akt Activity Assays Based on Substrate Modification.

In some embodiments, the inhibitory effect of Aβ on Akt activation may be measured indirectly by monitoring substrate phosphorylation. Any suitable natural or synthetic substrate may be used.

Figure 3A:
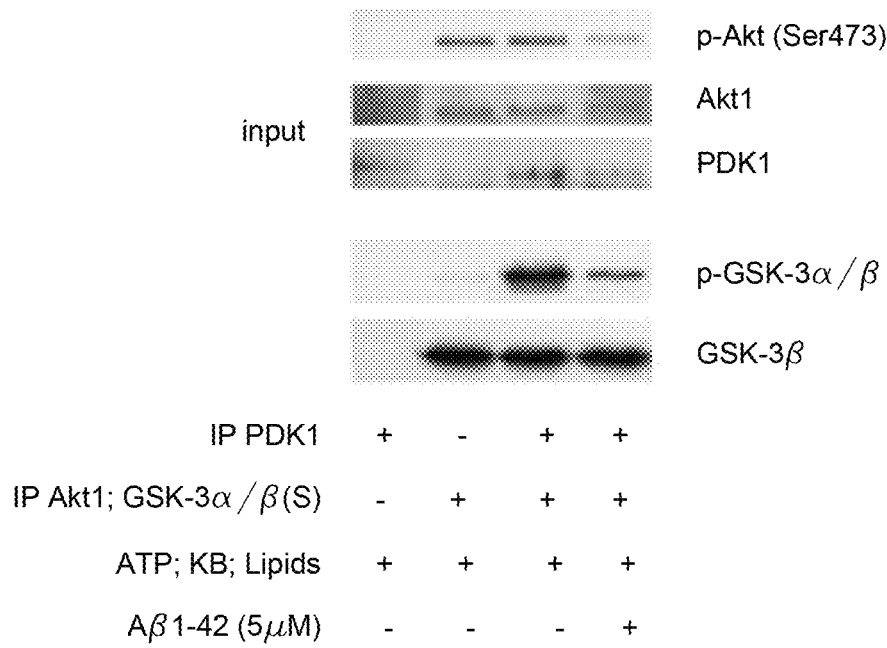

For example, as a means to measure the ability of Aβ to interfere with Akt signaling in a controlled cell-free system, an in vitro kinase assay may be used where immunoprecipitated-PDK1 and—Akt are mixed in the presence of activating phosphoinositide lipids and a synthetic Akt substrate bearing the phosphorylation sequence of GSK-3β fused to paramyosin. Synthetic Aβ1-42 is added prior to the start of the reactions. As seen in FIG. 3A, the presence of 5 μM Aβ dramatically inhibited the Akt-dependent phosphorylation of the synthetic GSK-3β target. This is also coupled with the reduction in the presence of the activating phosphorylation of Akt on Ser473. These data indicate that the effects of Aβ in this assay occur at a point upstream of Akt activity.

Figure 2A:
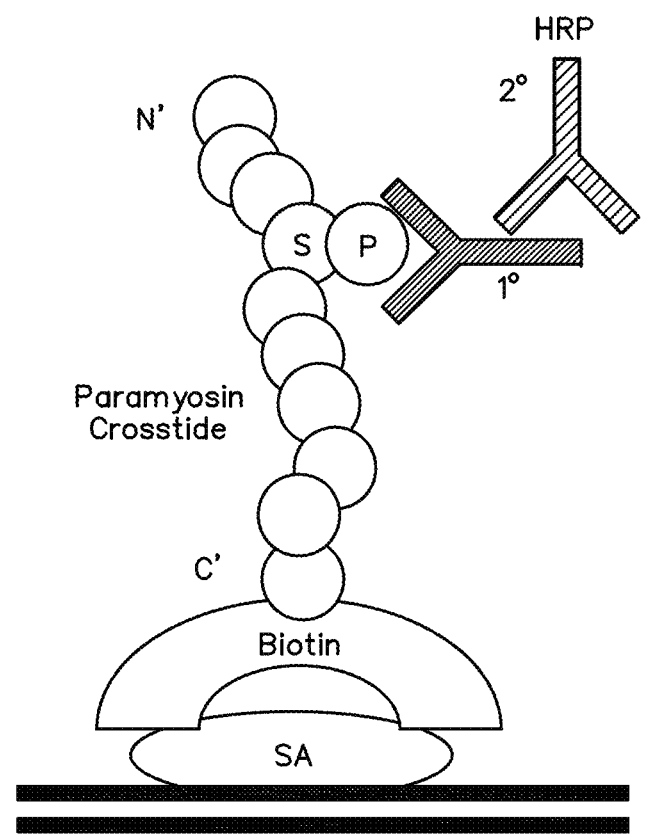
FIGS. 2A-2D illustrate non-limiting embodiments of assays for evaluating the effect of compounds on the Aβ-mediated inhibition of activations and interactions between PDK1 and Akt
Figure 2B:
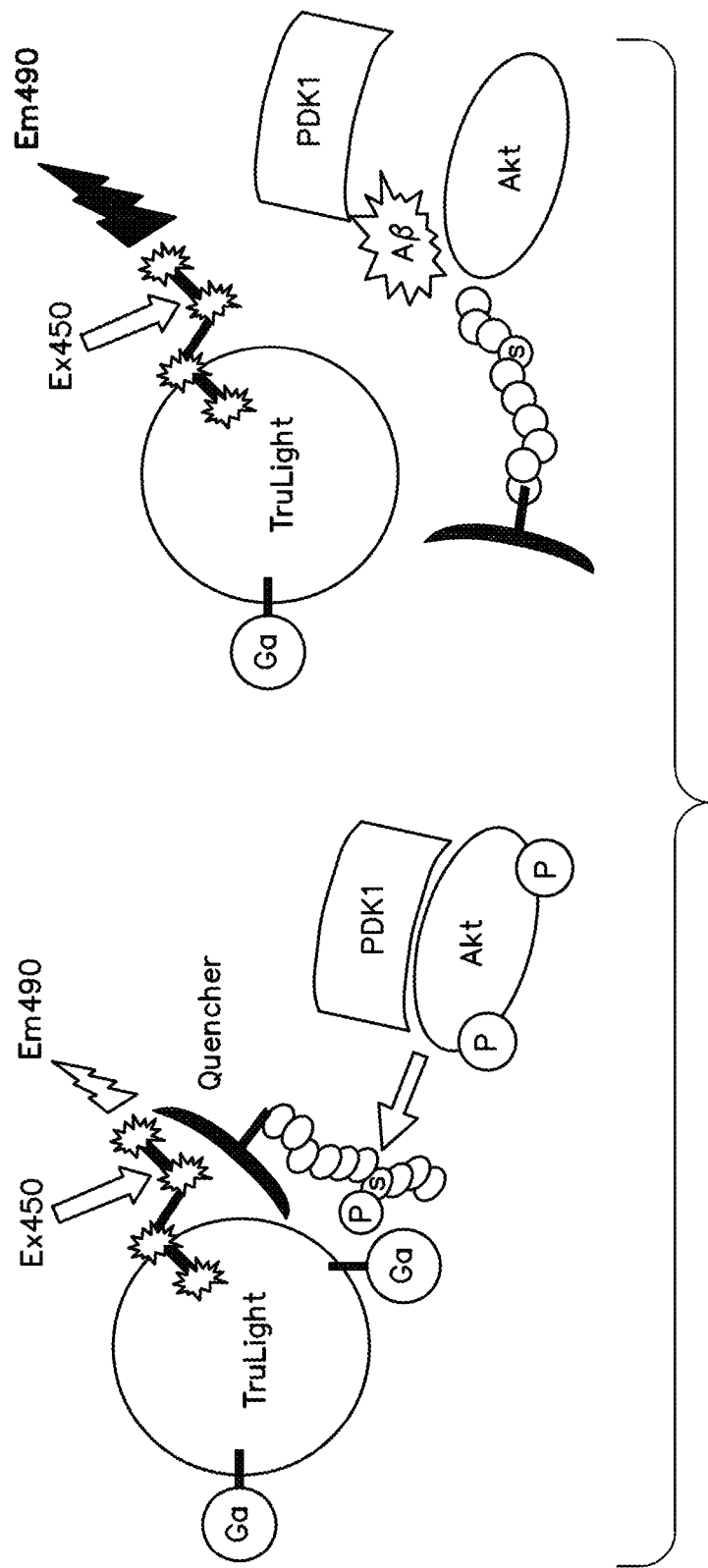

Accordingly, in some embodiments, GSK-3β phosphorylation may be evaluated. Aβ inhibition results in a decrease in GSK-3β phosphorylation. Accordingly, a compound that counters the effect of Aβ is expected to increase the levels of GSK-3β phosphorylation (or restore normal or close to normal levels of phosphorylation). Accordingly, in some embodiments the total level of activated Akt is determined using the conversion of non-limiting GSK into pSer-GSK in vitro. Assay components may be tested in any suitable configuration (e.g., individual wells, wells in a multiwell plate, for example a 384 well plate). Compounds may be tested in the presence and/or the absence of Aβ42. In some embodiments, the GSK peptide is biotinylated and the biotinylated GSK peptide is captured and anti-phosphopeptide is detected in a fluorescence-based ELISA. Accordingly, a compound of interest will restore normal or near-normal levels of substrate phosphorylation. FIG. 2A shows an example of an assay. Another example is shown in FIG. 2B. However, it should be appreciated that other configurations may be used for detecting substrate modifications as the invention is not limited in this respect. Also any suitable substrate may be used (e.g., a natural or synthetic polypeptide based on a GSK3β, BAD, TAU, eNOS, CREB, Caspase-9, IκB, FOXO, MDM2, TSC2, p27 polypeptide, or any other suitable polypeptide, or any combination thereof.

Figure 3B:
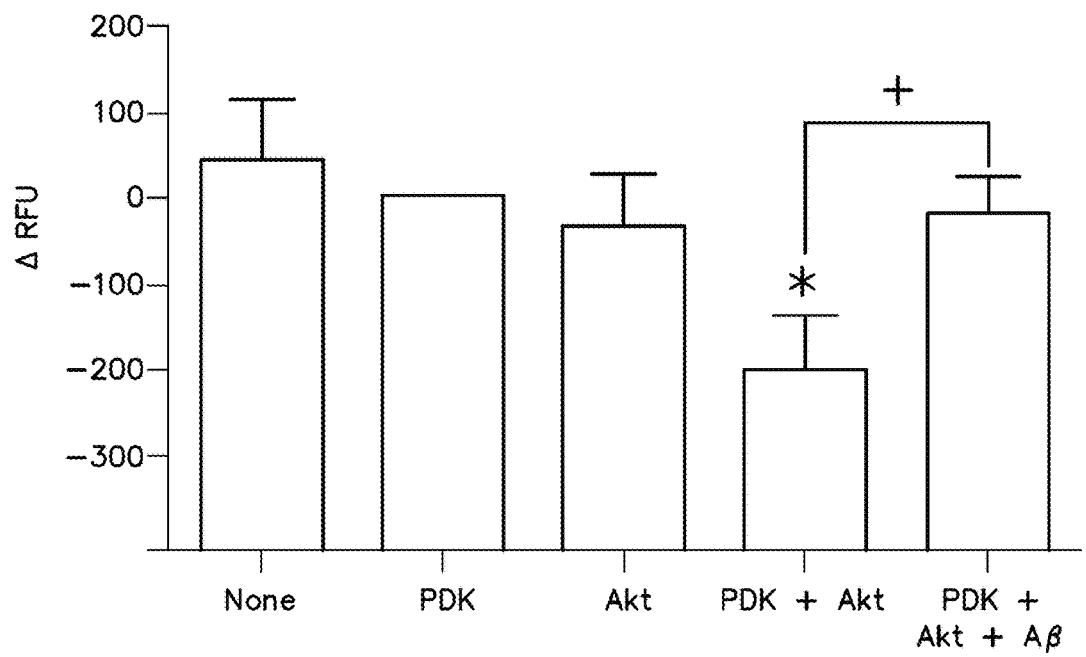

Non-limiting examples of substrate readout are shown in FIGS. 3A-B. FIG. 3A illustrates the readout of an in vitro Akt kinase assay Immunoprecipitated PDK1 and Akt were incubated with and without synthetic Aβ in the presence of lipids, ATP, kinase buffer and a synthetic GSK-3μtarget sequence. Addition of Aβ substantially interfered with Akt phosphorylation of the target. FIG. 3B illustrates results from a 384-well drug screening platform using a TruLight™ assay for PDK1-dependent Akt activation. However, it should be appreciated that other suitable platforms may be used. Immunoprecipitated PDK1 and Akt were incubated with and without synthetic Aβ in the presence ATP, kinase buffer, lipid and peptide substrate conjugated to a quencher moiety. Compounds can be screened to identify those that neutralize this effect of Aβ. However, it should be appreciated that other detection methods may be used as described herein.

Assays Based on Akt-PDK1 Interactions.

In some embodiments, direct detection of phospho-Akt and PDK1 bound to activated Akt may be evaluated using any suitable assay. For example, an Akt or PDK domain may be immobilized and the level of association may be determined by detected the amount of complex formed (with an immobilized PDK or Akt domain, respectively). Complexes may be detected using any suitable technique (color, fluorescence, radioactive label, enzymatic label, antibody binding, etc., or any combination thereof). It should be appreciated that a domain may be immobilized using any suitable support (e.g., multiwell plate, column, bead, Nickel affinity bead, etc., or any combination thereof). The domain may be immobilized using any suitable technique (e.g., via covalent interaction or via a capture agent, for example, an immunological capture agent, an affinity capture agent, for example using conventional protein tags (e.g., HA, FLAG, 6XHis, etc.).

Figure 2C:
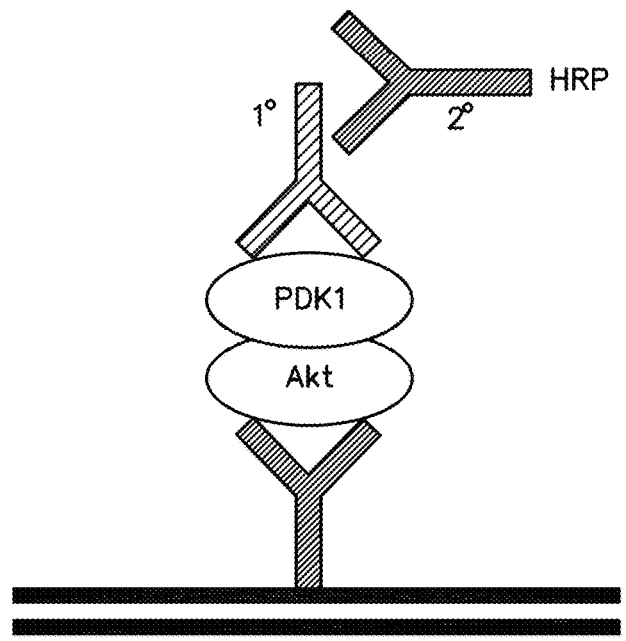
Figure 2D:
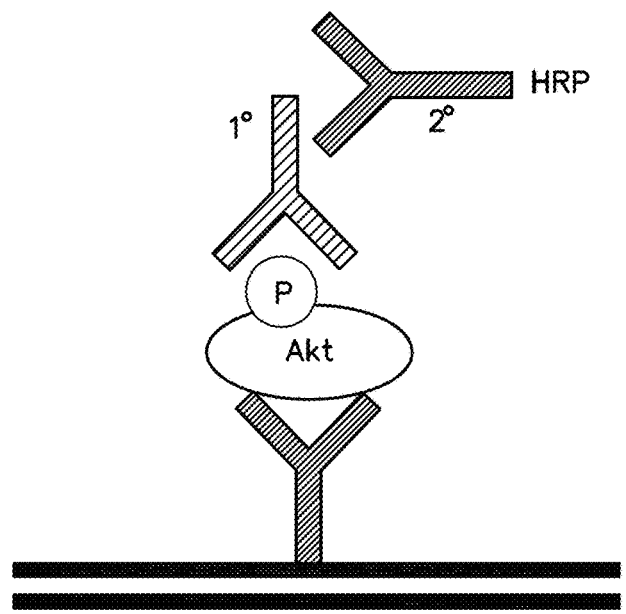

Non-limiting examples of detecting phosphorylated Akt are shown in FIGS. 2C and 2D. FIG. 2C shows the direct detection of an association between Akt and PDK. This results in Akt phosphorylation. A loss of this interaction gives rise to a loss of Akt phosphorylation. FIG. 2D shows an assay for directly detecting the presence of phosphorylated Akt.

Figure 3C:
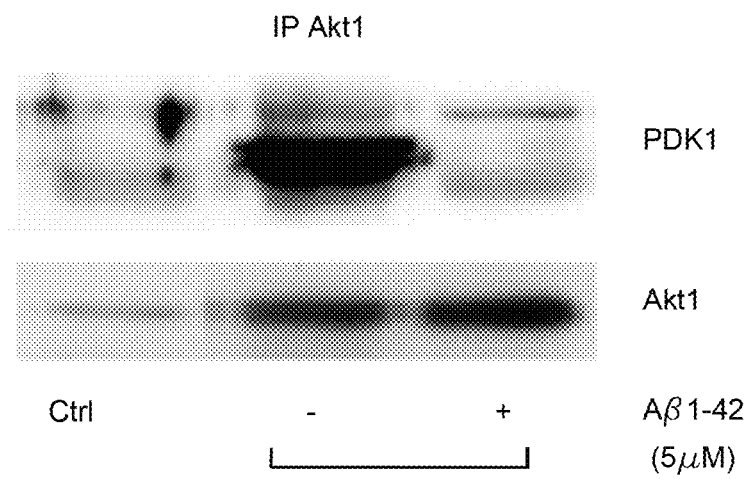

Non-limiting examples of signal readout are shown in FIG. 3C. In FIG. 3C, the results of an in vitro Akt/PDK1 interaction assay are shown. Cell extracts in which Akt and PDK1 were overexpressed were incubated with and without synthetic Aβ and allowed to interact, as a mimic of the intracellular environment. Following immunoprecipitation of Akt from the mixture, samples were electrophoresed and blotted for either PDK1 or Akt. Aβ reduces the association between Akt and PDK1.

Accordingly, the effect of Aβ on PDK/Akt interactions may be evaluated in any suitable in vitro assay. In some embodiments, PDK1 may be prepared from extracts of mouse $C_2C_{12}$ myotube cultures. To increase the amount of available Akt, this protein may be prepared from $C_2C_{12}$ myotubes that had previously been infected with an adenovirus expressing wild type Akt (Adv-wtAkt). In some embodiments, to measure the interaction between these proteins, the cell extracts above were mixed for 30 minutes at 30° C. either in the presence or absence of added 5 μM Aβ1-42. The IP/Western results in FIG. 3C show that the addition of synthetic Aβ leads to a dramatic reduction in the association between Akt and PDK1. The inability of PDK1 to interact with its target Akt led to a decrease in Akt activation and a loss of the subsequent downstream phosphorylations (e.g., GSK3β peptide as in FIGS. 3A and 3C, not shown).

Cell-Based Assay for the Maintenance/Restoration of Akt Signaling.

In some embodiments, cell-based assays may be used to identify candidate compounds that can reduce the Aβ-mediated inhibition of PDK-dependent Akt activation. For example, neuronal cell cultures may be are infected with adeno-Aβ virus, lysed and the contents may be centrifuged into wells with a pre-attached GSK consensus peptide. In these assays, the ability of a candidate compound to restore Akt activation may be evaluated. A non-limiting example of an assay readout is shown in FIG. 3D. In FIG. 3D, total Akt was immunoprecipitated (IP) from $C_2C_{12}$ myotubes that were infected with Adv-Ab/Tet-On virus and then induced or not with doxycycline to express Aβ. One group was treated with insulin to enhance Akt activation. Akt was IP and tested in vitro for its ability to phosphorylate the GSK-3β synthetic substrate. Anti-total and pGSK antibodies are from Cell Signaling.

Accordingly, a cell-based Akt activity assay in the presence or absence of intracellularly expressed Aβ may be used in conjunction or independently of an in vitro assay to evaluate candidate compounds. In some embodiments, the Aβ42 peptide may be expressed from an inducible adenoviral vector (Magrane et al., 2005). In certain embodiments, cells are pretreated with insulin 30 minutes prior to extract preparation in order to increase activated Akt levels Immunoprecipitated Akt may be used in an in vitro kinase assay using the synthetic GSK-3β peptide 'crosstide' as the substrate. As shown in FIG. 3D, extracts from cells that had been induced to express intracellular Aβ showed a marked decrease in levels of activated Akt, as then measured by the inactivating phosphorylation of the synthetic GSK-3β substrate. Note that added total GSK-3β consensus peptide levels are consistent from lane to lane, but that the relative ratio of phosphorylated to total substrate is significantly decreased in the presence of Aβ. However, it should be appreciated that this example is non-limiting and other assays may be used (e.g., with different substrates).

It should be appreciated that in some embodiments other downstream readouts associated with Akt activity also may be used to evaluate the effects of one or more compounds. For example, one or more different metabolic and/or cellular processes may be monitored, including glycogen synthesis, glucose transport, apoptosis suppression, cellular processes such as cell survival, cell growth, cell proliferation, glucose uptake, cell metabolism, protein synthesis, transcription, cell cycle progression, angiogenesis, or any combination of two or more thereof.

Screening Assays

Aspects of the invention may be implemented in any suitable assay format, including, for example, a high throughput assay format. For example, a high throughput screen (HTS) format of more than about 10,000, more than 100,000 (e.g., >110,000) compounds may be used to identify compounds that neutralize the negative effects Aβ has on Akt activation (phosphorylation and activity) and/or Akt association with PDK. In some embodiments, a first screen (e.g., high throughput screens) may be used to identify one or more candidate compounds that have at least a threshold effect on Aβ-mediated inhibition as described herein. In some embodiments, a threshold effect may be a decrease of AP-mediated inhibition of at least 5%, at least 10%, 10-20%, 20-30%, 30-40%, 40-50%, 50-60%, 60-70%, 70-80%, 80-90%, 90-95%, 95%-100% relative to a control level of Aβ-mediated inhibition in the absence of a compound or in the presence of a compound that is known to have little or no effect on Aβ-mediated inhibition. In some embodiments, an assay includes Aβ at a concentration of about 0.1 μM, about 1 μM, or about 5 μM. However, any other suitable higher or lower concentrations may be used. In some embodiments, in order to see a significant reversal of Aβ inhibition (e.g., about 50%), the initial inhibition may be relatively high (e.g., about 40-70%). However, other ranges of inhibition may be used to identify compounds and or dosages of interest.

It should be appreciated that Aβ-mediated inhibition may be assayed with reference to any suitable Aβ-polypeptide (e.g., the major 42 amino acid long pathogenic Aβ1-42 protein, a shorter 40 amino acid long Aβ40 protein, or a longer C99 variant comprising the Aβ42 sequence, a fragment consisting of residues 25-35 of the full length Aβ protein, or the full length APP (wild type or mutated), etc. or any combination thereof. Preferably, the Aβ-polypeptide that is used as a reference is the same Aβ-polypeptide that is used in the screening assay (and the assay conditions, including Aβ-polypeptide concentrations, etc., are the same).

In some embodiments, a candidate compound that is identified in a first screen may be evaluated in a second screen to confirm that its effect on Aβ-mediated inhibition of Akt activation is specific and based on the compound's ability to reduce Aβ-mediated inhibition of the association between Akt and PDK without activating or inactivating Akt in the absence of intracellular Aβ (or without having other non-specific effects, e.g., cancer if too high or AD/schizophrenia/ALS if too low). In some embodiments, one or more of the following assays may be used to assist in the confirmation that a candidate compound has a specific effect. In some embodiments, the effect of the compound may be assayed on PDK-stimulated Akt in the absence of intracellular Aβ. In some embodiments, the effect of the compound may be assayed on Rictor-stimulated Akt. In some embodiments, the effect of the compound may be assayed on PI3K activity. In some embodiments, the effect of the compound may be assayed on other target phosphorylation (e.g., SGK or other kinase targets described herein). In some embodiments, other control assays may be used. For example, reverse or scrambled sequence Aβ peptides may be used (e.g., FIG. 6 controls). In some embodiments, Akt with mutated (deleted) regulatory or kinase domains or PDK with mutant kinase domain (e.g., in the PIF-pocket subdomain) may be used. In some embodiments, other compounds, in place of Aβ, may be used to inhibit the activation (aminopyridines) or stimulate it (e.g., PIFtide) in order to 'set the dynamic range' of the assay (e.g., the extent of GSK phosphorylation). Also, in some embodiments, the effect of ATP or ATP substitutes may be evaluated. The assay should not work in the absence of added ATP (or suitable ATP substitute).

In some embodiments, a cell-based assay for Akt activation may be done in the presence and absence of insulin to specifically stimulate it in order to evaluate the extent to which amyloid knocks it down and the drug restores it.

In some embodiments, the specificity of one or more lead compounds will come from additional individual tests on other kinase reactions. For example, the compound(s) should not interfere with the MAPK: ERK or SAPK, protein kinase A or C, or Wnt signaling pathways activations or activities.

It should be appreciated that after one or more lead compounds are identified, enantiomers and/or stereoisomers may be synthesized evaluated to identify compounds with increased specificity.

It should be appreciated that other controls may include testing the effect of solvents (e.g., DMSO) or other reagents that are present in a compound library. In some embodiments, controls using one or more neutral molecules (e.g., inert compounds) may be used.

Identification of the Site of Action of Intracellular Aβ

Insulin and IGF-I signaling are transduced through tyrosine receptor kinase-mediated activation of p85 PI3K that initiates a cascade of trophic, metabolic and survival events orchestrated by the nodal Ser/Thr kinase, Akt (PDK). Previous studies have shown either reductions in insulin receptor (IR) expression and IR desensitization or tyrosine kinase inactivity in the AD brain (Steen, E., Terry, B. M., Rivera, E. J., Cannon, J. L., Neely, T. R., Tavares, R., Xu, X. J., Wands, J. R., and de la Monte, S. M., 2005, Impaired insulin and insulin-like growth factor expression and signaling mechanisms in Alzheimer's disease—is this type 3 diabetes?, *J Alzheimers Dis* 7:63-80; Frolich, L., Blum-Degen, D., Riederer, P., and Hoyer, S., 1999, A disturbance in the neuronal insulin receptor signal transduction in sporadic Alzheimer's disease, *Ann N Y Acad Sci* 893:290-293; Hoyer, S., 1998, Is sporadic Alzheimer disease the brain type of non-insulin dependent diabetes mellitus? A challenging hypothesis, *J Neural Transm* 105:415-422). Taken with epidemiologic data that type II diabetes and peripheral insulin resistance are risk factors for AD, these observations are consistent with the data that points to down-regulation of insulin signaling and Akt activity as part of the AD condition. Akt deactivation is clearly a major mediator of oxidative and excitotoxic neuronal death (Luo, H. R., Hattori, H., Hossain, M. A., Hester, L., Huang, Y., Lee-Kwon, W., Donowitz, M., Nagata, E., and Snyder, S. H., 2003, Akt as a mediator of cell death, *Proc Natl Acad Sci U S A* 100:11712-11717). However, whether insulin deregulation is a causative factor in AD pathogenesis or a side-show is also debated (Gasparini, L., Netzer, W. J., Greengard, P., and Xu, H., 2002, Does insulin dysfunction play a role in Alzheimer's disease?, *Trends Pharmacol Sci* 23:288-293). Towards an answer to this, the mechanism by which Aβ might deregulate insulin signaling has received little attention.

Intraneuronal β-amyloid (Aβi) accumulates early in Alzheimer's disease (AD) and is regarded to have an important role in pathogenesis. Toxicity ascribed to Aβ has been shown in cultures of skeletal muscle and neuronal cells as well as in transgenic models of human Inclusion Body Myositis and AD. While several organelles, potential receptor molecules, homeostatic processes and signal transduction components have been identified as sensitive to Aβ, a specific step within an essential metabolic or survival pathway has not emerged as a target. Prior studies have implicated the PI3K-Akt signaling cascade. However, the mechanism of inhibition has not until now been assigned to any single step following receptor-insulin interaction, sequential PI3K-PDK-Akt activations and Akt substrate modification. Many recent reports support a view that insulin metabolism is deranged in AD, possibly resulting in failure of energy production and poor survivability to oxidative insults. Against this background the effect of Aβ was tested on each step of the insulin/PI3K signaling cascade. First, in the AD brain, phospho-Akt levels and its activity were decreased relative to control. The association between PDK1 and Akt was diminished in AD brain, where also both immunoprecipitated PDK1 and Akt1 pulled Aβ down. Next, in neuronal and $C_2C_{12}$ myotube cultures, intracellular Aβ expression inhibited both insulin-induced Akt phosphorylation and its activity. In vitro experiments identified that Aβ specifically interrupted the PDK-dependent activation of Akt1 or SGK activity. Aβ oligomers (ADDL) were more toxic to the PDK-dependent activation of Akt1 than monomers. In agreement with these findings, Aβ blocked the association between PDK1 and Akt in both cell extracts and in vitro experiments. Importantly, Aβ did not show any interruption of Akt1 activity itself (once stimulated) or of PI3K activity, nor did it affect other more proximal insulin and PI3K signaling molecules. In control experiments, Aβ did not interrupt PKA or Rictor-dependent Akt1 activities. These results clearly show that Aβ specifically blocks PDK1 activity and the PDK-Akt1 association, and offer a specific target in the search for molecules that neutralize the negative impact of Aβ on critical insulin signaling.

Accordingly, aspects of the invention relate to the discovery of a novel intracellular based mechanism by which Aβi (intracellular or intraneuronal Aβ) mitigates a key metabolic and survival-signaling pathway in neurons and muscle. Akt activation takes place in the submembrane and is dependent on cholesterol and lipid raft structure (Kureishi, Y., Luo, Z., Shiojima, I., Bialik, A., Fulton, D., Lefer, D. J., Sessa, W. C., and Walsh, K., 2000, The HMG-CoA reductase inhibitor simvastatin activates the protein kinase Akt and promotes angiogenesis in normocholesterolemic animals, *Nat Med* 6:1004-1010), where also Aβ generation from APP and secretase endoprotease action is augmented (Gylys, K. H., Fein, J. A., Yang, F., Miller, C. A., and Cole, G. M., 2007, Increased cholesterol in Aβ-positive nerve terminals from Alzheimer's disease cortex, *Neurobiol Aging* 28:8-17; and Simons, M., Keller, P., De Strooper, B., Beyreuther, K., Dotti, C. G., and Simons, K., 1998, Cholesterol depletion inhibits the generation of β-amyloid in hippocampal neurons, *Proc Natl Acad Sci U S A* 95:6460-6464). According to aspects of the invention, a model for local Aβ generation and disruption of the insulin-Akt cell signaling cascade has the expected specificity with respect to the experimental effect of intra versus extracellular compartment-derived Aβ. Thus, when tested on insulin-stimulated myotubes in culture, applied Aβ did not provoke any changes in Akt phosphorylation, Akt activity or levels of activated PDK. Of note, one study gives evidence that extracellular, soluble Aβ experimentally inhibits insulin-IR binding (Xie, L., Helmerhorst, E., Taddei, K., Plewright, B., Van Bronswijk, W., and Martins, R., 2002, Alzheimer's β-amyloid peptides compete for insulin binding to the insulin receptor, *J Neurosci* 22:RC221). The mechanism by which extracellular applied Aβ induces apoptosis in cultured neuronal and non-neuronal cells is probably through activation of cell death pathways and/or inhibition of other protective pathways, such as involving the MAPK family (Magrane, J., Christensen, R. A., Rosen, K. M., Veereshwarayya, V., and Querfurth, H. W., 2006, Dissociation of ERK and Akt signaling in endothelial cell angiogenic responses to beta-amyloid, *Exp Cell Res* 312:996-1010; Pettifer, K. M., Kleywegt, S., Bau, C. J., Ramsbottom, J. D., Vertes, E., Ciccarelli, R., Caciagli, F., Werstiuk, E. S., and Rathbone, M. P., 2004, Guanosine protects SH-SY5Y cells against beta-amyloid-induced apoptosis, *Neuroreport* 15:833-836; Tong, L., Balazs, R., Thornton, P. L., and Cotman, C. W., 2004, β-amyloid peptide at sublethal concentrations downregulates brain-derived neurotrophic factor functions in cultured cortical neurons, *J Neurosci* 24:6799-6809; Watson, K., and Fan, G. H., 2005, Macrophage inflammatory protein 2 inhibits beta-amyloid peptide (1-42)-mediated hippocampal neuronal apoptosis through activation of mitogen-activated protein kinase and phosphatidylinositol 3-kinase signaling pathways, *Mol Pharmacol* 67:757-765; and Wei, W., Wang, X., and Kusiak, J. W., 2002, Signaling events in amyloid beta-peptide-induced neuronal death and insulin-like growth factor I protection, *J Biol Chem* 277:17649-17656).

Accordingly, aspects of the invention relate to screening assays and therapeutic compositions and method related to countering the observed decrease of PDK1 and Akt1 interactions in the AD brain. Aspects of the invention relate to identifying and using compounds that specifically prevent Aβ inhibition of PDK1 association with Akt.

Since Aβ was shown to pull down with either, it is plausible that Aβ interferes with the activation reaction either preventing their association or by promoting their dissociation. A decrease in PDK1 association with Akt was demonstrated in a cell-based Aβ expression assay, as well as when cell extracts were mixed in vitro and synthetic Aβ42 peptide was added. The various extracts used in combinations were derived from resting cells or cells in which Akt was forcibly over expressed. Extracts were further conditioned through immunodepletion of PDK1 or Akt, in order to test interactions between relatively purified samples for either component. Whether it is Akt or PDK1 are initially precipitated, Aβ inhibited their direct interaction in vitro.

To further elucidate the precise mechanism, it was important to show whether or not Aβ peptide could dephosphorylate or deactivate Akt, once it is rendered active by preconditioning cells with insulin before harvest. Experiments showed that Aβ does not dephosphorylate or inactivate Akt, once stimulation has taken place. As a positive control, protein phosphatase 2A (PP2A) exactly reversed Akt activation, proving that Aβ is not acting as an Akt phosphatase. Accordingly, a lipid independent action of intracellular Aβ to inhibit insulin/PI3K signaling involves preventing the activation of Akt by PDK.

The possibility that Aβ could interfere with the PDK-Akt interaction and the completion of activation by inhibiting p85 PI3K function to convert membrane phosphoinositides to 3' phosphorylated second messengers was tested. The addition of more PIP3 did not reverse Aβ inhibition, suggesting but not proving that PIP3 production is not limiting. Therefore, further evidence was sought by directly measuring PI3K activity. Aβ additions had no effect on PIP3 generation, whereas controls consisting of inhibitors LY294002 and phospholipase A2 and PTEN phosphatase all had their expected effects. Although not tested here, it is expected that PIP3 is not limiting in vivo.

Accordingly, without wishing to be bound by theory, aspects of the invention relate to the fact that Aβ binds to Akt and/or PDK1 to prevent or reduce their interaction. However, in some embodiments, Aβ also may have an effect on the interaction between the cellular membranes and the pleckstrin homology domains of the Akt and PDK proteins. It should be noted that the addition of PIP3 to an assay did not overcome the Aβ effect. However, in some embodiments, an effect of Aβ on the PH domains may be detected using a filter assay and/or using PH domain mutants. In some embodiments, Aβ may inhibit the ATP binding site or a nearby catalytic component in the kinase domain of PDK since the activation of another substrate, SGK, was also inhibited (SGK does not have a PH domain like Akt).

Accordingly, aspects of the invention relate to the identification and use of compounds for treating not only Alzheimer's disease, but also other conditions in the PI3K/Akt pathway that are associated with elevated levels of intracellular Aβ.

Signaling through PI3K/Akt accounts for the many pleiotropic effects of insulin and IGF-I on neural tissue, an important piece of which is to protect neurons from oxidative and Aβ stress (Magrane, J., Rosen, K. M., Smith, R. C., Walsh, K., Gouras, G. K., and Querfurth, H. W., 2005, Intraneuronal beta-amyloid expression downregulates the Akt survival pathway and blunts the stress response, *J Neurosci* 25:10960-10969, Luo, H. R., Hattori, H., Hossain, M. A., Hester, L., Huang, Y., Lee-Kwon, W., Donowitz, M., Nagata, E., and Snyder, S. H., 2003, Akt as a mediator of cell death, *Proc Natl Acad Sci U S A* 100:11712-11717, Wei, W., Wang, X., and Kusiak, J. W., 2002, Signaling events in amyloid beta-peptideinduced neuronal death and insulin-like growth factor I protection, *J Biol Chem* 277:17649-17656; Zhao, W., Chen, H., Xu, H., Moore, E., Meiri, N., Quon, M. J., and Alkon, D. L.,1999, Brain insulin receptors and spatial memory, Correlated changes in gene expression, tyrosine phosphorylation, and signaling molecules in the hippocampus of water maze trained rats, *J Biol Chem* 274:34893-34902). Aspects of the invention relate to identifying a specific step in this path as a pharmaco-therapeutic target to arrest the effects of intracellular Aβ accumulation, an early marker of AD pathology (Gouras, G. K., Almeida, C. G., and Takahashi, R. H., 2005, Intraneuronal Abeta accumulation and origin of plaques in Alzheimer's disease, *Neurobiol Aging* 26:1235-1244, Oakley, H., Cole, S. L., Logan, S., Maus, E., Shao, P., Craft, J., Guillozet-Bongaarts, A., Ohno, M., Disterhoft, J., Van Eldik, L., et al., 2006, Intraneuronal beta-amyloid aggregates, neurodegeneration, and neuron loss in transgenic mice with five familial Alzheimer's disease mutations: potential factors in amyloid plaque formation, *J Neurosci* 26:10129-10140, Billings, L. M., Oddo, S., Green, K. N., McGaugh, J. L., and LaFerla, F. M., 2005, Intraneuronal Abeta causes the onset of early Alzheimer's disease-related cognitive deficits in transgenic mice, *Neuron* 45:675-688).

Prevention of resistance to, or destabilization of, insulin signaling in AD and even strategies to upregulate it would have the added beneficial effects to limit cellular Aβ production by reducing γ secretase or promoting IDE activities and transport mechanisms (Ho, L., Qin, W., Pompl, P. N., Xiang, Z., Wang, J., Zhao, Z., Peng, Y., Cambareri, G., Rocher, A., Mobbs, C. V., et al., 2004, Diet-induced insulin resistance promotes amyloidosis in a transgenic mouse model of Alzheimer's disease, *Faseb J* 18:902-904, Carro, E., Trejo, J. L., Gomez-Isla, T., LeRoith, D., and Torres-Aleman, I., 2002, Serum insulin-like growth factor I regulates brain amyloid-beta levels, *Nat Med* 8:1390-1397, Carro, E., Trejo, J. L., Gomez-Isla, T., LeRoith, D., and Torres-Aleman, I., 2002, Serum insulin-like growth factor I regulates brain amyloid-beta levels, *Nat Med* 8:1390-1397, Gasparini, L., Gouras, G. K., Wang, R., Gross, R. S., Beal, M. F., Greengard, P., and Xu, H., 2001, Stimulation of beta-amyloid precursor protein trafficking by insulin reduces intraneuronal beta-amyloid and requires mitogen-activated protein kinase signaling, *J Neurosci* 21:2561-2570, Phiel, C. J., Wilson, C. A., Lee, V. M., and Klein, P. S., 2003, GSK-3alpha regulates production of Alzheimer's disease amyloid-beta peptides, *Nature* 423:435-439). A recent large trial of rosiglitazone, an insulin sensitizer, in mild to moderate AD patients showed cognitive improvement in a subset lacking the cholesterol carrying protein isoform APOE4 (Risner, M. E., Saunders, A. M., Altman, J. F., Ormandy, G. C., Craft, S., Foley, I. M., Zvartau-Hind, M. E., Hosford, D. A., and Roses, A. D., 2006, Efficacy of rosiglitazone in a genetically defined population with mild-to-moderate Alzheimer's disease, *Pharmacogenomics J* 6:246-254). Positive trends were noted in another pilot trial (Watson et al., 2005). Such thiazolidinedione drugs act as PPARγ (peroxisome proliferator-activated receptor gamma) agonists mainly in peripheral adipose tissue, to activate transcription of enzymes of lipid metabolism and enhance organ sensitivity to insulin (Guo, L., and Tabrizchi, R., 2006, Peroxisome proliferator-activated receptor gamma as a drug target in the pathogenesis of insulin resistance, *Pharmacol Ther* 111:145-173). While these modest results are encouraging, aspects of the invention relate to a directly targeted pharmacologic approach to reverse the blockade of PDK1 action, particularly by oligomeric forms of intracellular Aβ (Takahashi, R. H., Almeida, C. G., Kearney, P. F., Yu, F., Lin, M. T., Milner, T. A., and Gouras, G. K., 2004, Oligomerization of Alzheimer's beta-amyloid within processes and synapses of cultured neurons and brain, *J Neurosci* 24:3592-3599).

According to the invention, methods of preventing or reversing Aβ inhibition of the association between PDK1 and Akt may more dramatically improve brain insulin signaling in AD than other approaches being taken. However, it should be appreciated that methods and/or compositions of the invention may be combined with other approaches to treating AD (e.g., other approaches described herein).

It also should be appreciated that aspects of the invention relate to treating other conditions that are associated with Aβ inhibition of the association between PDK1 and Akt.

Compounds:

Aspects of the invention relate to compounds that can counter the Aβ-mediated inhibition of Akt activity. In some aspects, a compound selectively counters the Aβ-mediated inhibition of interactions between PDK1 and Akt. In some embodiments, a compound of the invention does not directly stimulate Akt activation but rather relieves the Aβ-mediated inhibition of PDK-dependent Akt activation.

In some aspects, a compound of the invention binds to a recognition interface between PDK and Akt. In some embodiments, a compound that excludes Aβ but that does not itself bind into the 'PIF' pocket of PDK to prevent the docking of Akt, is desirable and may be termed an 'allosteric' modulator. This means it changes the conformation of the Aβ site at the entrance to the pocket. In some embodiments, a compound of the invention is a peptido-mimetic. Accordingly, a library of peptido-mimetic compounds may be screened according to aspects of the invention (see, for example, compounds described in Yue-Ming, L., et. al., *Nature*, 2000, vol. 405, page 689; compounds described in William Esler: *PNAS*, March 2002, vol. 99, page 2720,—of the gamma secretase inhibitor class—or other libraries of peptido-mimetic compounds). In some embodiments, a peptidomimetic is envisaged with properties similar to the PIFtide (PDK-1 interacting fragment), a 23 residue mimetic of the phosphorylated serine 473 regulatory (HM) domain, that is found to interact with the hydrophobic pocket in the catalytic domain of PDK and activate Akt (phosphorylated T or activation loop of the kinase or a fragment of Akt termed T305tide (Biondi R et al., The EMBO J v21 p4219 2002; and Yang Y, Nature Structural Biology 2002 v9 p940). However, in some embodiments, a lead compound does not constitutively activate Akt or occupy the pocket outside of its desirable property to inhibit the effect of amyloid there. In some embodiments, other mimetics may be found in a drug screen, based for instance on the endogenous 'carboxy-terminal modulator protein' or CTMP sequence which activates Akt at both serine and threonine residues (Ono H Am J. Physiol., Cell Physiol. 2007 v 293 p C1576). In some embodiments, cyclic peptidomimetics may be active in that several alpha-helical, chlorotryptophan-containing or chlorofusin-based mimetics are found to variably inhibit p53 and MDM2 interactions (Fasan, R et al Chembiochem v7 2006 p515). In certain embodiments, small aminopyridine compounds may be active. Certain small aminopyridine compounds with peptide linkages are found to inhibit PDK activity by competitively binding to the ATP pocket, preventing both catalytic phosphorylations of Akt (Feldman R et al JBC 2005 v280 p19867). According to aspects of the invention, this may represent an additional mechanism for intracellular Aβ-mediated inhibition as shown in FIG. 1. Since some of these compounds had no intrinsic inhibitory activity, they may have allosteric properties that are useful in some embodiments of the invention. Similarly, useful compounds may be found that are related to the class of small molecule phosphatidyl inositol (PI) analogues that selectively block activation of Akt without affecting PDK activation per se (Kozikowski A JACS 2003 v125 p 1144). The possibility that Aβ may interfere with the binding of PIP2 or PIP3 to PH domains or in the resulting conformational change of Akt provides a further site of possible action in which many small molecules may be active. In some embodiments, myoinositol compounds (e.g., epi-inositol, sialo-inositol, or related inositol or myoisositol compounds) or derivatives thereof may interfere with the Aβ inhibition of PH domain interactions with membrane components (e.g., by binding to Aβ).

In some embodiments, small molecules may be screened. For example, variants of small molecule inhibitors of PDK1 activity may be screened (e.g., molecules with a single carboxy amide bond and/or amino pyridine compounds) to identify variants that do not inhibit the ATP catalytic site but do inhibit the action of amyloid on the interaction with Akt.

Conditions Associated with Inhibition of PDK-Dependent Akt Activation:

It should be appreciated that any symptoms associated with Aβ-mediated inhibition of Akt activation by PDK1 may be treated according to aspects of the invention. For example, any suitable neural, brain, or other CNS disorder associated with elevated levels of Aβ (e g , Alzheimer's disease) may be treated according to aspects of the invention. For example, inclusion body myositis (IBM) may be treated in some embodiments.

According to aspects of the invention, signaling events downstream of the phosphatidylinositol-3-kinase (PI3K)-Akt (protein kinase B, PKB) axis appear to regulate a vast array of cellular processes from growth and differentiation to cell motility and glucose metabolism to the control of the mitotic cycle and cell death. Recent studies have implicated perturbations in this signaling pathway as playing causal roles in various neurodegenerative disorders including Alzheimer's disease (AD), ALS and Schizophrenia. The expression of intracellular β-amyloid, and its accumulation into toxic oligomeric and fibrillar species in both soluble and insoluble components leads to neuronal and skeletal muscle cell death. Moreover, preceding cell death, the AD Aβ42 peptide inhibits signaling through this pathway.

Accordingly, aspects of the invention relate to identifying and/or using compounds that protect subjects from one or more conditions (e.g., conditions associated with perturbations in one or more Akt signaling pathways) that may result from Aβ inhibition of PDK-dependent activation of Akt. In some embodiments, compositions of the invention may be useful to prevent or slow the development of symptoms associated with one or more such conditions. In certain embodiments, compositions of the invention may be useful to reverse symptoms (e.g., cure) in subjects having one or more such conditions.

The weight of current evidence affirms the central importance of intracellular β-amyloid in causing early neurodegeneration and synaptic loss. According to aspects of the invention, a large part of the loss of cell homeostasis and decrease in viability is caused by the negative effects of intracellular β-amyloid accumulation on Akt signaling. Just upstream of Akt, the phosphoinositide-dependent kinase 1 (PDK1) responds to the lipid products of PI3K signaling by phosphorylating Akt on Thr308. Complete activation of Akt requires autophosphorylation on Ser473. Many targets of activated Akt may be relevant to AD pathogenesis. One such prominent target of Akt kinase activity is glycogen synthase kinase 3β (GSK-3β). When GSK-3β is phosphorylated on Ser9 by Akt, its kinase activity is inhibited. According to aspects of the invention, this is likely to be important in the context of Alzheimer's disease since activated GSK-3β is proapoptotic and is a major tau kinase. In some embodiments, uninhibited GSK-3β may provoke hyperphosphorylation of the microtubule-associated protein tau. Accordingly, aspects of the invention relate to identifying and/or using compounds to treat subjects suffering from neurodegeneration, synaptic loss, or other symtoms associated with the accumulation of intracellular Aβ (e.g., symptoms associated with activated GSK-3β).

Research into AD therapeutics has concentrated on ways to decrease Aβ production (secretase inhibitors) and levels (e.g., ApoE and immune-based removal) or hasten degradation (IDE stimulation) or eliminate fibrillogenesis. However, aspects of the invention relate to identifying specific inhibitors of the negative effect of Aβ on PDK1 interactions with Akt. Aspects of the invention relate to the fact that intracellular, but not extracellular Aβ42 can interfere with the interaction between PDK1 and Akt, and lead to a decrease in Akt activity.

Selection of a Subject for Treatment:

According to some aspects of the invention, a subject may be identified as a candidate for treatment with a composition identified in an assay of the invention if the subject has (or is at risk of developing) one or more symptoms associated with Aβ-mediated inhibition of PDK-dependent activation of Akt (e.g., Alzheimer's disease).

Risk factors for identifying a subject at risk of developing a condition associated with Aβ-mediated inhibition of PDK-dependent activation of Akt include genetic (e.g, ApoE4 genotype) and non-genetic (e.g., mild cognitive impairment (MCI)) factors.

It should be appreciated that aspects of the invention are useful for treating human subjects. However, equivalent therapeutic techniques and compositions may be used in other mammals or experimentally in transgenic animals.

Administration

While it is possible for one or more compounds of the present invention to be administered alone, in some embodiments one or more compounds may be administered as a pharmaceutical formulation (composition) as described herein.

The compounds according to the invention may be formulated for administration in any convenient way for use in human or veterinary medicine, by analogy with other pharmaceuticals.

The invention also relates to a method of making a medicament for use in treating a subject, e.g., a subject that has (or is at risk of developing) one or more symptoms associated with Aβ-mediated inhibition of PDK-dependent activation of Akt (e.g., Alzheimer's disease). Such medicaments can be used for prophylactic treatment of a a subject that has (or is at risk of developing) one or more symptoms associated with Aβ-mediated inhibition of PDK-dependent activation of Akt (e.g., Alzheimer's disease). Accordingly, one or more compounds or compositions described herein that modulate Akt activity as described herein may be used for the preparation of a medicament for use in any of the methods of treatment described herein. In some embodiments, the invention provides for the use of one or more compounds or compositions of the invention (e.g., identified as modulating Aβ-mediated inhibition of PDK-dependent activation of Akt) for the manufacture of a medicament or pharmaceutical for treating a mammal (e.g., a human) having one or more symptoms of, or at risk of developing one or more symptoms associated with Aβ-mediated inhibition of PDK-dependent activation of Akt (e.g., Alzheimer's disease). Accordingly, aspects of the invention relate to the use of one or more compounds or compositions of the invention for the preparation of a medicament for treating or preventing one or more symptoms associated with Aβ-mediated inhibition of PDK-dependent activation of Akt (e.g., Alzheimer's disease).

Accordingly, the invention also relates to one or more compounds or compositions of the invention for use as a medicament. The invention also relates to one or more of these compounds or compositions for use in methods of the invention, for example in methods of inhibiting Aβ-mediated inhibition of PDK-dependent activation of Akt, or of treating or preventing a symptom associated with Aβ-mediated inhibition of PDK-dependent activation of Akt (e.g., Alzheimer's disease).

Compositions of the invention may be administered in effective amounts. An effective amount is a dosage of the composition of the invention sufficient to provide a medically desirable result. An effective amount means that amount necessary to delay the onset of, inhibit the progression of or halt altogether the onset or progression of the particular condition (e.g., one or more symtpoms of Alzheimer's disease) being treated. An effective amount may be an amount that reduces one or more signs or symptoms of the condition (e.g., Alzheimer's disease). When administered to a subject, effective amounts will depend, of course, on the particular condition being treated (e.g., Alzheimer's disease), the severity of the condition, individual subject parameters including age, physical condition, size and weight, concurrent treatment, frequency of treatment, and the mode of administration. These factors are well known to those of ordinary skill in the art and can be addressed with no more than routine experimentation.

It should be appreciated that an effective amount does not need to restore normal levels of Akt activation and/or activity. In some embodiments, an effective amount may be an amount sufficient to reduce the Aβ-mediated inhibition of PDK-dependent activation of Akt, for example, by at least 5%, at least 10%, at least 20%, at least 50%, at least 60%, at least 75%, at least 80%, at least 90%, at least 95% or about 100%. In some embodiments, an effective amount may be an amount sufficient to reduce the Aβ-mediated inhibition of PDK-dependent activation of Akt in a statistically significant manner.

Actual dosage levels of active ingredients in the compositions of the invention can be varied to obtain an amount of the composition of the invention that is effective to achieve the desired therapeutic response for a particular subject, compositions, and mode of administration. The selected dosage level depends upon the activity of the particular composition, the route of administration, the severity of the condition being treated, the condition, and prior medical history of the subject being treated. However, it is within the skill of the art to start doses of the composition at levels lower than required to achieve the desired therapeutic effort and to gradually increase the dosage until the desired effect is achieved. In some embodiments, lower dosages would be required for combinations of multiple compositions than for single compositions.

The compositions of the invention can be administered to a subject by any suitable route. For example, the compositions can be administered orally, including sublingually, rectally, parenterally, intracisternally, intravaginally, intraperitoneally, topically and transdermally (as by powders, ointments, or drops), bucally, or nasally. The term "parenteral" administration as used herein refers to modes of administration other than through the gastrointestinal tract, which include intravenous, intramuscular, intraperitoneal, intrasternal, intramammary, intraocular, retrobulbar, intrapulmonary, intrathecal, subcutaneous and intraarticular injection and infusion. Surgical implantation also is contemplated, including, for example, embedding a composition of the invention in the body such as, for example, in the brain, in the abdominal cavity, under the splenic capsule, brain, or in the cornea.

Compositions of the present invention also can be administered in the form of liposomes. As is known in the art, liposomes generally are derived from phospholipids or other lipid substances. Liposomes are formed by mono- or multilamellar hydrated liquid crystals that are dispersed in an aqueous medium. Any nontoxic, physiologically acceptable, and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic. Methods to form liposomes are known in the art. See, for example, Prescott, Ed., Methods in Cell Biology, Volume XIV, Academic Press, New York, N.Y. (1976), p 33, et seq.

Dosage forms for topical administration of a composition of this invention include powders, sprays, ointments, and inhalants as described herein. The composition is mixed under sterile conditions with a pharmaceutically acceptable carrier and any needed preservatives, buffers, or propellants which may be required. Ophthalmic formulations, eye ointments, powders, and solutions also are contemplated as being within the scope of this invention.

Pharmaceutical compositions of the invention for parenteral injection comprise pharmaceutically acceptable sterile aqueous or nonaqueous solutions, dispersions, suspensions, or emulsions, as well as sterile powders for reconstitution into sterile injectable solutions or dispersions just prior to use. Examples of suitable aqueous and nonaqueous carriers, diluents, solvents, or vehicles include water ethanol, polyols (such as, glycerol, propylene glycol, polyethylene glycol, and the like), and suitable mixtures thereof, vegetable oils (such, as olive oil), and injectable organic esters such as ethyl oleate. Proper fluidity can be maintained, for example, by the use of coating materials such as lecithin, by the maintenance of the required particle size in the case of dispersions, and by the use of surfactants.

In some embodiments, neurodenerative conditions such as conditions affecting the brain may be targeted through conjugation of compounds to nanoparticles. In some embodiments a compound or drug may be targeted to the brain by inserting the compound or drug into a composition such as a wafer and adding it to the brain through surgery.

These compositions also can contain adjuvants such as preservatives, wetting agents, emulsifying agents, and dispersing agents. Prevention of the action of microorganisms can be ensured by the inclusion of various antibacterial and antifungal agents, for example, paraben, chlorobutanol, phenol sorbic acid, and the like. It also may be desirable to include isotonic agents such as sugars, sodium chloride, and the like. Prolonged absorption of the injectable pharmaceutical form can be brought about by the inclusion of agents which delay absorption, such as aluminum monostearate and gelatin.

In some cases, in order to prolong the effect of the composition, it is desirable to slow the absorption of the composition from subcutaneous or intramuscular injection. This result can be accomplished by the use of a liquid suspension of crystalline or amorphous materials with poor water solubility. The rate of absorption of the composition then depends upon its rate of dissolution which, in turn, may depend upon crystal size and crystalline form. Alternatively, delayed absorption of a parenterally administered composition from is accomplished by dissolving or suspending the composition in an oil vehicle.

Injectable depot forms are made by forming microencapsule matrices of the composition in biodegradable polymers such a polylactide-polyglycolide. Depending upon the ratio of composition to polymer and the nature of the particular polymer employed, the rate of composition release can be controlled. Examples of other biodegradable polymers include poly(orthoesters) and poly(anhydrides). Depot injectable formulations also are prepared by entrapping the drug in liposomes or microemulsions which are compatible with body tissue.

The injectable formulations can be sterilized, for example, by filtration through a bacterial- or viral-retaining filter, or by incorporating sterilizing agents in the form of sterile solid compositions which can be dissolved or dispersed in sterile water or other sterile injectable medium just prior to use.

The invention provides methods for oral administration of a pharmaceutical composition of the invention. Oral solid dosage forms are described generally in Remington's Pharmaceutical Sciences, 18th Ed., 1990 (Mack Publishing Co. Easton, Pa. 18042) at Chapter 89. Solid dosage forms for oral administration include capsules, tablets, pills, powders, troches or lozenges, cachets, pellets, and granules. Also, liposomal or proteinoid encapsulation can be used to formulate the present compositions (as, for example, proteinoid microspheres reported in U.S. Pat. No. 4,925,673). Liposomal encapsulation may include liposomes that are derivatized with various polymers (e.g., U.S. Pat. No. 5,013,556). In general, the formulation includes a composition of the invention and inert ingredients which protect against degradation in the stomach and which permit release of the biologically active material in the intestine.

In such solid dosage forms, the composition is mixed with, or chemically modified to include, a least one inert, pharmaceutically acceptable excipient or carrier. The excipient or carrier preferably permits (a) inhibition of proteolysis, and (b) uptake into the blood stream from the stomach or intestine. In one embodiment, the excipient or carrier increases uptake of the composition of the invention, overall stability of the composition and/or circulation time of the composition in the body. Excipients and carriers include, for example, sodium citrate or dicalcium phosphate and/or (a) fillers or extenders such as starches, lactose, sucrose, glucose, cellulose, modified dextrans, mannitol, and silicic acid, as well as inorganic salts such as calcium triphosphate, magnesium carbonate and sodium chloride, and commercially available diluents such as FAST-FLO®, EMDEX®, STA-RX 1500®, EMCOMPRESS® and AVICEL®; (b) binders such as, for example, methylcellulose ethylcellulose, hydroxypropyhnethyl cellulose, carboxymethylcellulose, gums (e.g., alginates, acacia), gelatin, polyvinylpyrrolidone, and sucrose; (c) humectants, such as glycerol; (d) disintegrating agents, such as agar-agar, calcium carbonate, potato or tapioca starch, alginic acid, certain silicates, sodium carbonate, starch including the commercial disintegrant based on starch, EXPLOTAB®, sodium starch glycolate, AMBERLITE®, sodium carboxymethylcellulose, ultramylopectin, gelatin, orange peel, carboxymethyl cellulose, natural sponge, bentonite, insoluble cationic exchange resins, and powdered gums such as agar, karaya or tragacanth; (e) solution retarding agents such a paraffin; (f) absorption accelerators, such as quaternary ammonium compounds and fatty acids including oleic acid, linoleic acid, and linolenic acid; (g) wetting agents, such as, for example, cetyl alcohol and glycerol monosterate, anionic detergent surfactants including sodium lauryl sulfate, dioctyl sodium sulfosuccinate, and dioctyl sodium sulfonate, cationic detergents, such as benzalkonium chloride or benzethonium chloride, nonionic detergents including lauromacrogol 400, polyoxyl 40 stearate, polyoxyethylene hydrogenated castor oil 10, 50 and 60, glycerol monostearate, polysorbate 40, 60, 65, and 80, sucrose fatty acid ester, methyl cellulose and carboxymethyl cellulose; (h) absorbents, such as kaolin and bentonite clay; (i) lubricants, such as talc, calcium sterate, magnesium stearate, solid polyethylene glycols, sodium lauryl sulfate, polytetrafluoroethylene (PTFE), liquid paraffin, vegetable oils, waxes, CARBOWAX® 4000, CARBOWAX® 6000, magnesium lauryl sulfate, and mixtures thereof; (j) glidants that improve the flow properties of the drug during formulation and aid rearrangement during compression that include starch, talc, pyrogenic silica, and hydrated silicoaluminate. In the case of capsules, tablets, and pills, the dosage form also can comprise buffering agents.

Solid compositions of a similar type also can be employed as fillers in soft and hard-filled gelatin capsules, using such excipients as lactose or milk sugar, as well as high molecular weight polyethylene glycols and the like.

The solid dosage forms of tablets, dragees, capsules, pills, and granules can be prepared with coatings and shells, such as enteric coatings and other coatings well known in the pharmaceutical formulating art. They optionally can contain opacifying agents and also can be of a composition that they release the active ingredients(s) only, or preferentially, in a part of the intestinal tract, optionally, in a delayed manner. Exemplary materials include polymers having pH sensitive solubility, such as the materials available as EUDRAGIT®. Examples of embedding compositions which can be used include polymeric substances and waxes.

The composition of the invention also can be in microencapsulated form, if appropriate, with one or more of the above-mentioned excipients.

Liquid dosage forms for oral administration include pharmaceutically acceptable emulsions, solutions, suspensions, syrups, and elixirs. In addition to the composition of the invention, the liquid dosage forms can contain inert diluents commonly used in the art, such as, for example, water or other solvents, solubilizing agents and emulsifiers, such as ethyl alcohol, isopropyl alcohol ethyl carbonate ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydroflirfuryl alcohol, polyethylene glycols, fatty acid esters of sorbitan, and mixtures thereof.

Besides inert diluents, the oral compositions also can include adjuvants, such as wetting agents, emulsifying and suspending agents, sweetening, coloring, flavoring, and perfuming agents. Oral compositions can be formulated and further contain an edible product, such as a beverage.

Suspensions, in addition to the composition of the invention, can contain suspending agents such as, for example ethoxylated isostearyl alcohols, polyoxyethylene sorbitol and sorbitan esters, microcrystalline cellulose, aluminum metahydroxide, bentonite, agar-agar, tragacanth, and mixtures thereof.

Also contemplated herein is pulmonary delivery of the composition of the invention. The composition is delivered to the lungs of a mammal while inhaling, thereby promoting the traversal of the lung epithelial lining to the blood stream. See, Adjei et al., *Pharmaceutical Research* 7:565-569, 1990, Adjei et al., *International Journal of Pharmaceutics* 63:135-144, 1990, (leuprolide acetate), Braquet et al., *Journal of Cardiovascular Pharmacology* 13 (suppl.5): s.143-146, 1989, (endothelin-1), Hubbard et al., *Annals of Internal Medicine* 3:206-212, 1989, ($\alpha$1-antitrypsin, Smith et al., *J. Clin. Invest.* 84:1145-1146, 1989, ($\alpha$1-proteinase), Oswein et al., "Aerosolization of Proteins," Proceedings of Symposium on Respiratory Drug Delivery II, Keystone, Colo., March, 1990, (recombinant human growth hormone), Debs et al., *The Journal of Immunology* 140:3482-3488, 1988, (interferon-$\gamma$ and tumor necrosis factor $\alpha$), and Platz et al., U.S. Pat. No. 5,284,656 (granulocyte colony stimulating factor).

Contemplated for use in the practice of this invention are a wide range of mechanical devices designed for pulmonary delivery of therapeutic products, including, but not limited to, nebulizers, metered dose inhalers, and powder inhalers, all of which are familiar to those skilled in the art.

Some specific examples of commercially available devices suitable for the practice of the invention are the ULTRAVENT® nebulizer, manufactured by Mallinckrodt, Inc., St. Louis, Mo.; the ACORN II® nebulizer, manufactured by Marquest Medical Products, Englewood, Colo.; the VENTOL® metered dose inhaler, manufactured by Glaxo Inc., Research Triangle Park, N.C.; and the SPINHALER® powder inhaler, manufactured by Fisons Corp., Bedford, Mass.

All such devices require the use of formulations suitable for the dispensing of a composition of the invention. Typically, each formulation is specific to the type of device employed and can involve the use of an appropriate propellant material, in addition to diluents, adjuvants, and/or carriers useful in therapy.

The composition is prepared in particulate form, preferably with an average particle size of less than 10 μm, and most preferably 0.5 to 5 μm, for most effective delivery to the distal lung.

Carriers include carbohydrates such as trehalose, mannitol, xylitol, sucrose, lactose, and sorbitol. Other ingredients for use in formulations may include lipids, such as DPPC, DOPE, DSPC and DOPC, natural or synthetic surfactants, polyethylene glycol (even apart from its use in derivatizing the inhibitor itself), dextrans, such as cyclodextran, bile salts, and other related enhancers, cellulose and cellulose derivatives, and amino acids.

Also, the use of liposomes, microcapsules or microspheres, inclusion complexes, or other types of carriers is contemplated.

Formulations suitable for use with a nebulizer, either jet or ultrasonic, typically comprise a composition of the invention dissolved in water at a concentration of about 0.1 to 25 mg of biologically active protein per mL of solution. The formulation also can include a buffer and a simple sugar (e.g., for protein stabilization and regulation of osmotic pressure). The nebulizer formulation also can contain a surfactant to reduce or prevent surface-induced aggregation of the inhibitor composition caused by atomization of the solution in forming the aerosol.

Formulations for use with a metered-dose inhaler device generally comprise a finely divided powder containing the composition of the invention suspended in a propellant with the aid of a surfactant. The propellant can be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid also can be useful as a surfactant.

Formulations for dispensing from a powder inhaler device comprise a finely divided dry powder containing the composition of the invention and also can include a bulking agent, such as lactose, sorbitol, sucrose, mannitol, trehalose, or xylitol, in amounts which facilitate dispersal of the powder from the device, e.g., 50 to 90% by weight of the formulation.

Nasal delivery of the composition of the invention also is contemplated. Nasal delivery allows the passage of the composition to the blood stream directly after administering the therapeutic product to the nose, without the necessity for deposition of the product in the lung. Formulations for nasal delivery include those with dextran or cyclodextran. Delivery via transport across other mucous membranes also is contemplated.

Compositions for rectal or vaginal administration are preferably suppositories which can be prepared by mixing the composition of the invention with suitable nonirritating excipients or carriers, such as cocoa butter, polyethylene glycol, or suppository wax, which are solid at room temperature, but liquid at body temperature, and therefore melt in the rectum or vaginal cavity and release the active compound.

In order to facilitate delivery of the composition of the invention across cell and/or nuclear membranes, compositions of relatively high hybrophobicity are preferred. The composition of the invention can be modified in a manner which increases hydrophobicity, or the composition of the invention can be encapsulated in hydrophobic carriers or solutions which result in increased hydrophobicity.

The term "treatment" or "treating" is intended to relate to prophylaxis, amelioration, prevention and/or cure of a condition (e.g., Alzheimer's disease). Treatment after a condition (e g , Alzheimer's disease) that has started aims to reduce, ameliorate or altogether eliminate the condition, and/or its associated symptoms, or prevent it from becoming worse. Treatment of subjects before a condition (e.g., Alzheimer's disease) has started (i.e., prophylactic treatment) aims to reduce the risk of developing the condition and/or lessen its severity if the condition does develop. As used herein, the term "prevent" refers to the prophylactic treatment of a subject who is at risk of developing a condition (e g , Alzheimer's disease) resulting in a decrease in the probability that the subject will develop the disorder, and to the inhibition of further development of an already established disorder.

EXAMPLES

Aspects of the invention are illustrated by the following non-limiting examples.

Example 1

Experimental Procedures

Human Brain Samples

Rapidly frozen control and Braak stage II human brain samples from temporal or frontal cortex were generously provided by the Harvard Brain Tissue Resource Center, McLean Hospital (Belmont, Mass.). Postmortem intervals ranged from 5 to 10 hours.

Cell Culture and Reagents

Mouse $C_2C_{12}$ cells (American Type Culture Collection, Manassas, Va.; CRL-1772) were grown in Dulbecco's modified Eagle medium (DMEM), 20% fetal bovine serum (FBS) (Invitrogen, Carlsbad, Calif.), and maintained for passage at or below 60% confluence. To induce differentiation, cultures that had reached greater than 90% confluence were switched to differentiation medium (DM) consisting of DMEM, 2% adult horse serum. Neuronal-like SH-SY5Y, HEK-293, and NIH/3T3 cells were grown in DMEM, 10% FBS, and maintained for passage at or below 80% confluence. However, it should be appreciated that other cell lines may be used (e.g., PC12 cells, N2A cells, primary cortical neurons, various stable transfected cell lines, etc.). It also should be appreciated that these and/or any other cell lines described herein in the context of the examples also may be used in the context of any in vivo assay described above in the summary or detailed description.

Recombinant Phosphatase and Tensin Homolog (PTEN; R & D Systems, Minneapolis, Minn.), purified PP2A from human erythrocytes (Upstate, Temecula, Calif.), and purified c-AMP-dependent protein kinase A (PKA, Promega) from bovine heart were stored at −20 and used freshly. PKA inhibitor (PKI, Biosource) and PI3K inhibitor, LY294002 (Cell Signaling) were diluted to 20 or 10 μM in kinase buffer. Antibodies used were: anti-cdk4 (polyclonal), Akt, Actin (polyclonal), and IRa (polyclonal) (Santa Cruz); p-Akt (polyclonal; Ser473 and Thr308), p-GSK-3α/0 (polyclonal; Ser21/9), GSK-30 (polyclonal), IRP (monoclonal), p-Tyrosine (monoclonal), and p-PDK (polyclonal, Ser241) (Cell Signaling, Danvers, Mass.); IRS-1 (monoclonal) and PDK (monoclonal) (BD Biosciences); PI3K (polyclonal, p85) and SGK (polyclonal) (Upstate, Temecula, Calif.); Rictor (polyclonal) (Bethyl Laboratories, Montgomery, Tex.); 6E10 (monoclonal; Covance Co.); R1282 (polyclonal; gift from Dr. Selkoe's lab). Phospholipase A2 (PLA2) was from Sigma. The lipids phosphatidylinositol-tris-3,4,5-phosphate, dipalmitoyl, (PIP3) (Matreya LLC, Pleasant Gap, Pa.), and D-myo-Phosphatidylinositol (PtdIns; PI) (Echelon, Salt Lake City, Utah) were diluted into water or CHCl3:MeOH:H2O (1:2:0.8), aliquoted into 100 μg vials and stored at −20° C. ATP (Cell Signaling), radioactive ATP ([γ-32P]ATP) (300 μCi/ml) (PerkinElmer, Boston, Mass.), and thin-layer chromatography (TLC) silica gel plate (#105553, Merck Co.) coated with potassium oxalate (Sigma Co.) were used in the PI3K activity assay as given below. The GSK-3 consensus phosphorylation site-containing peptide (GSK-3α/0 (Ser21/9) (CGPKGPGRRGRRRTSSFAEG) fused to the N-terminus of paramyosin) (Cell Signaling) was stored at 1 mg/ml until use.

Infection of $C_2C_{12}$ Myotubes with Adenoviruses

Adv Tet-On and Adv TRE-Aβ42 viruses have been described previously (94). Adv WT-Akt, expressing wild-type Akt was described previously (95). $C_2C_{12}$ were grown to 80-90% confluence in DMEM:20% FBS. Following the switch to DM at day 3 the early myotubes were infected with Adv A[i/TetOn (4:1 ratio) for 24~36 hr before washing and then induced with doxycycline (1 μg/ml) for an additional 24~36 hr. Some cultures were infected with Adv WT-Akt for 48 hr, washed with phosphate buffered saline (PBS) and then harvested. Cell lysates expressing Aβ or Akt were harvested by adding lysis buffer [20 mM Tris (pH 7.5), 150 mM NaCl, 1 mM EDTA, 1 mM Na3VO4, 1% NP-40, 10% Glycerol, 1 mM Sodium Pyrophosphate, 1 μg/ml Leupeptin, 1 μg/ml Pepstatin A, 1 µg/ml Aprotinin, 0.1 mM PMSF]. Cell extracts were stored at −80° C. until use.

Cell Viability $C_2C_{12}$ were grown in 8-chamber slides (Nalge-NUNC) in DMEM:20% FBS. Three days following the switch to DM, the early myotubes were infected with Adv Ali/TetOn and induced as before. Cell profiles were quantified after image capture using a Nikon TE200 microscope (10×) with Hoffman modulation optics and coupled with a SPOT cooled CCD camera and imaging software. The thickness and the length of all myotubes, in each of 5 random fields were measured. The cells were fixed using 4% paraformaldehyde in PB and incubated with bis-benzimide (Hoechst 33258) for 15 minutes at 25° C. After mounting in N-propylgallate, nuclear pyknosis was quantified by manual counting through a Nikon Diaphot epifluorescence microscope.

Aβ, ADDL and Fibril Preparation

Aβ peptides were obtained from BioSource (Camarillo, Calif.) as dried TFA (trifluoroacetic acid) salts. The scrambled Aβ42 sequence peptide was from rPeptide (Athens, Ga.). The Aβ peptides were solubilized in 5% dimethyl sulfoxide (DMSO); 25 mM Tris-HCl, pH 7.4, aliquoted and immediately stored frozen at −80° C. Ali-derived diffusible ligands (ADDL) were prepared according to Lambert et al. (Lambert, M. P., Barlow, A. K., Chromy, B. A., Edwards, C., Freed, R., Liosatos, M., Morgan, T. E., Rozovsky, I., Trommer, B., Viola, K. L., et al., 1998, Diffusible, nonfibrillar ligands derived from Abeta1-42 are potent central nervous system neurotoxins, *Proc Natl Acad Sci USA* 95:6448-6453) and Klein et al. (Klein, W. L., 2002, Abeta toxicity in Alzheimer's disease: globular oligomers (ADDLs) as new vaccine and drug targets, *Neurochem Int* 41:345-352). Briefly, Aβ peptide was dissolved in 1,1,1,3,3,3-hexafluoro-2-propanol (HFIP, Sigma H-8508) and evaporated on a Speedvac. The Aβ film was resuspended in 100% anhydrous DMSO. It was then diluted to 5 mM in F12 medium lacking phenol red (BioSource Inc.). The peptide solution was incubated at 4° C. for 24 to 48 hr. Following the incubation and centrifugation at 14,000 g for 10 min at 4° C., the supernatant containing ADDL-enriched Aβ was transferred to a new tube. Both fibrillar and ADDL preparations were stored frozen at −80° C. until use. Fibrillar Aβ was made by diluting Aβ42 in DMSO to 100 µM in 10 mM HCl, immediate vortexing for 30 s, and incubation at 37° C. for 24 hr (Stine, W. B., Jr., Dahlgren, K. N., Krafft, G. A., and LaDu, M. J., 2003, In vitro characterization of conditions for amyloid-beta peptide oligomerization and fibrillogenesis, *J Biol Chem* 278:11612-11622).

Thioflavin T Fluorescence Assay

Fibril-enriched preparations of Aβ were verified according to Conway et al. (Conway, K. A., Lee, S. J., Rochet, J. C., Ding, T. T., Williamson, R. E., and Lansbury, P. T., Jr., 2000, Acceleration of oligomerization, not fibrillization, is a shared property of both alpha-synuclein mutations linked to early-onset Parkinson's disease: implications for pathogenesis and therapy, *Proc Natl Acad Sci U S A* 97:571-576). 100 µM Thioflavin T (ThT) (Sigma) was filtered through a 0.22 micron filter unit (Nalge NUNC Inc.). To construct a standard curve, 90 µl of each Aβ sample (0, 0.5, 1, 2, 4 µg) was added to 100 µl glycine-NaOH (pH 8.5) solution, to which 10 µl ThT solution was added to a total volume of 200 µl per well in a C96 White Maxisorp plate (Nalge NUNC Co.). After mixing, fluorescence at 508 nm was measured with a CytoFluor Multi-Well plate reader (excitation at 450 nm, bandwidth 50; emission at 508 nm, bandwidth 20) (Perseptive Biosystems Co.).

Immunoprecipitations and Western Blot Analysis

Cells were lysed in NP-40 lysis buffer containing Tris-HCl (pH 7.5, 20 mM), NaCl (150 mM), 1 mM EDTA, Na4P2O7 (1 mM), Na3VO4 (1 mM), 1% NP-40, 10% Glycerol, 1 µg/ml Leupeptin, 1 µg/ml Pepstatin A, 1 µg/ml Aprotinin, 0.1 mM phenylmethylsulfonyl fluoride (PMSF) and protease inhibitor cocktail (Complete; Roche Biochemicals, Indianapolis, Ind., USA) incubated on ice for 10 min, and then centrifuged at 14,000 g for 10 min. Immunoprecipitations (IPs) were performed using 100-300 µg of extract protein. Extracts were incubated overnight at 4° C. with 2~3 µg of primary antibody, followed by the addition of Protein G Sepharose and an additional incubation at 4° C. for 1.5 hr. Immunoprecipitates were harvested by centrifugation at 5000 g for 1 min at 4° C. and washed 2~3 times with phosphate buffered saline (PBS) buffer containing 0.5% NP-40 and 0.1 mM Na3VO4. For direct western blot analysis, sample buffer was simply added. For kinase and phosphatase reactions, the samples were washed 2 more times. Whole-cell extract supernatants were used directly for western blot analysis (20~30 µg for cell cultures or 60~80 µg for human sample).

Protein from cell extracts in the lysis buffer or immunoprecipitates were heated (90~100° C., 10 min) in Laemmli sample buffer, cleared by centrifugation, separated on SDS-PAGE and then transferred onto PVDF membrane (Immobilon-P; Millipore, Bedford, Mass., USA). Membranes were blocked using TBS containing 0.3% Tween-20 and 5% (wt/vol) non-fat dry milk. After incubation with primary antibodies (1:500-2000 dilution) for 18 hr at 4° C. in buffer containing 5% BSA and 0.05% NaN3, blots were washed, re-incubated in HRP-conjugated secondary antibodies (1:2000 dilution; Cell Signaling), washed again and the signals detected using enhanced chemiluminescence reagents and film from GE Healthcare. Signal intensity was quantified using a Kodak Image Station 4000R (Kodak Co.).

Akt1 Activity Assay

Akt1 was immunoprecipitated (IP) overnight from 100 µg of the human brain sample or from $C_2C_{12}$ myotubes infected with adenovirus encoding Aβ using a 1:100 dilution of goat anti-Akt1 antibody. The following morning, 40 µl of a 50% slurry of protein G-Agarose (PGA) (Roche Applied Science) was added for an additional 1.5 hours. The beads were washed twice with wash buffer [1× phosphate buffered saline (PBS), 0.5% NP-40, 0.1 mM Na3VO4] and twice with kinase buffer [25 mM Tris (pH 7.5), 2 mM DTT, 0.1 mM Na3VO4, 10 mM MgCl2]. ATP (200 µM) and GSK-3 fusion protein (1 µg/50 µl) were added in the presence of kinase buffer, and the final reaction (50 µl) was incubated 30 minutes at 30° C. The reaction was stopped by adding 40 µl of Laemmli buffer. 20 µl of sample was loaded onto a 10% polyacrylamide gel for fractionation and western detection development.

In Vitro p-Akt and Activity Levels

Immunoprecipitates (IPs) of PDK1 and Akt were prepared from 100 µg of either SH-SY5Y, $C_2C_{12}$ myotubes or from insulin-treated cultures. ATP (200 µM), GSK-3 fusion protein (1 µg/50 µl) and kinase buffer were added to the reaction. Various Aβ peptides were finally added at 0.01, 0.1, 1, 5, 10, 20 µM. Akt activity level was otherwise determined as above.

PDK and Akt1 Interaction Assay

For cell-based interaction studies, intracellular Aβ42 production was induced by infecting $C_2C_{12}$ myotubes with Adv Aβ/TetOn. These cell extracts (100 µg) were used to IP endogenous Akt, and from this pull-down, determine the levels of associated PDK by western blot. The in vitro interaction study involved first enriching for Akt through viral-mediated expression of WT-Akt. Akt-enriched/PDK-depleted extract was then prepared by removing the PDK, via immunoprecipitation, from the Akt-enriched cell extract. Akt-depleted extracts were prepared from control extracts by pre-immunoprecipitating Akt. These were relatively enriched with endogenous PDK. The enrichments and depletions were confirmed by western blot analysis. The interaction assay contained a mixture of 100 µg Akt-enriched and 100 µg control cell extract in the presence or absence of Aβ42 (up to 10 µM). The mixtures were incubated for 30 minutes at 30° C., followed by overnight incubation at 4° C. with goat anti-Akt1. Protein G beads were added with mixing for 1.5 hr. PDK1 and Akt1 levels were determined by western blot. In control experiments, 100 µg of Akt-enriched, PDK-depleted extract and 100 µg of a control extract depleted for Akt were mixed in the presence or absence of Aβ42 (up to 5 µM) and subjected to the same analyses.

PI3K Activity Assay

PI3K was immunoprecipitated (IP) from the NIH/3T3 cell lysates with rabbit anti-p85 subunit (Upstate). The IPs were washed twice with cold phosphate buffered saline (PBS) buffer containing 0.5% NP-40 and 0.1 mM Na3VO4, and then twice with THE buffer [Tris.HCl pH7.4 20 mM, NaCl 100 mM, EGTA 0.5 mM]. PI3K activity was determined by incubating the beads with kinase buffer [6.5 mM HEPES (pH 7.4), 10 mM MgCl$_2$] with 50 µM ATP, 2 µCi [y-32P] ATP, 4 µg of 3-sn-Phosphatidyl-L-serine (PS) and 2 µg of D-myo-Phosphatidylinositol (PtdIns; PI) (Echelon, Salt Lake City, Utah) for 10 min at room temperature. The reactions were stopped by adding 50 µl of 4N HCl. Phospholipids were extracted using 100 µl of CHCl$_3$/methanol (1:1). Phosphorylated products were separated by TLC as described previously (Whitman, M., Kaplan, D. R., Schaffhausen, B., Cantley, L., and Roberts, T. M., 1985, Association of phosphatidylinositol kinase activity with polyoma middle-T competent for transformation, *Nature* 315:239-242). The conversion of PI to PI3P was detected and quantified using a Storm Phosphorimager (GE Healthcare).

Example 2

Akt Deactivation and PDK-Akt Dissociation in AD Brain

Figure 4A:
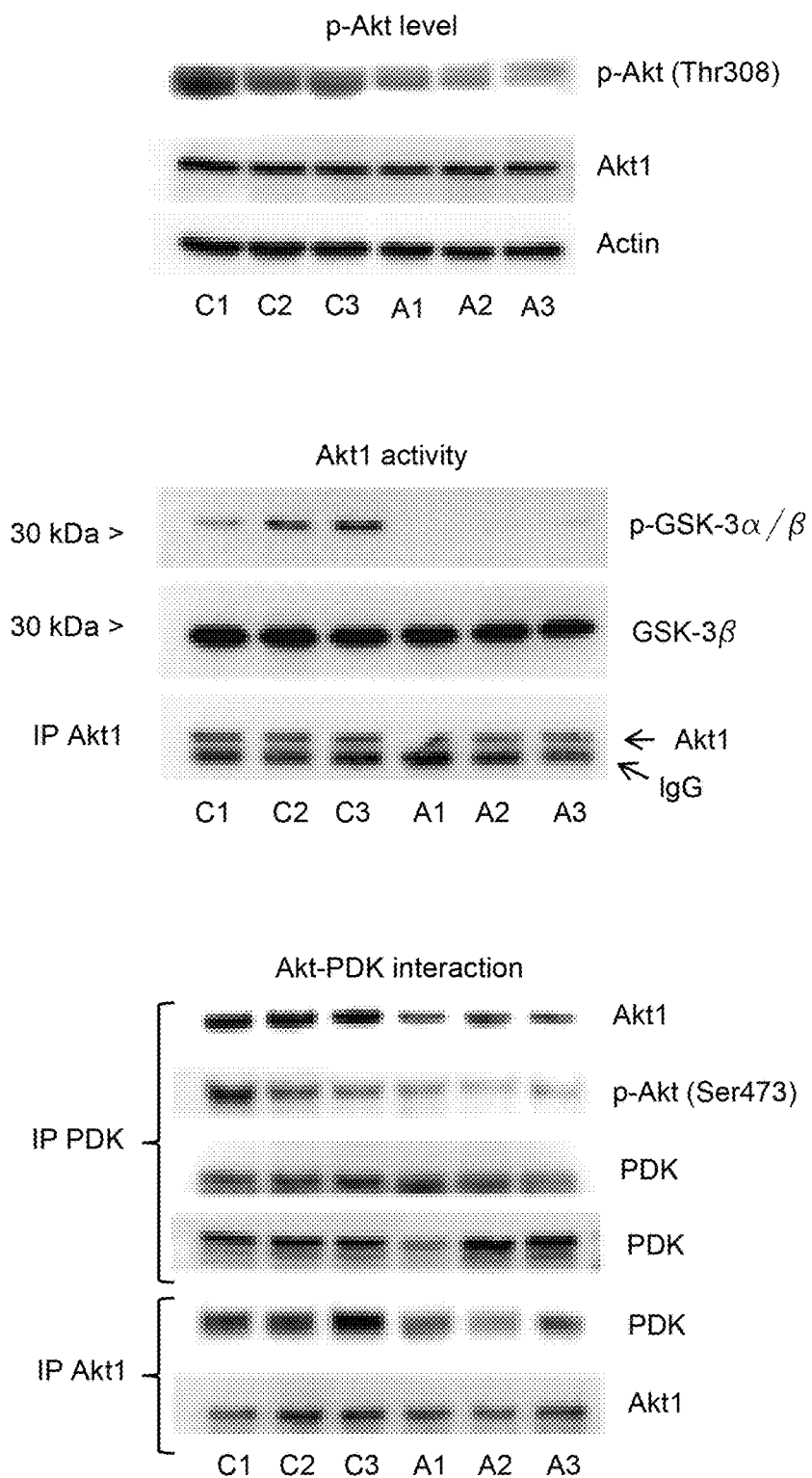
FIGS. 4A-4C illustrate Akt activity and decreased association with PDK in AD Brain—(Control brain: C1-3; AD brain: A1-3)
Figure 4B:
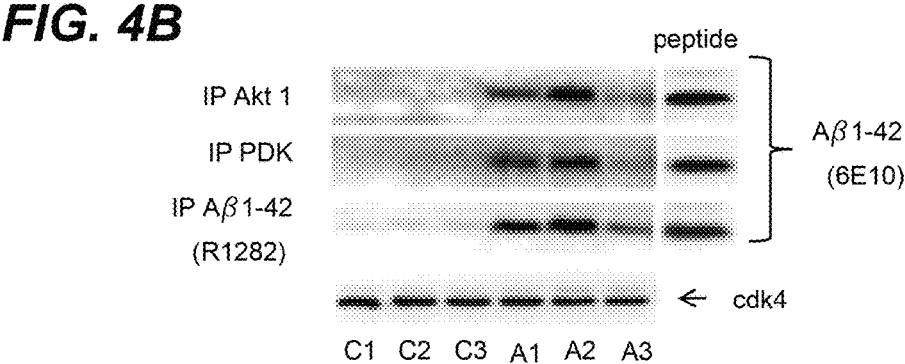

Levels of Akt phosphorylation, indicating activation, Akt activity itself and the degree to which a kinase partly responsible for Akt activation (Thr308 phosphorylation, PDK1), is physically associated with Akt in human AD brain, were determined In the AD brain, p-Akt (Thr308) levels were decreased (FIG. 4A top). Levels of total Akt1 and actin, used here as control, were unchanged between AD and matched normal brain samples (FIG. 4A top). To confirm down-regulation of Akt1 activity in the AD brain, 100 µg of brain protein was used to immunoprecipitate (IP) Aka in a substrate phosphorylation assay. Akt1 activity, judged by the level to which a GSK-3β consensus peptide was phosphorylated at Ser 9, was found to be decreased in AD brain samples relative to controls (FIG. 4A middle). The interaction between PDK1 and Akt1 was tested in pull-downs from brain extract. In this experiment, both total Akt and p-Akt (Ser473) were tested in pull-downs of PDK. The IP was developed for Ser473 phosphorylation because it is required for full Akt activity and dependently follows the Thr308 phosphorylation of the catalytic domain by PDK-1 (Toker, A., and Newton, A. C., 2000, Akt/protein kinase B is regulated by autophosphorylation at the hypothetical PDK-2 site, *J Biol Chem* 275:8271-8274, Alessi, D. R., Andjelkovic, M., Caudwell, B., Cron, P., Morrice, N., Cohen, P., and Hemmings, B. A., 1996, Mechanism of activation of protein kinase B by insulin and IGF-1, *Embo J* 15:6541-6551, and Alessi, D. R., and Cohen, P., 1998, Mechanism of activation and function of protein kinase B, *Curr Opin Genet Dev* 8:55-62). In agreement with the above, this interaction level was decreased in the AD brain (FIG. 4A bottom). Both PDK1 pull-down of total and p-Akt and Akt1 pull-down of total PDK1 were lessened in AD temporal lobe samples. All immunoprecipitated levels of PDK1 or Akt1 were near constant between the samples, as in general, were directly determined levels of PDK1 and Akt in whole brain extracts (input).

Figure 4C:
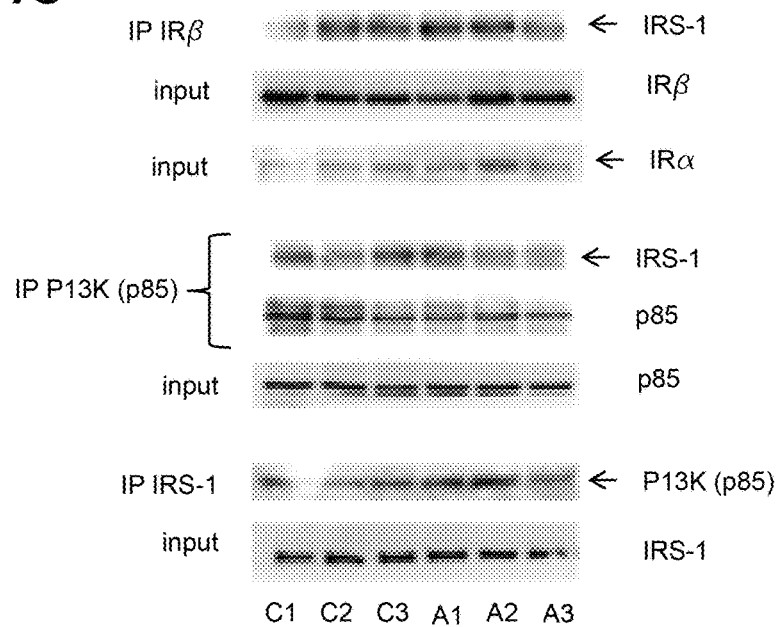

One possibility for the downregulation of Akt activation in AD brain was direct inhibition by increased cellular β-amyloid (βR). Aβ levels were found by IP to be greatly increased in the AD brain samples (FIG. 4B). More interestingly, the association of Aβ with each of Akt1 and PDK1 was increased in the AD brain. The proximal insulin-dependent PI3K pathway steps were also investigated for any changes in protein levels or interaction in the same AD samples (FIG. 4C). The insulin receptor (IR) and β (IRβ) subunit levels were unchanged in AD compared to control brain (FIG. 4C top, input). The PI3 kinase (PI3K) regulatory subunit, p85 did not appear differentially expressed in AD (FIG. 4C middle, input), nor did the insulin receptor substrate 1 (IRS-1) scaffold protein (FIG. 4C bottom, input). The interactions between IRP and IRS-1, as well as PI3K (p85 regulatory subunit) with IRS-1 were also not significantly different between AD and control brain samples (FIG. 4C, IP: IRP, IRS-1, PI3K).

In FIG. 4A, the top panels show that levels of activated Akt (p-Akt-Thr308) are decreased in AD brain samples. 80 µg of whole brain protein were loaded per lane. The middle panels show Akt activity from AD and control brain assayed in vitro. 100 µg of protein was used as starting material for immunoprecipitation (IP) of total Akt. The substrate, a synthetic GSK-3β/paramyosin fusion protein, was less phosphorylated by AD brain samples. The bottom panels show Akt and PDK1 interaction studies in AD brain. PDK1 and total Akt1 immunoprecipitations were resolved by gel electrophoresis and developed for the association with Akt1 or pS473-Akt and PDK1 respectively. Densitometric analysis of pAkt to total Akt ratios and the association between Akt1 and PDK1 defined reductions in all AD brain samples.

In FIG. 4B, 75 µg total protein in brain lysates was immunoprecipitated. Western blots were probed with MAb 6E10 versus human Aβ1-42. Synthetic Aβ peptide (50 ng) is shown as a standard. cdk4 Western blot demonstrates equal starting material.

In FIG. 4C, the immunoblot indicate no significant difference in the expression of these insulin-signaling constituents. 80 µg of extract protein was fractionated and examined for IRα, IRβ, IRS-1 and the p85 subunit of PI3K. IP of 100 µg of extract protein for the p85 subunit of PI3K showed no change in its association with IRS-1. The reverse IP using IRS-1 gave similar results.

In summary, levels of activated (phospho)-Akt and Akt activity were investigated in human AD and control brain samples. In AD temporal cortex, p-Akt (Thr308) levels were decreased. To confirm this, Aka activity was shown to be decreased in the same AD brain specimens. These results are consistent with other evidence to support the concept that Alzheimer's disease is a multifaceted insulin resistance state (Hoyer, S., 2002, The brain insulin signal transduction system and sporadic (type II) Alzheimer disease: an update, *J Neural Transm* 109:341-360, Craft, S., and Watson, G. S, 2004, Insulin and neurodegenerative disease: shared and specific mechanisms, *Lancet Neurol* 3:169-178; and de la Monte, S. M., and Wands, J. R., 2005, Review of insulin and insulin-like growth factor expression, signaling, and malfunction in the central nervous system: relevance to Alzheimer's disease, *J Alzheimers Dis* 7:45-61). On this point however, there are some studies indicating different or opposite results. In AD temporal cortex, Griffin et al. (Griffin, R. J., Moloney, A., Kelliher, M., Johnston, J. A., Ravid, R., Dockery, P., O'Connor, R., and O'Neill, C., 2005, Activation of Akt/PKB, increased phosphorylation of Akt substrates and loss and altered distribution of Akt and PTEN are features of Alzheimer's disease pathology, *J Neurochem* 93:105-117) showed that p-Akt (Ser473) levels were significantly increased in particulate fractions, and moderately decreased in cytosolic fractions relative to total Immunohistochemical levels of p-Akt (Ser473) were depleted in cytosolic areas of neurons in the entorhinal cortex and hippocampal CA1 region. Although Akt substrates were examined, no activity assay was reported, Rickle et al. (Rickle, A., Bogdanovic, N., Volkman, I., Winblad, B., Ravid, R., and Cowburn, R. F., 2004, Akt activity in Alzheimer's disease and other neurodegenerative disorders, *Neuroreport* 15:955-959) examined Akt enzyme activities and found them to be generally higher than control, but the amount of Akt precipitated was highly variable between cases. Lastly, Pei et al. (Pei, J. J., Khatoon, S., An, W. L., Nordlinder, M., Tanaka, T., Braak, H., Tsujio, I., Takeda, M., Alafuzoff, I., Winblad, B., et al., 2003, Role of protein kinase B in Alzheimer's neurofibrillary pathology, *Acta Neuropathol* (Berl) 105:381-392) showed that p-Akt (Thr308) levels were increased in the frontal cortex of AD patients compared with normal and Huntington's disease controls however, total Akt levels were not given. The reason for the opposing results described herein in contrast with some of these studies may be related to the use of total brain lysate reported herein as well as other methodological differences such as postmortem interval and oxidation status of the tissue. Nevertheless, the present results are most consistent with Steen et al. (Steen, E., Terry, B. M., Rivera, E. J., Cannon, J. L., Neely, T. R., Tavares, R., Xu, X. J., Wands, J. R., and de la Monte, S. M., 2005, Impaired insulin and insulin-like growth factor expression and signaling mechanisms in Alzheimer's disease—is this type 3 diabetes?, *J Alzheimers Dis* 7:63-80) who also show reductions in p-Akt and p-GSK-3 levels relative to total protein levels in AD vs control brain samples.

In order to validate these findings in AD brain, Akt and PDK1 interaction were shown to be decreased in AD compared to normal brain (FIG. 4A). Moreover, Aβ may be directly involved in preventing Akt from associating with PDK, since endogenous Aβ levels in AD brain appear to bind both kinases (FIG. 4B).

AD brain samples were evaluated for other evidence of insulin signaling abnormalities in the interactions between the more proximal components to the final activation of Akt. No major changes were found in the binding of IRS-1 to the IR homo dimer subunits nor in their expression levels. The same is to be said for the association of the SH2 domain-bearing PI3K p85 catalytic subunit to IRS-1. Also, no changes in phospho IR in AD brain were found (results not shown). Accordingly, proximal components are not affected. However, changes in phospho IR and p85 PI3K interaction with IRS-1 were expected to track together and when p-Akt levels are reduced in the AD brain, both p-Tyrosine IR and PI3K/IRS-1 interactions were expected to be depressed. Several studies have been published in the literature related to changes in insulin, IGF-1, and their receptors in AD (for example, Steen, E., Terry, B. M., Rivera, E. J., Cannon, J. L., Neely, T. R., Tavares, R., Xu, X. J., Wands, J. R., and de la Monte, S. M., 2005, Impaired insulin and insulin-like growth factor expression and signaling mechanisms in Alzheimer's disease—is this type 3 diabetes?, *J Alzheimers Dis* 7:63-80). However, given the many conflicting results in the literature with respect to changes in insulin, IGF-I, their receptors and activation state of insulin signaling components in AD brain, experimental cell culture and in vitro conditions were used to dissect the role of intracellular Aβ in the disruption of insulin signaling. Skeletal muscle-like $C_2C_{12}$ myotubes were used because skeletal muscle is very insulin responsive and Inclusion Body Myositis, a condition that shares pathology with AD with respect to intracellular amyloid aggregation, is partly a degenerative disorder of skeletal muscle (Askanas, V., and Engel, W. K., 2001, Inclusion-body myositis: newest concepts of pathogenesis and relation to aging and Alzheimer disease, *J Neuropathol Exp Neurol* 60:1-14). Results were confirmed in SH-SY5Y neuroblastoma cells.

Example 3

Aβ42 Toxicity and Akt1 Inhibition in Cultured Cells

Figure 5A:
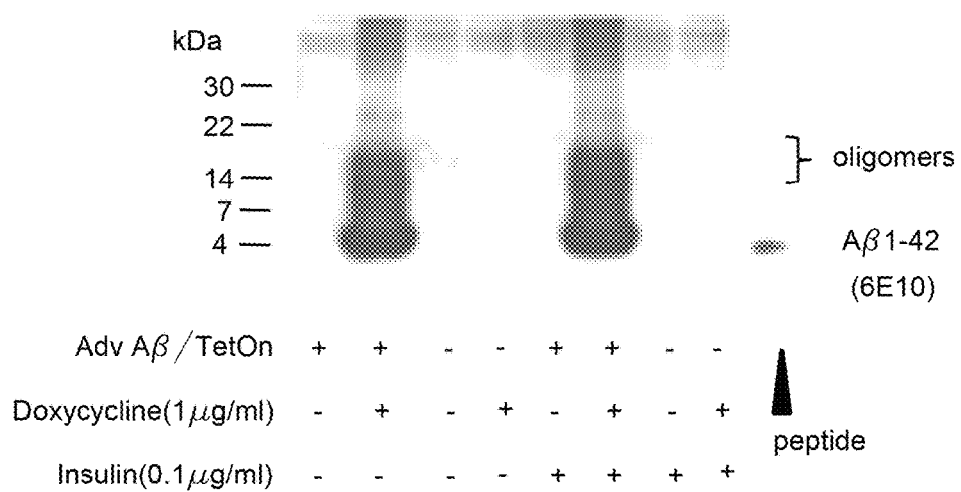
Figure 5B:
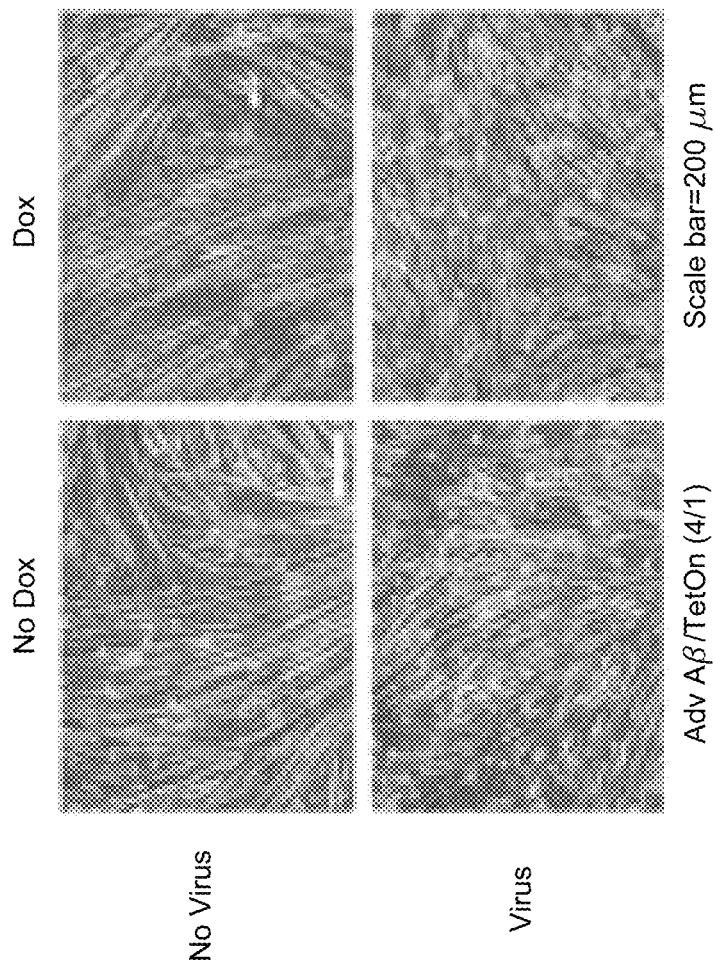
Figure 5B:
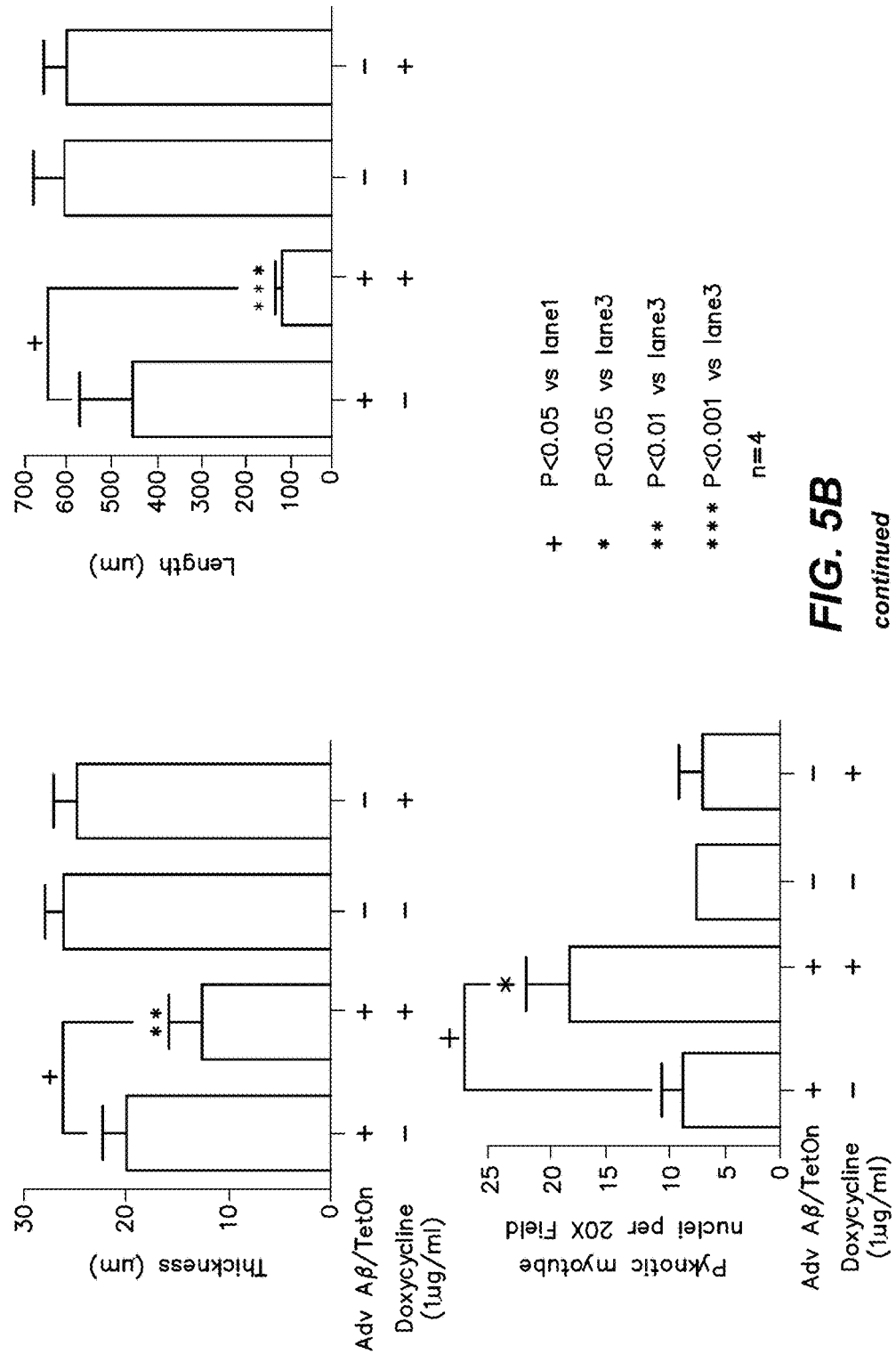

The specific inhibition of Akt activation in the brain associated with elevated Aβ levels was explored mechanistically in both neuronal and skeletal muscle cell cultures in the presence and absence of added insulin to stimulate the Akt pathway. An adenovirus construct encoding Aβ42 under tetracycline control (Adv Ali/TetOn) was used to infect $C_2C_{12}$ myotubes and SH-SY5Y neuroblastoma cells. Before harvesting, $C_2C_{12}$ cells expressing Aβ, once given doxycycline, were treated for 30 minutes with either insulin (0.1 μg/ml) or vehicle as indicated in FIGS. 5A and C. Cell lysates were used for direct western analysis, IP/western and activity assays as in FIG. 4. The results in FIG. 5A show the Aβ42 expression levels achieved in the doxycycline-inducible Adv AP/TetOn transductions. Both monomers and presumptive oligomers of Aβ were induced. Insulin treatment had no effect on Aβ levels. Morphologically, the myotubes exhibited significant reductions in both length and thickness (FIG. 5B). Moreover, myotubes containing condensed nuclei were increased in number by intracellular expression of Aβ42 (FIG. 5B graphs).

Figure 5C:
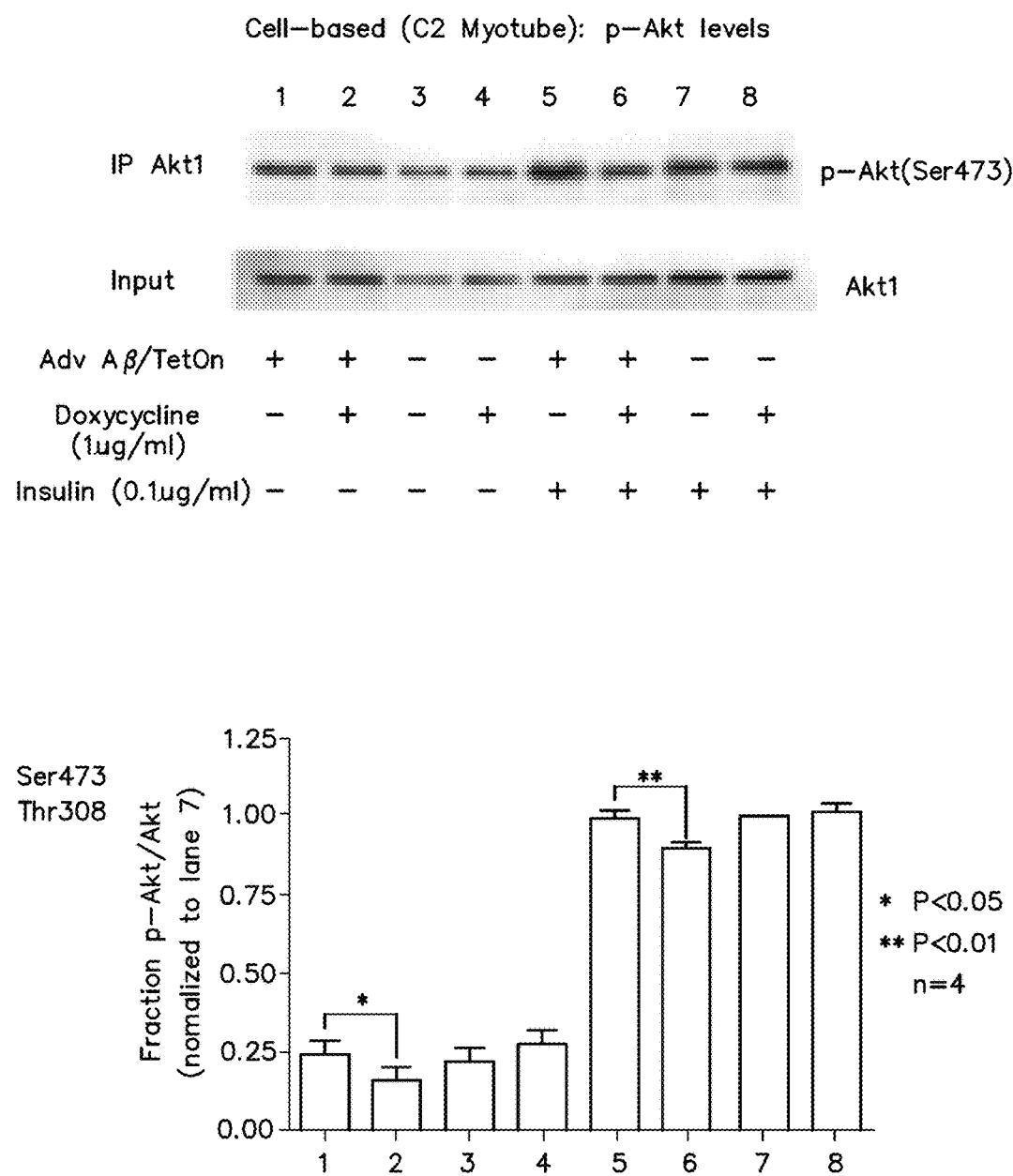

Myotube culture extracts were used for IP and western blot to determine levels of p-Akt, Akt activity and IR activation Immunoprecipitation of Akt1 shows inhibited levels of Ser473 phosphorylation in Aβ42-expressing cultures, especially when stimulated by insulin (lane 6 vs. lane 5; FIG. 5C top). Insulin upregulates p-Akt levels under all other control conditions (lanes 5, 7, 8 vs. lanes 1, 3, 4 respectively). The graph shown below summarizes the quantification from experiments examining either Ser473 or Thr308 phosphorylations. The same results were obtained in experiments on SH-SY5Y cells (not shown). In Akt1 activity assays, a GSK-3 fusion protein (30 kDa) was used as substrate. Stimulated Akt1 activity is similarly shown to be inhibited as a result of intracellular Aβ42 expression (FIG. 5C bottom, lane 6). The effect of AP42 was also tested on the phosphotyrosine (p-Tyr) signature indicating activation of the insulin receptor beta subunit (IRP) (FIG. 5D) Immunoprecipitation of p-tyrosine proteins and detection by western blot for IRP showed no change in IRP phosphorylation under Aβ expression conditions (FIG. 5D). Levels of Akt phosphorylation (Ser473) were slightly decreased, even under resting (no added insulin) conditions, consistent with FIG. 4C above.

In FIG. 5A, 90% confluent myoblast cultures in 24 well plates were infected with Adv Aβ42/TetOn virus (4:1 ratio; 100 m.o.i. total). After 24-36 hours, growth medium was replaced with DMEM, 2% horse serum. The medium was renewed the next day. At 24-36 hours after infection, doxycycline (Dox; 1 μg/ml) was added. Cultures were treated with insulin (0.1 μg/ml) for 15 minutes just before harvest at 24-36 hours after the doxycycline addition. Monomeric and oligomeric β-amyloid species are detected in doxycycline-induced cultures.

In FIG. 5B, the expression of intracellular Aβ led to significant decreases in both myotube length and caliber as well as increases in counts of pyknotic nuclei (stained with Hoechst 33258). For all samples a total of five 20X fields were manually counted. +P<0.05 vs lane 1; * P<0.05 vs lane 3;  P<0.01 vs lane 3; * P<0.001 vs lane 3; N=4 (2-tailed Student's T-test).

In FIG. 5C, $C_2C_{12}$ myotube cultures infected with Adv Aβ42/TetON were stimulated for 20 minutes with insulin, then harvested and used for IP of Akt1 (IP Akt1). Phospho-Akt (Ser473) levels are reduced (top panels) in Aβ-expressing/insulin-stimulated cells (lane 6). In the absence of insulin treatment there was also a small but significant decrease in Akt phosphorylation (lane2). Quantitation of both pSer473 and pThr308 Akt is given in the histogram. Lower panels show immunoprecipitated Akt1 was used for an in vitro kinase activity assay. Akt-IP was incubated with 1 μg of synthetic GSK-3 fusion protein substrate (30 kDa) in the presence of ATP and kinase buffer. Immunoblot of p-GSK-3 α/β shows inhibited phosphorylation in insulin treated myotubes expressing Aβ. * P<0.05; ** P<0.01; N=4 (2-tailed Student's T-test).

In FIG. 5D, 100 μg of protein from myotube extracts infected with Adv AP/TetOn was used for IP with anti-phosphotyrosine. Phosphorylation of IRP was unaffected in doxycycline-induced cultures.

Accordingly, Aβ42 expression in $C_2C_{12}$ myotubes is cytotoxic (FIG. 5B and Querfurth et al., Querfurth, H. W., Suhara, T., Rosen, K. M., McPhie, D. L., Fujio, Y., Tejada, G., Neve, R. L., Adelman, L. S., and Walsh, K., 2001, Beta-amyloid peptide expression is sufficient for myotube death: implications for human inclusion body myopathy, *Mol Cell Neurosci* 17:793-810 and resulted in a modest decline in Akt phosphorylation, consistent with results in neuronal Magrane, J., Rosen, K. M., Smith, R. C., Walsh, K., Gouras, G. K., and Querfurth, H. W., 2005, Intraneuronal beta-amyloid expression downregulates the Akt survival pathway and blunts the stress response, *J Neurosci* 25:10960-10969, and endothelial cells Suhara, T., Magrane, J., Rosen, K., Christensen, R., Kim, H. S., Zheng, B., McPhie, D. L., Walsh, K., and Querfurth, H., 2003, Abeta42 generation is toxic to endothelial cells and inhibits eNOS function through an Akt/GSK-3beta signaling-dependent mechanism, *Neurobiol Aging* 24:437-451). The inhibition of Akt phosphorylation became more evident when Aβ expression preceded amplification of insulin signaling (FIG. 5C), suggesting interference of some forward step. The functional consequence was a severe inhibition of Akt activity to phosphorylate a substrate (GSK-3) peptide. As in the AD brain samples, the more proximal activation of the insulin receptor is not interrupted by intracellular Aβ, since no changes in phospho-tyrosine IR levels were produced under identical expression conditions (FIG. 5D).

Since the cell-based results pointed to an inhibitory action of Aβ expression to prevent insulin-mediated Akt activation, rather than to deactivate resting p-Akt or activity levels, in vitro experiments were used for further analysis. Here, the activation is manipulated by adding PDK1 and ATP to the reaction mixture (Chen, H., Nystrom, F. H., Dong, L. Q., Li, Y., Song, S., Liu, F., and Quon, M. J., 2001, Insulin stimulates increased catalytic activity of phosphoinositide-dependent kinase-1 by a phosphorylation-dependent mechanism, *Biochemistry* 40:11851-11859) and the inhibition is tested upon addition of synthetic Aβ peptides. After validating the stimulation of Akt activity, immuno-precipitated from skeletal muscle and neuronal-like cells, by PDK, its expected inhibition was shown after addition of freshly prepared Aβ1-42. The interruption of PDK-dependent Akt activation brought GSK-3 phosphorylation back down to basal levels in the absence of PDK. Additional experiments indicate that peptide samples containing oligomeric species of Aβ (prepared as ADDLs) are more toxic to Akt activation than monomer predominant or fibril-containing preparations, the latter showing little toxicity (summarized in FIG. 7A). The Ki for monomeric-predominant preparations of Aβ42 is ~2 μM in activity assays and ~10 μM in western blots of p-Akt levels. The reason for this difference is not clear but may suggest activity is steeply dependent on the phosphorylation level. Intracellular concentrations of Aβ42 in AD and transgenic-affected tissue and cell culture models are difficult to come by, however, a range of 100 nM to low μM in compartments has been suggested (Gouras, G. K., Tsai, J., Naslund, J., Vincent, B., Edgar, M., Checler, F., Greenfield, J. P., Haroutunian, V., Buxbaum, J. D., Xu, H., et al., 2000, Intraneuronal Abeta42 accumulation in human brain, *Am J Pathol* 156:15-20, Magrane, J., Rosen, K. M., Smith, R. C., Walsh, K., Gouras, G. K., and Querfurth, H. W., 2005, Intraneuronal beta-amyloid expression downregulates the Akt survival pathway and blunts the stress response, *J Neurosci* 25:10960-10969, and Zhang, Y., McLaughlin, R., Goodyer, C., and LeBlanc, A., 2002, Selective cytotoxicity of intracellular amyloid beta peptide 1-42 through p53 and Bax in cultured primary human neurons, *J Cell Biol* 156: 519-529). These results are consistent with the viral expression studies in cells, where intracellular oligomerization is also shown. Previous works on synaptic transmission and cell viability have also detailed the heightened toxicity of oligomeric amyloid species (Walsh, D. M., Klyubin, I., Fadeeva, J. V., Rowan, M. J., and Selkoe, D. J., 2002, Amyloid-beta oligomers: their production, toxicity and therapeutic inhibition, *Biochem Soc Trans* 30:552-557, Lambert, M. P., Barlow, A. K., Chromy, B. A., Edwards, C., Freed, R., Liosatos, M., Morgan, T. E., Rozovsky, I., Trommer, B., Viola, K. L., et al., 1998, Diffusible, nonfibrillar ligands derived from Abeta 1-42 are potent central nervous system neurotoxins, *Proc Natl Acad Sci USA* 95:6448-6453, Chong, Y. H., Shin, Y. J., Lee, E. O., Kayed, R., Glabe, C. G., and Tenner, A. J., 2006, ERK1/2 activation mediates Abeta oligomer-induced neurotoxicity via caspase-3 activation and tau cleavage in rat organotypic hippocampal slice cultures, *J Biol Chem* 281:20315-20325).

Example 4

In Vitro p-Akt and Activity Levels: Effects of AP Peptides

Figure 6A:
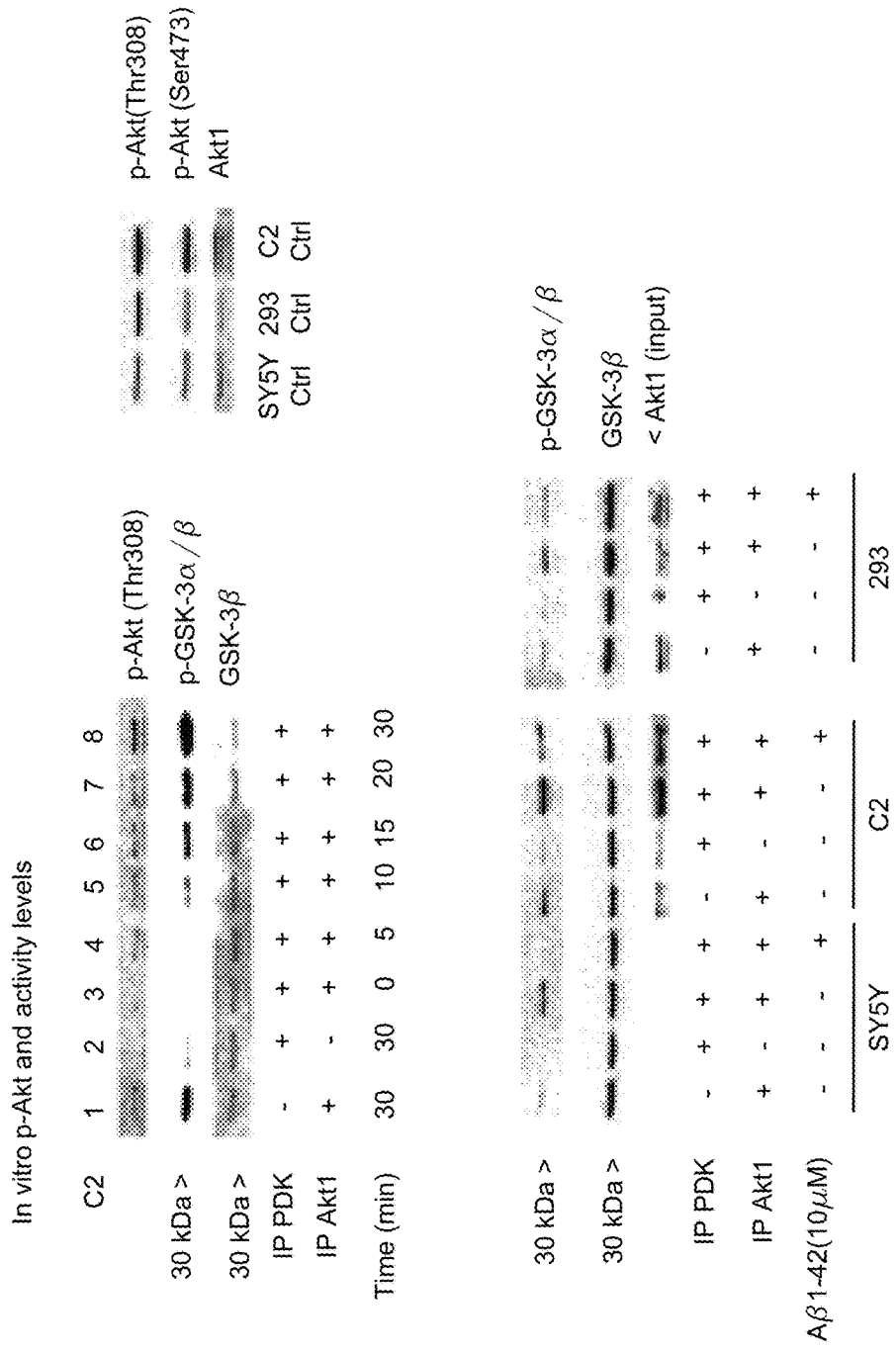
FIGS. 6A-6D illustrate the effects of Aβ monomer, ADDL and fibril preparations on in vitro PDK-dependent activation of Akt1
Figure 6B:
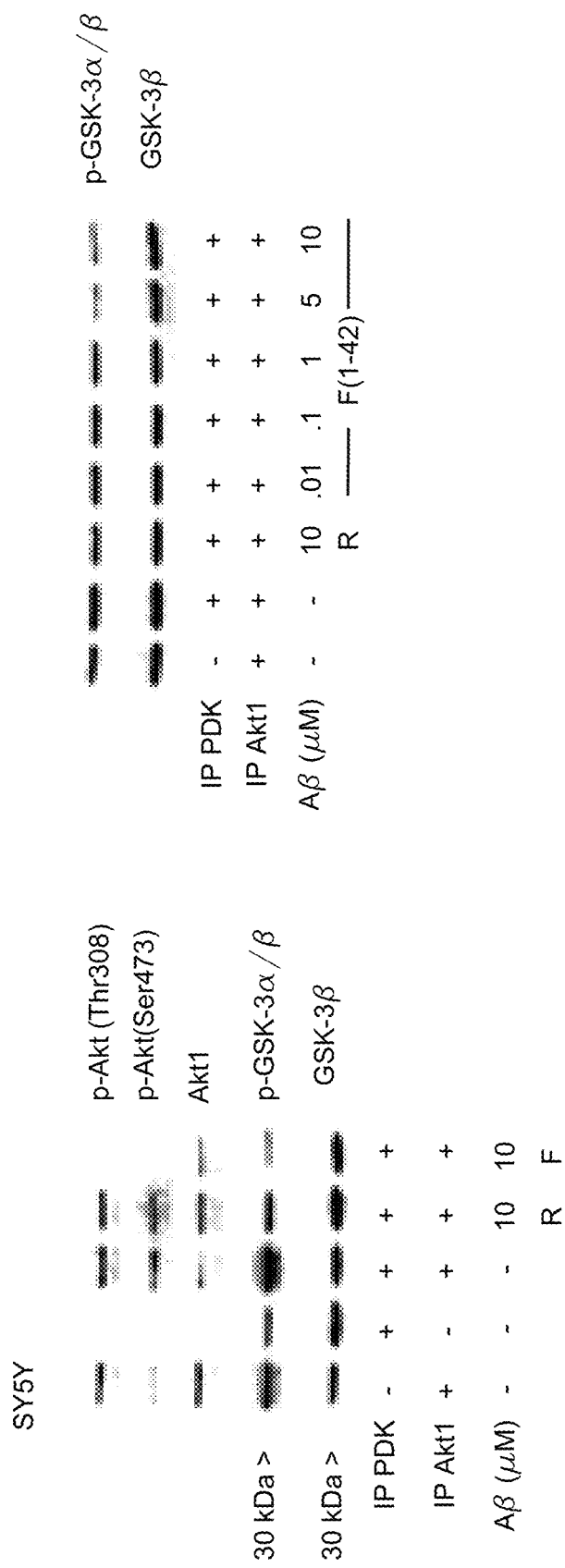

In order to confirm the downregulation of both Akt activation and activity and further test the amyloid species most accountable for the effect, a series of cell-free, in vitro reactions were performed. In FIG. 6A, the addition of immuno-purified PDK1 to Akt1 is shown to induce both Akt phosphorylation and its activity to modify the GSK-3 fusion protein substrate. Maximum stimulation occurred at the 30 minute time point, which was chosen for all subsequent experiments. However, basal activity of the immunoprecipitated Akt obtained from $C_2C_{12}$ myotubes was also high (lane1). The resting levels of Akt phosphorylation for several cell types are compared in FIG. 6A, top right, indicating that $C_2C_{12}$ myotubes have high levels and neuroblastoma cells the lowest levels of intrinsic Akt activation relative to HEK cells. When the effect of adding freshly prepared, synthetic Aβ42 was compared between the cell types, each having different levels of endogenous Akt activation, Aβ42 inhibited all PDK1-stimulated Akt activity levels (FIG. 6A, bottom). Thus in SH-SY5Y and HEK293 cells, where PDK1 additions greatly increased low levels of Akt activity associated with the Akt-Sepharose preparation, Aβ42 completely abrogated the effect. In $C_2C_{12}$ cells, Aβ addition reduced PDK1 stimulated Akt activity back to the relatively high basal levels (IP Akt1 alone). Thus, Aβ42 appears to interfere with the degree to which activation is attributable to PDK1. Next, it is shown in FIG. 6B that the in vitro inhibition of Akt phosphorylation and activation is more specific to the forward peptide sequence (10 µM F) than to the reverse (R). The predominantly monomeric synthetic peptide preparation is shown to inhibit in vitro Akt1 activity in a dose-dependent manner (FIG. 6B). Neither reverse nor scrambled Aβ sequence inhibited these activity assays at doses up to 5 µM (FIG. 6D middle; Scr).

Figure 6C:
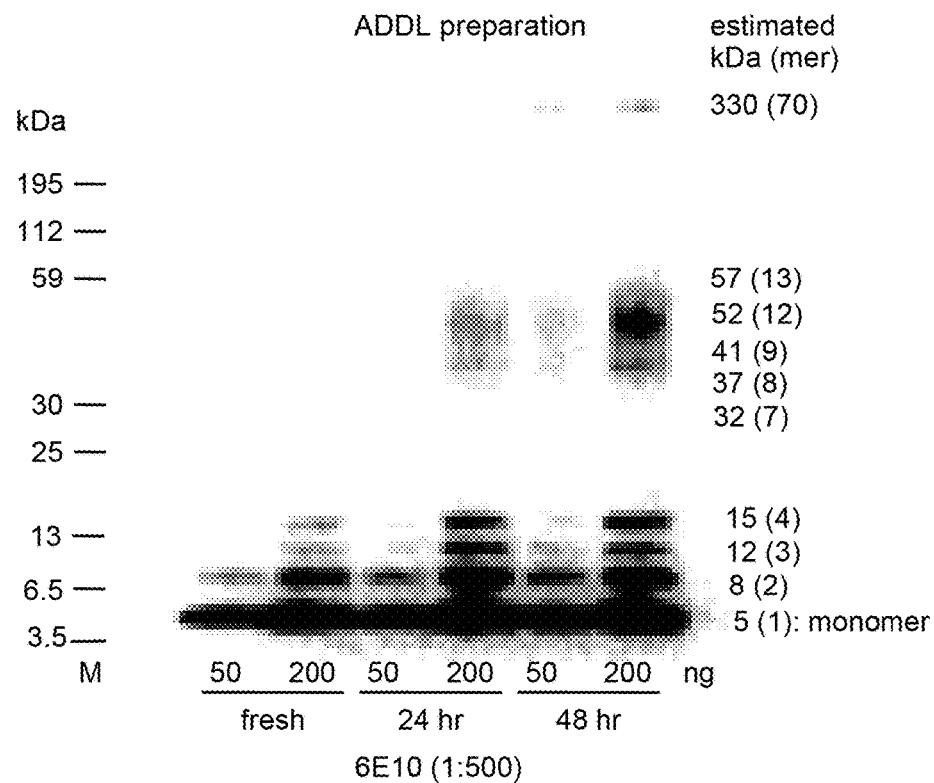
Figure 6C:
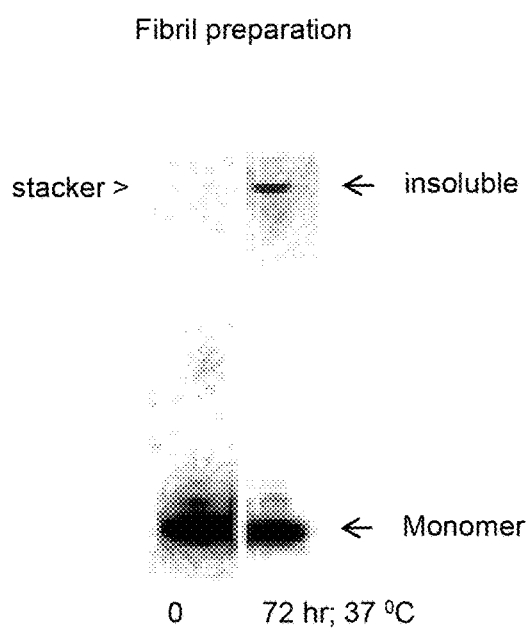
Figure 6C:
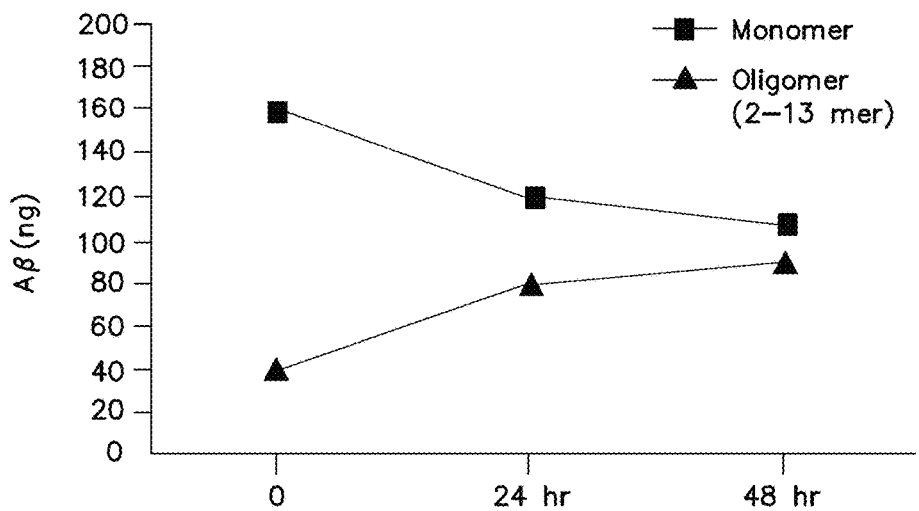
Figure 6C:
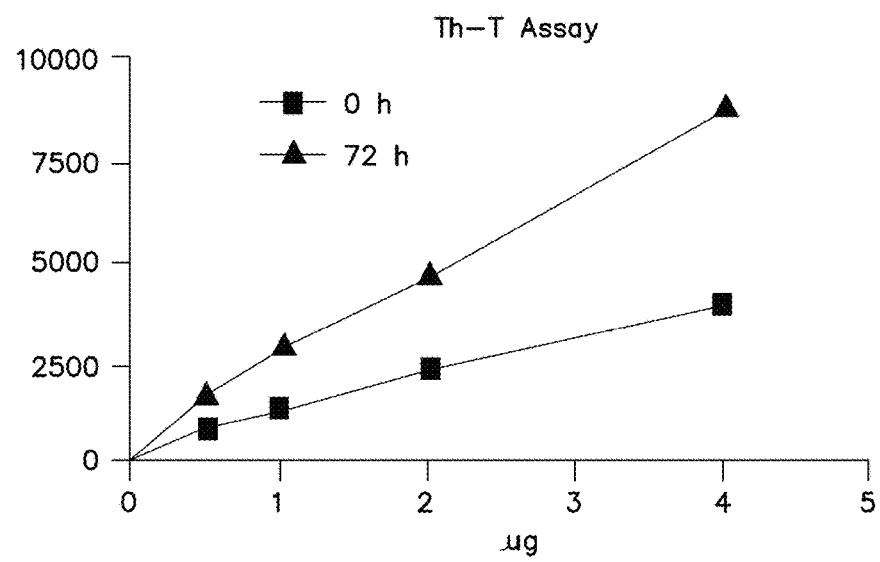
Figure 6D:
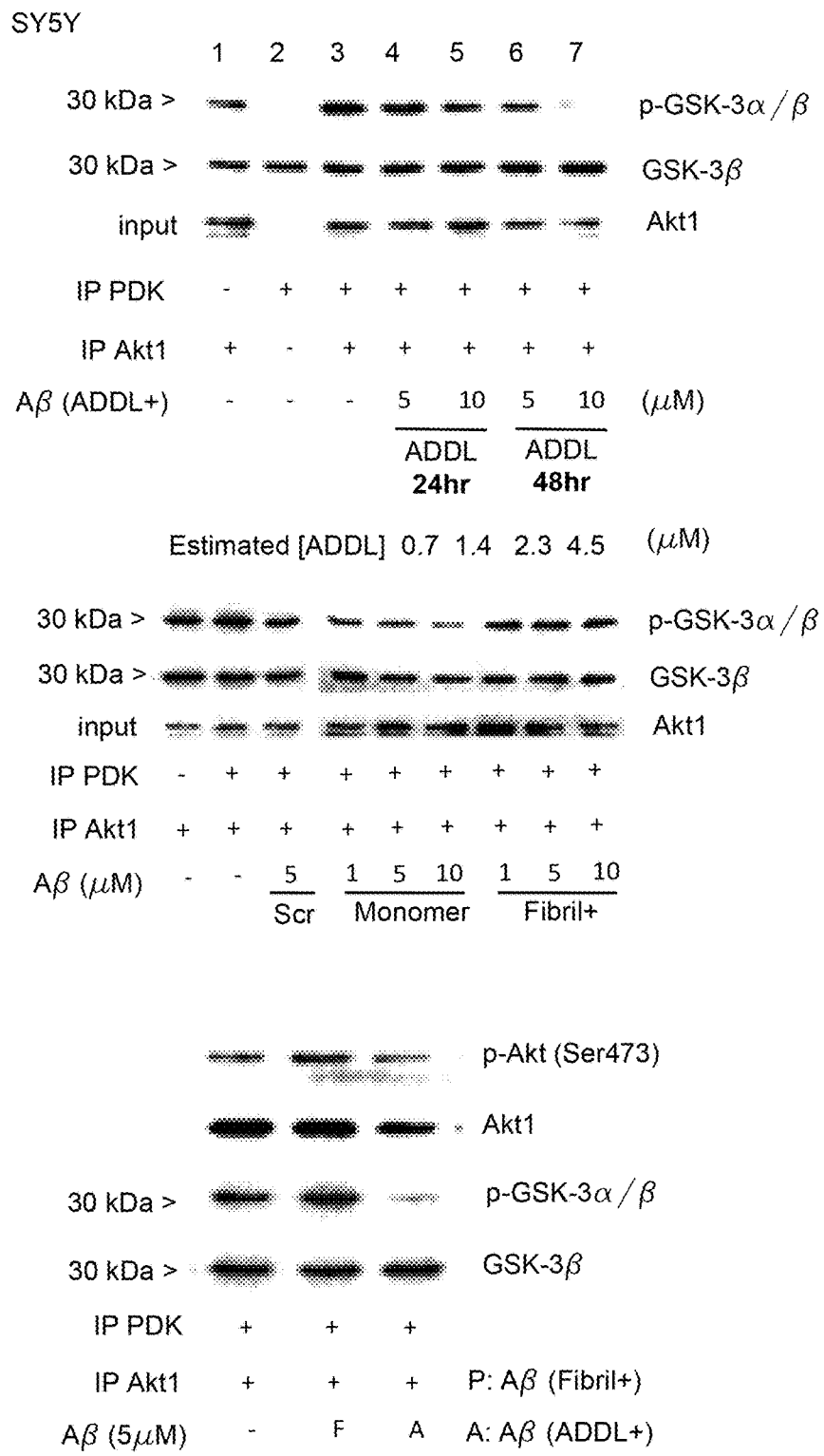

Oligomeric species of β-amyloid have recently been most implicated in neuronal toxicity (Townsend, M., Shankar, G. M., Mehta, T., Walsh, D. M., and Selkoe, D. J., 2006, Effects of secreted oligomers of amyloid beta-protein on hippocampal synaptic plasticity: a potent role for trimers, *J Physiol* 572:477-492, and Walsh, D. M., Klyubin, I., Fadeeva, J. V., Rowan, M. J., and Selkoe, D. J., 2002, Amyloid-beta oligomers: their production, toxicity and therapeutic inhibition, *Biochem Soc Trans* 30:552-557). The effects of synthetic Aβ monomer, oligomer (as amyloid-beta derived diffusible ligands or ADDL) and fibril preparations (FIG. 6C) on Akt activity derived from SH-SY5Y cells (FIG. 6D) were compared. Freshly made monomers were used to make 24 and 48 hr preparations containing ADDLs (Lambert, M. P., Barlow, A. K., Chromy, B. A., Edwards, C., Freed, R., Liosatos, M., Morgan, T. E., Rozovsky, I., Trommer, B., Viola, K. L., et al., 1998, Diffusible, nonfibrillar ligands derived from Abeta 1-42 are potent central nervous system neurotoxins, *Proc Natl Acad Sci U S A* 95:6448-6453). At both incubation time points, the levels of oligomeric species (2-13mers) are shown to increase relative to the monomers (FIG. 6C and graph). At 48 hours incubation, small amounts of insoluble, presumably fibrillar Aβ, accumulated at the interface between stacking and resolving gels. Fibrillar Aβ was also prepared and analyzed by Western blot and thioflavin T (Th-T) assay (FIG. 6C bottom). A dose- and time-dependent increase in Th-T fluorescence was correlated with the appearance of insoluble Aβ immunoreactivity. Using these preparations on SH-SY5Y starting material in the in vitro assay of PDK1 stimulated Akt activity, the oligomer containing preparations (ADDL+) were found to be more potent inhibitors than either monomers or fibrillar β-amyloid. The ADDL preparations resulted in near total inhibition of PDK1 stimulated Akt1 activity at 10 µM (estimated 4.5 µM oligomeric content) (FIG. 6D top). In comparing monomer to fibril-containing preparations, the fibrillated ones appeared least active (FIG. 6D middle). At 5 µM total Aβ concentration, the ADDL(+) containing preparation showed the greatest interference with the stimulation of SH-SY5Y-derived Akt1 activity by PDK1 (FIG. 6D bottom; p-GSK-3 α/β).

In FIG. 6A, the upper panels show PDK1 and Akt1 immunoprecipitated from $C_2C_{12}$ myotubes, and the time-dependence of the phosphorylation of Akt and its substrate fusion protein. IP PDK was added to assay mixtures at time 0. Akt1 activity levels (generation of p-GSK-3 α/β) increase during the minutes specified (5, 10, 15, 20 and 30, at 30° C.). Resting levels of Akt phosphorylation are shown for multiple cell types (SH-SY5Y, HEK 293 and $C_2C_{12}$; right top). These same cell extracts were used to IP Akt and PDK for the PDK-dependent Akt activity assays in the presence of freshly prepared synthetic Aβ shown below. In all cell types, PDK-dependent Akt activation was inhibited by Aβ (10 µM) (bottom panels).

In FIG. 6B, PDK and Akt1 were immunoprecipitated from SH-SY5Y cell extracts and PDK-dependent Akt activation examined in vitro as described above. Akt activation (pSer473, pThr308) and Akt activity (p-GSK-3 α/β) are affected by the forward sequence (F) AP1-42 peptide (left panels) beginning at ~1 µM (R is reverse Aβ (Aβ42-1).

In FIG. 6C, amyloid fibrils and ADDLs were prepared as described in Klein, W. L., 2002. Abeta toxicity in Alzheimer's disease: globular oligomers (ADDLs) as new vaccine and drug targets, *Neurochem Int* 41:345-352. Aβ stock in 100% DMSO was diluted in F12 medium and incubated 24 or 48 hours at 4~5 ° C. Samples comprised of 50 or 200 ng starting material, either freshly dissolved peptide or ADDL-containing after 24 and 48 hr incubations, were examined by Western (MAb 6E10 (1:500), 4-12% polyacrylamide Bis-Tris gel). Estimated molecular weights of each oligomeric species are shown to the right. Aβ 2, 3, 4, 7, 8, 9, 12 and 13-mer were increased in the ADDL preparation. Individual, oligomer band densities were measured densitometrically, summated and normalized to the total running amount of peptide (200 ng). The abundance of the 2~13 mers (oligomer) and the remainder (monomer) are plotted in the graph to the right against time. Oligomer formation increases with incubation time. Lower panels show that fibrils were prepared by the method of Stine, W. B., Jr., Dahlgren, K. N., Krafft, G. A., and LaDu, M. J., 2003. (In vitro characterization of conditions for amyloid-beta peptide oligomerization and fibrillogenesis, *J Biol Chem* 278:11612-11622), and confirmed by immunoblot and Thioflavin T (Th-T) assay (Conway, K. A., Lee, S. J., Rochet, J. C., Ding, T. T., Williamson, R. E., and Lansbury, P. T., Jr., 2000, Acceleration of oligomerization, not fibrillization, is a shared property of both alpha-synuclein mutations linked to early-onset Parkinson's disease: implications for pathogenesis and therapy, *Proc Natl Acad Sci U S A* 97:571-576). Fibrils were detected at the interface of the stacking and the resolving gel, and confirmed by an increase in thioflavin-T fluorescence (right).

In FIG. 6D, the top panels show PDK and Akt1 that were immunoprecipitated from SH-SY5Y cells as in the in vitro activation assay above. The amount of starting (total) Aβ in these ADDL preparations that was added to the mixture is indicated. The actual concentration of ADDLs was estimated by determining the ratio of 52mer to monomer in FIG. 6C. ADDLs from 48 hours pre-incubation significantly prevented the stimulation of Akt activity by PDK. The middle panels shows fibrillated preparations of Aβ compared to monomer, the former showing little effect. Scrambled sequence peptide (Scr; 5 µM) produced a minor decrease in activation. The lower panel shows 5 µM of monomer, fibril and ADDL-containing preparations tested side-by-side.

The lipid second messenger PIP3 is necessary to the efficient activation of Akt via PDK and is probably brought down in sufficient amounts by the pull-downs. Indeed, preincubation of the starting material with PTEN, a lipid phosphatase, abrogated the stimulatory affect of PDK (FIG. 7C). Conversely, additions of PIP3 further boost PDK-induced Akt phosphorylation and activity (FIG. 7B). Importantly, Aβ addition greatly attenuated Akt activation in the presence or absence of added PIP3. Since adding PIP3does not offset the Aβ effect by mass action, sequestration of this lipid as a mechanism of Aβ inhibition is eliminated. To be clear on this, -Aβ was tested against the PDK-dependent, but PIP3-independent, stimulation of the serum/glucocorticoid-regulated protein kinase (SGK) (Kobayashi, T., and Cohen, P., 1999, Activation of serum- and glucocorticoid-regulated protein kinase by agonists that activate phosphatidylinositide 3-kinase is mediated by 3-phosphoinositide-dependent protein kinase-1 (PDK1) and PDK2, *Biochem J* 339 (Pt 2):319-328). It was found that Aβ (ADDLs) also interrupted PDK-dependent activation of SGK in the same in vitro assay (FIG. 7D). In a reverse control experiment PDK was replaced with another Akt-activator, Rictor. Rictor was shown to activate Akt in FIG. 7D, but was not interrupted by Aβ42. Finally, Akt was replaced with PKA, a kinase well known to phosphorylate GSK-3β. Aβ42 had no influence on this reaction either. The results all strongly suggest that Aβ attacks the influence of PDK on Akt.

Example 5

In vitro p-Akt and Activity Levels: Roles of PIP3 and Converging Kinases

Figure 7A:
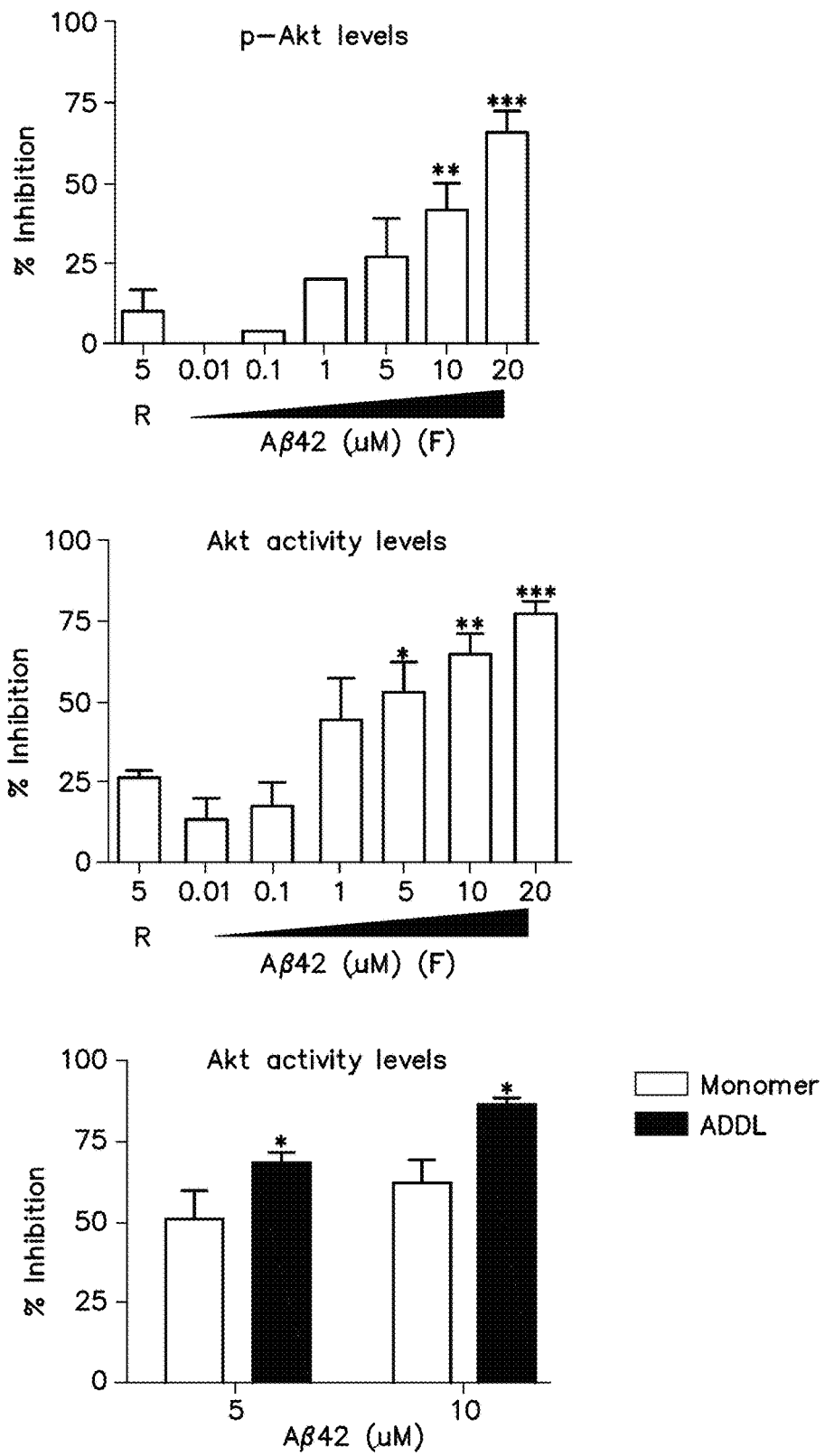
FIGS. 7A-7D illustrate specific properties of Aβ-directed inhibition of PDK Activity
Figure 7B:
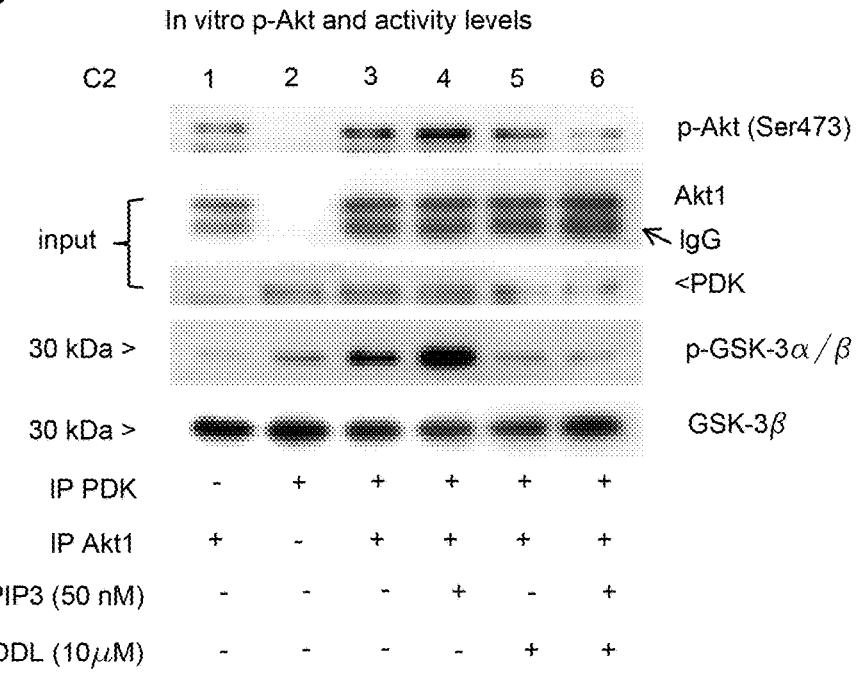
Figure 7C:
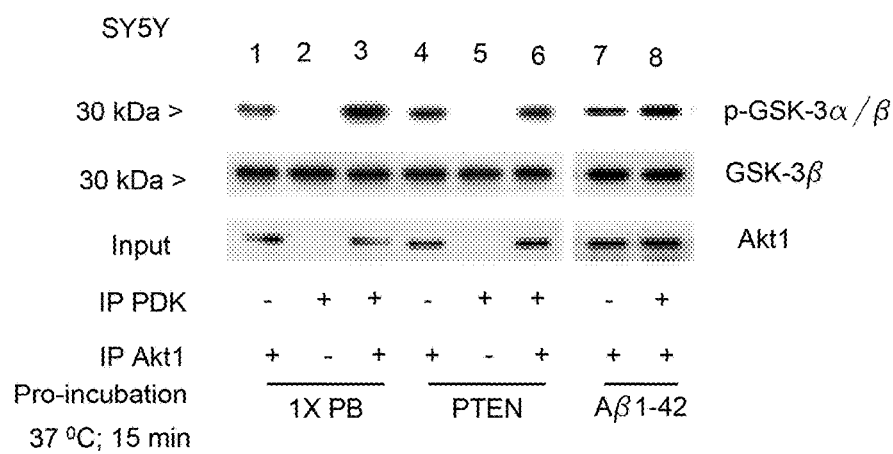
Figure 7D:
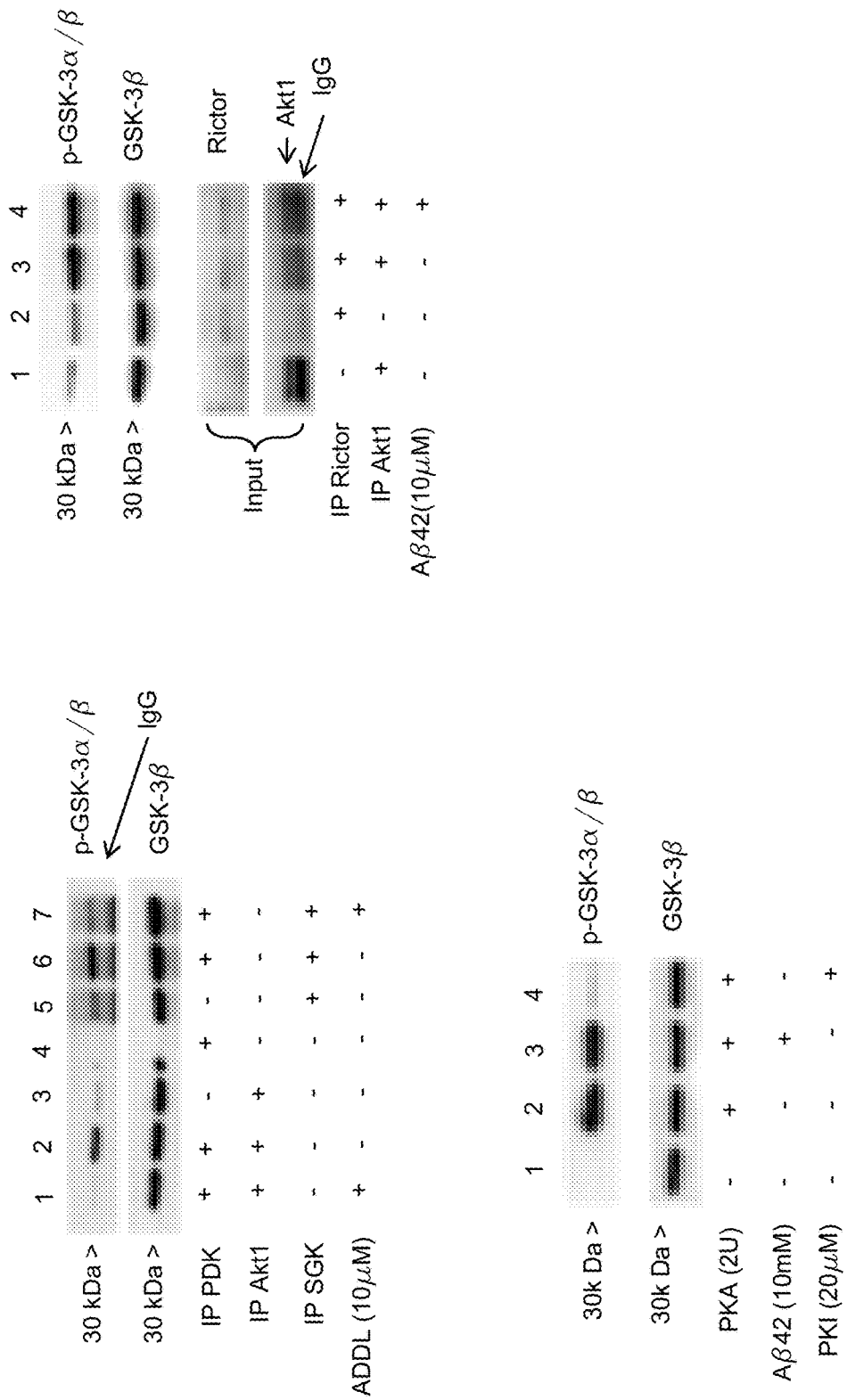

FIG. 7A provides a quantitative summary of the dose-dependent, inhibitory effects of freshly prepared, predominantly monomeric, Aβ42 (forward peptide) on the phosphorylation of Akt by PDK and on the Akt activation. While 10 µM Aβ42 produced up to 50% inhibition of Akt phosphorylation, only 1 µM was sufficient to inhibit Akt activation to a similar degree. The reverse peptide (Aβ42-1, R) at 5 µM (or 10, not shown) had a measurable but relatively smaller effect to inhibit Akt activation. Scrambled peptide (10 µM) controls resulted in minor inhibition (below 10%, not shown). Thus, the functional degree of Akt activation, as judged by enzyme activity level, is the more sensitive measure of impairment by Aβ. In FIG. 7A right, the ADDL-containing Aβ preparations, compared to the same starting material of monomeric Aβ, are additively more injurious to Akt activation (p<0.05).

Phosphatidylinositol 3,4,5-trisphosphate (PIP3) is a second messenger lipid that interacts with PH domain containing proteins, Akt1 and PDK, and organizes their co-recruitment to the submembrane for activation. If Aβ inhibits the action of PDK to activate Akt, one mechanism that was tested is if it does so by competition for PIP3. The FIG. 6 in vitro experiments showed that it was not necessary to add PIP3 to obtain PDK-mediated activation of Akt. In order to fully appreciate the dynamic range of Akt activation from basal levels and the extent to which PIP3 is a cofactor in the in vitro assay using the immunoprecipitated kinases, the Akt starting material was dephosphorylated with a protein phosphatase 2A (PP2A) treatment. In FIG. 7B, large increases in PDK-stimulated p-Akt and activity levels are shown (lane 3 vs. 1). In addition, an extra increase in PDK-dependent Akt1 phosphorylation and activity is obtained in the presence of PIP3 (50 nM, lane 4 vs. 3). The ADDL-containing Aβ42 peptide preparation inhibited PDK-dependent Akt1 activity and the phosphorylation of Akt (Ser473) with or without added PIP3. The same results are obtained when PDK and Akt are obtained from SH-SY5Y cells (data not shown). Thus, PIP3 addition did not overcome the Aβ42-mediated inhibition of Akt activation.

Another possibility is that Aβ acts like the phosphatase and tensin homolog (PTEN) in dephosphorylating PIP3. Therefore, in FIG. 7C, preincubation of the kinase-bearing beads with PTEN, expected to reduce endogenous co-precipitated PIP(3), was tested to see if it would eliminate PDK-stimulated Akt activity. Indeed, there is no activation in lane 6 vs. 4, as there is in lane 3 vs. 1. Moreover, preincubation with Aβ 1-42, followed by washing of beads before setting-up the activity reaction, had no effect on GSK substrate phosphorylation (lane 8 vs. 7). The inference is that Aβ does not act like PTEN to prevent attachment or remove 3' phosphate from lipid cofactors. The data in FIG. 10 shows that PTEN also has the expected action to inhibit PI3K action on lipid.

Another kinase, termed SGK (serum/glucocorticoid regulated kinase), is also activated by PDK. Similar to Akt, SGK has a PH domain and phosphorylates GSK-3 α/β (Kobayashi, T., Deak, M., Morrice, N., and Cohen, P., 1999, Characterization of the structure and regulation of two novel isoforms of serum- and glucocorticoid-induced protein kinase, *Biochem J* 344 Pt 1:189-197, and Tessier, M., and Woodgett, J. R., 2006, Serum and glucocorticoid-regulated protein kinases: variations on a theme, *J Cell Biochem* 98:1391-1407). If Aβ inhibits PH-mediated activations of Akt independent of PIP3, it is predicted to affect this mechanism too. Indeed, in FIG. 7D, ADDL-containing Aβ preparations inhibited PDK-stimulated SGK activity (lane 7 vs. 6 and 5). As shown previously, the same Aβ fully inhibited (lane 1) the PDK-stimulated activity of Akt1 (lane 2 vs. lane 3). The PH specificity hypothesis was further tested by using another kinase that regulates Akt but does not have a PH domain; Rictor (Sarbassov, D. D., Guertin, D. A., Ali, S. M., and Sabatini, D. M., 2005, Phosphorylation and regulation of Akt/PKB by the rictor-mTOR complex, *Science* 307:1098-1101, Hresko, R. C., and Mueckler, M., 2005, mTOR.RICTOR is the Ser473 kinase for Akt/protein kinase B in 3T3-L1 adipocytes, *J Biol Chem* 280:40406-40416). In the middle panel of FIG. 7D, IP Rictor was added to show that Akt activity is upregulated (lane 3 vs. 2 or 1). This enhanced activity was not however, interrupted by Aβ (10 µM, lane 4 vs. 3). Lastly, another kinase that converges to phosphorylate GSK, PKA (Grimes, C. A., and Jope, R. S., 2001, The multifaceted roles of glycogen synthase kinase 3beta in cellular signaling, *Prog Neurobiol* 65:391-426; Li, M., Wang, X., Meintzer, M. K., Laessig, T., Birnbaum, M. J., and Heidenreich, K. A., 2000, Cyclic AMP promotes neuronal survival by phosphorylation of glycogen synthase kinase 3beta, *Mol Cell Biol* 20:9356-9363), was tested. The right panel of FIG. 7D shows that c-AMP-dependent protein kinase A (PKA; 2U), while very active in phosphorylating the GSK-3 α/β substrate, was not inhibited by Aβ (lane 3 vs. 2). A standard inhibitor of PKA (PKI; 20 µM) showed the expected full knock-down of activity (lane 4). Thus, the mechanism of Aβ inhibition of Akt activation is specific to PDK-like kinases.

In FIG. 7A Details of Aβ dose-dependent inhibition of Akt phosphorylation (left graph) and Akt activation (right graph) expressed as percent of control reactions without added Aβ42. Aβ concentrations at or above 10 µM significantly inhibit Akt phosphorylation (activation) and at or above 5 µM the stimulation of Aka activity. * p<0.05;  p<0.01; * p<0.001. (2-tailed Student's T-test in comparison to the reverse peptide (5 µM) results). Comparison of ADDL preparations (5, 10 µM; estimated) to monomeric Aβ, show significantly greater inhibition of PDK-dependent Aka activity by ADDLs (right graph).

In FIG. 7B Immunoprecipitated (IP) PDK from insulin-treated (INS) $C_2C_{12}$ myotubes was added to IP Akt from SH-SY5Y cells. Prior to the activation assay Akt1-beads were incubated with PP2A (5 µg/ml) for 30 min at 30° C. expected to minimize basal Akt phosphorylation. The mixing of PDK and Aka led to a notable increase in p-Akt (Ser473) and Akt activity (Lane 3). However, this effect is now further enhanced by the addition of PIP3 (Lane 4). Inclusion of ADDL (10 µM) in the assay nearly eliminates PDK- or PDK+PIP3-induced activations and enhancements (Lanes 5 and 6).

In FIG. 7C Immunoprecipitated Akt1 and PDK were preincubated for 15 min at 37° C. in phosphatase buffer alone (1X PB), or with added PTEN (10.6 µg/ml), or Aβ. After complete washing of the beads with kinase buffer, the in vitro kinase reaction was performed. The addition of PDK increased Akt activity as expected in control reactions (Lane 3). Combining PTEN treated PDK and Akt1 beads eliminated any stimulation of Akt activity (Lane 6 vs. 4). Preincubating the two IP kinases each with Aβ, instead of PTEN, and followed by washout of Aβ, produced no inhibitory effect (Lane 8).

FIG. 7D left panel—Stimulated PDK was IP from insulin-treated $C_2C_{12}$ myotubes and used to maximally activate PP2A-treated IP Akt1 (as in FIG. 4B) and IP SGK in this in vitro kinase assay. Synthetic GSK-3 fusion protein served as substrate. Both Akt1 and SGK activities were up-regulated by PDK (Lanes 2 and 6). ADDL (10 µM) inhibited SGK activation as well (Lane 7 vs. 6). Middle panels—IP Rictor from insulin-treated $C_2C_{12}$ myotubes was used to activate PP2A-treated Akt1 immunoprecipitations. Input of added Rictor and Akt1 are shown below. IP Rictor alone showed some activity (Lane 2), likely due to some co-immunoprecipitated Akt1. While combining Rictor with IP Akt1 stimulates activity, there was no change through the addition of Aβ (10 µM) (Lanes 3 and 4). Right panels—Recombinant PKA (2U) was assayed for GSK-3p phosphorylation activity (Lane 2) in the presence or absence of PKI (Lane 4) or Aβ (Lane 3). The PKA inhibitor, PKI, blocked GSK conversion, as expected, Aβ (10 µM) did not.

Example 6

The Interaction of PDK with Akt1 is Interrupted by Aβ42

Figure 8A:
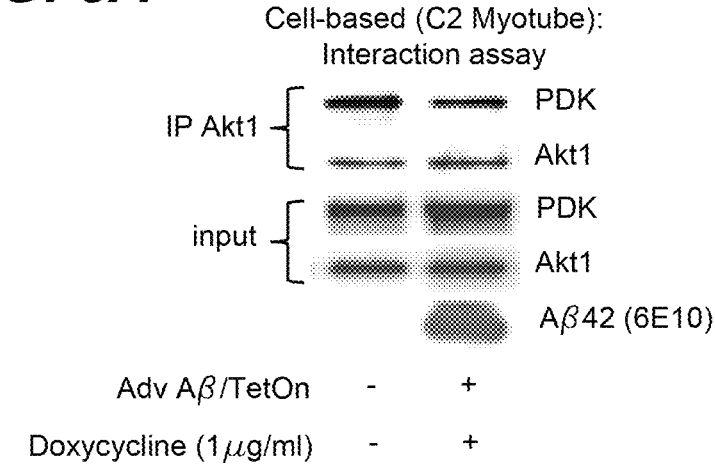
FIGS. 8A-8C illustrate pull-down type interaction assays between PDK and Akt1
Figure 8B:
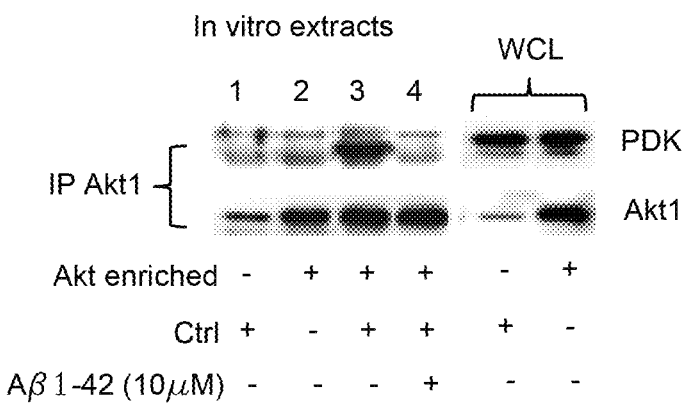
Figure 8C:
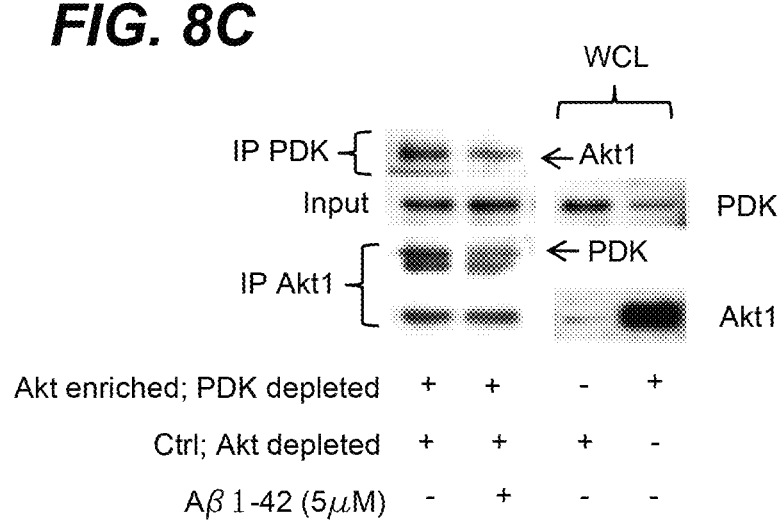

If Aβ interferes with the action of PDK to activate Akt, their physical interaction should be lessened. Indeed, FIG. 14A showed that the interaction of PDK with Akt1 in human AD brain is reduced. If correct, the same result is expected in the cell based and in vitro assays. In FIG. 8A, the expression of Aβ42 in $C_2C_{12}$ myotubes resulted in less pull-down of PDK with Akt. The direct association of PDK with Akt was similarly affected in the presence of synthetic Aβ in cell free extracts. Extracts from $C_2C_{12}$ myotubes enriched for Akt following infection by Adv encoding WT-Akt1 or from control cell cultures were used as a source of additional PDK as the starting material. In FIG. 8B, the addition of Aβ42 to a mixture of Akt-enriched and control extracts resulted in greatly inhibited pull-down of Akt-PDK complexes (lane 4 vs. 3). Total PDK levels were constant in the presence or absence of Akt expression (FIG. 8B, right panel). To explore this further in FIG. 8C, an Akt enriched/PDK-depleted and a control, Akt-depleted extract were combined before Aβ treatment and immunoprecipitation. The extent to which the extracts were successfully immuno-depleted of Akt (lane 3 vs. 4) or PDK (lane 4 vs. 3) are shown in FIG. 8C, right panel. When tested for Akt pull-down with IP PDK, Aβ42 additions inhibited the signal (FIG. 8C, lane 2 vs. 1, left panel, top). The reverse IP-western confirmed the result (bottom panels).

In FIG. 8A myotube cultures were infected with Adv Ali/TetOn for 24-36 hours, followed by addition of doxy-cycline (1 µg/ml) for 24-36 hours Immunoprecipitation of total Akt1 from Ap-expressing cells shows a decrease in co-immunoprecipitated PDK as compared to control cultures. Aβ42 expression was confirmed by immunoblot developed with MAb 6E10. Total Akt1 and PDK levels remain constant irrespective of Aβ (input).

In FIG. 8B Akt-enriched cell extracts were prepared from $C_2C_{12}$ myotube cultures that had been infected with Adv WT-Akt. Extracts from unstimulated, control cultures were relatively more abundant in PDK. Western blots of whole cell lysates (WCL) confirm the expected levels of Akt and PDK (right panel). 100 µg of cellular extract each from Akt-enriched and control cultures were mixed and incubated for 30 min at 30° C. Pull-down of PDK1 with Akt1 was significantly increased in the mixture of extracts (Lane 3). The interaction was abrogated by the addition of Aβ42 (10 µM) (Lane 4).

In FIG. 8C Akt-enriched; PDK depleted extract was prepared by removing PDK through IP from Adv WT-Akt expressing cell extracts. Control; Akt depleted lysate was prepared by removing Akt1 through IP from control cell extracts. The levels of depleted PDK and/or depleted Akt1 in WCL are shown in Lanes 3 and 4. Both Akt1- and PDK-enriched cell extracts, respectively, were mixed and incubated 30 min at 30° C. The reverse immunoprecipitation of PDK pulled-down less Akt1, and as above, IP of Akt1 pulled-down less PDK, in the presence of added Aβ42 (5 µM).

Example 7

Aβ does not Dephosphorylate or Inhibit Akt Action once Established

Figure 9A:
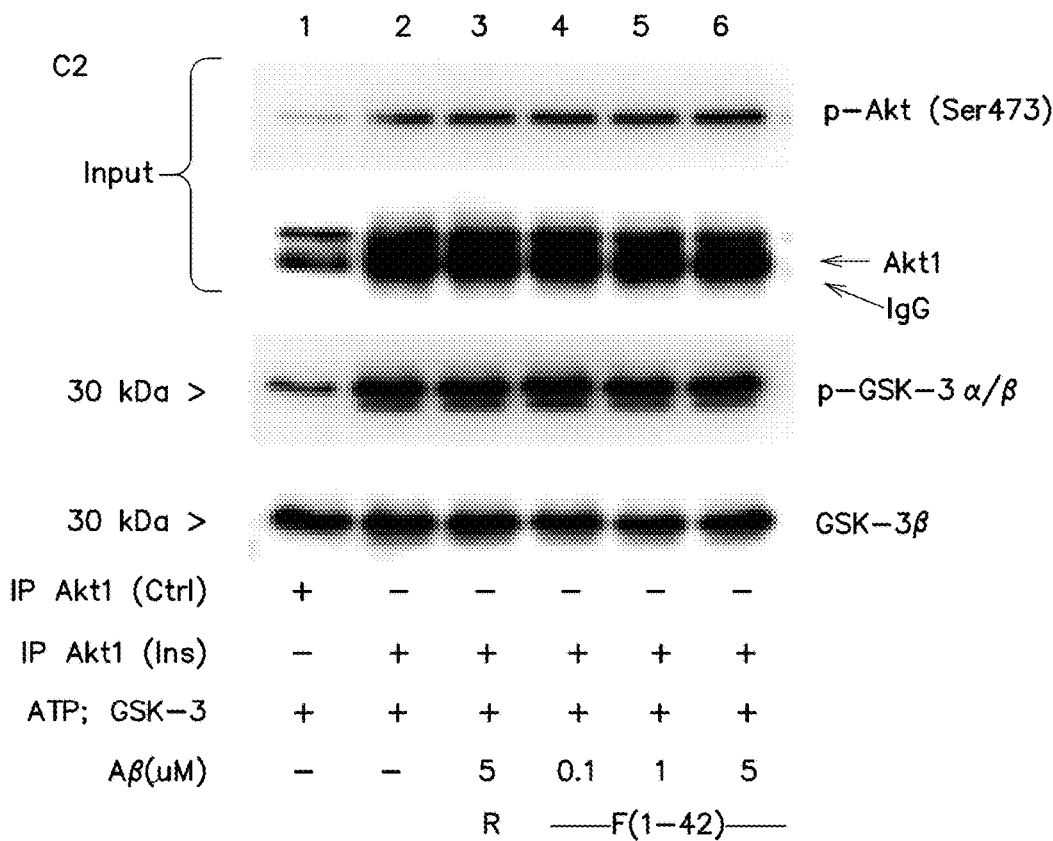
FIGS. 9A-9E illustrate tests for the any inhibition of Akt once activated and the negative effects of extracellular Aβ application
Figure 9A:
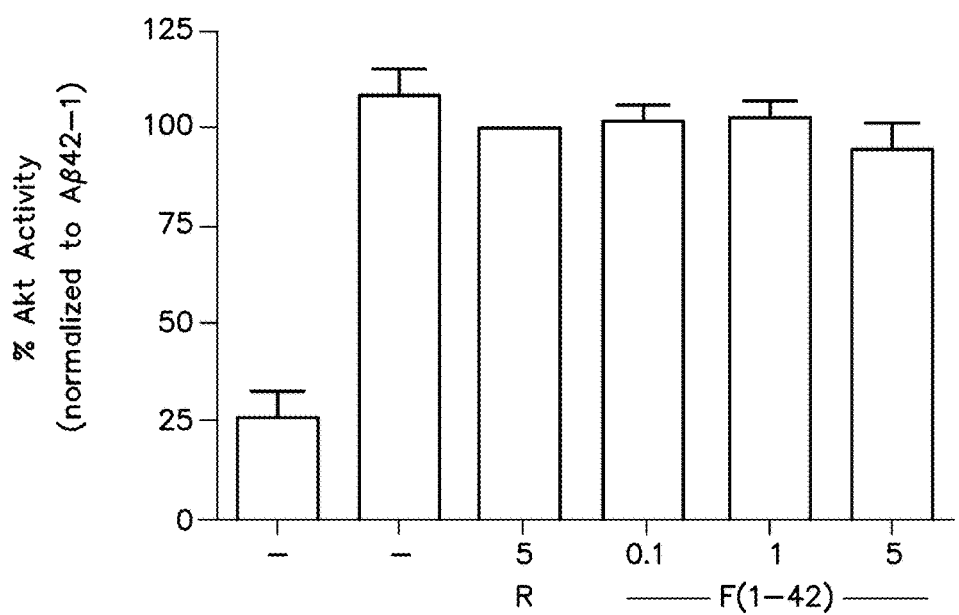

In FIG. 6 in vitro experiments, it was observed that Aβ additions consistently reduced p-Akt levels and activity state. Variably however, the degree of inhibition sometimes exceeded the baseline activity in the absence of PDK. Thus, it is possible that Aβ may have an additional action to deactivate Akt. In order to test if Aβ additionally inhibits Akt phosphorylation and activation by dephosphorylating pre-stimulated Akt (acting as a phosphatase), control and insulin-treated cell extracts were prepared for the immunoprecipitation of pre-activated Akt1. Insulin stimulated Akt activity in extracts made from $C_2C_{12}$myotube cultures (FIG. 9A, $3^{rd}$ row, lane 2 vs. 1). P-Thr308 (not shown) and p-Ser473 Akt levels were also stimulated in step with the enhanced activity to phosphorylate GSK-3 α/β (FIG. 9A, top row lane 2 vs. 1, top row). The lack of effect of Aβ42 on preactivated Akt1 levels and activity was shown in a dose-dependent manner in FIG. 9A, lanes 4-6. As shown for all in vitro experiments, the input of Akt and GSK into the reactions remains constant as per design ($2^{nd}$ or $4^{th}$ row).

Figure 9B:
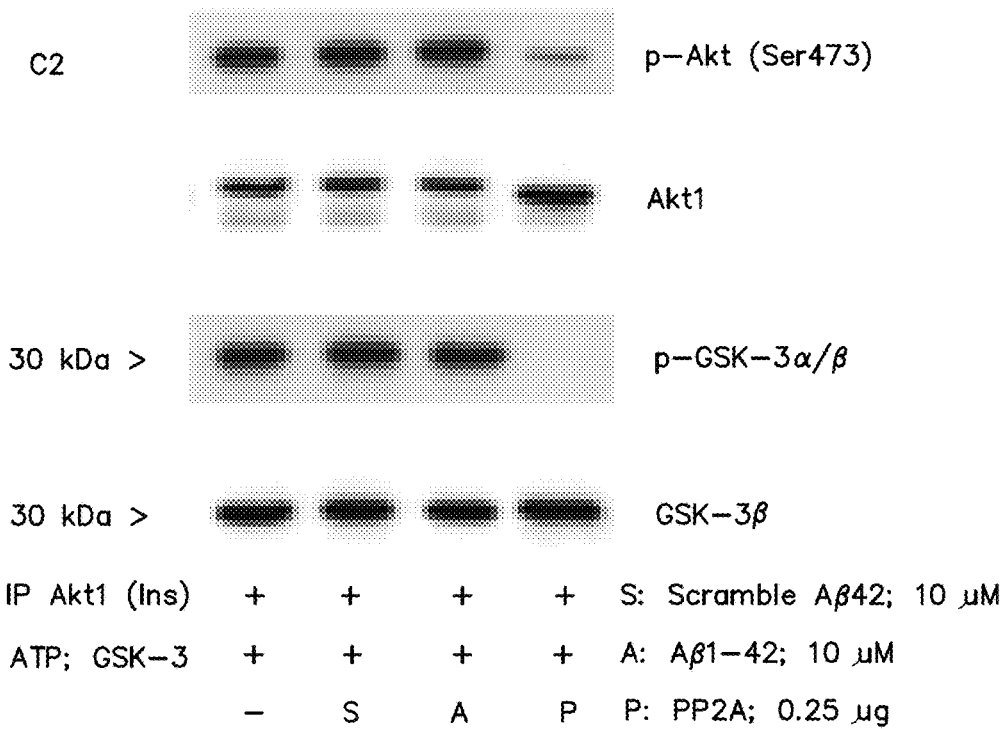
Figure 9B:
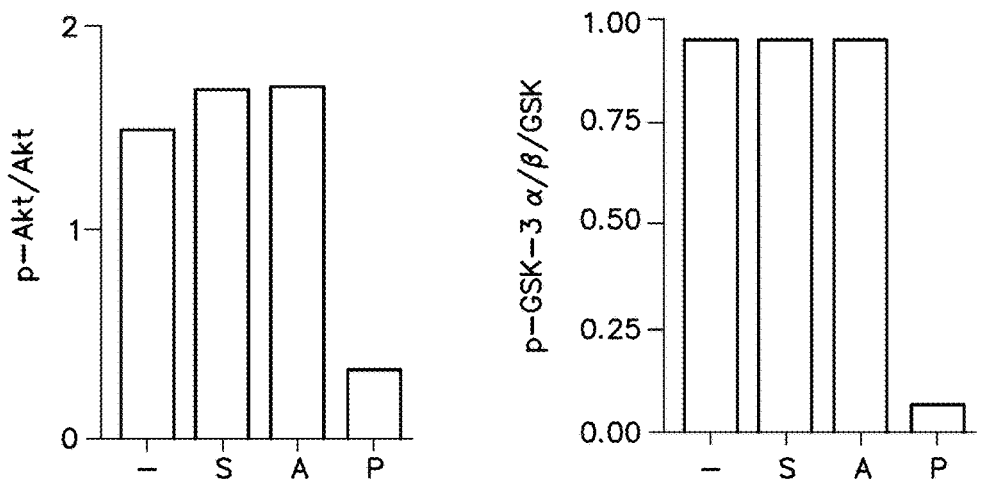

Next in FIG. 9B, the ability of Aβ to inhibit Akt activity or phosphorylation state (once completed through the action of insulin) was directly tested by side-to-side comparison with a known Akt phosphatase, PP2A (Ugi, S., Imamura, T., Maegawa, H., Egawa, K., Yoshizaki, T., Shi, K., Obata, T., Ebina, Y., Kashiwagi, A., and Olefsky, J. M., 2004, Protein phosphatase 2A negatively regulates insulin's metabolic signaling pathway by inhibiting Akt (protein kinase B) activity in 3T3-L1 adipocytes, *Mol Cell Biol* 24:8778-8789). Neither scrambled nor forward Aβ peptide, at modestly high concentration (10 µM), affected Akt p-Ser473 levels or activity (lane 2, 3 vs. 1). PP2A treatment decreased both p-Akt (Ser473) as well as activity levels, as expected (lane 4 and graph below). Thus, Aβ does not have phosphatase action in vitro. This in vitro result was confirmed and the possibility that Aβ could activate a phosphatase in live cells was excluded by maximally pre-stimulating $C_2C_{12}$ cells with insulin before adding doxycycline to induce intracellular Aβ and finding no change in activated p-Akt and activity levels (not shown).

The prior cell-based and in vitro experiments are relevant to intracellular Aβ effects. To determine the specificity of Akt inhibition by intracellular Aβ, $C_2C_{12}$ myotubes were cultured, and treated with extracellular Aβ25-35, Aβ35-25, Aβ1-42 and Aβ42-1 for 24 hours. In the last 30 minutes before harvest, insulin was added (0.1 µg/ml). While p-Akt (Ser473) and p-GSK-3 α/β levels were increased by insulin treatment (FIG. 9C, lane 2 vs. 1), they were not affected by any of the Aβ treatments. Moreover, when the insulin response was measured in detail at varying doses of insulin (20, 100, 500 ng/ml), Aβ concentrations in the media up to 25 µM did not affect p-Akt (Thr308) levels (FIG. 9D). There were also no significant changes in p-Akt (Ser473) levels (data not shown). These experiments suggest that Aβ42 specifically interferes with the action of PDK to phosphorylate Akt. PDK itself is subject to phosphorylation (e.g., at Ser 241) and several authors feel that it is constitutively phosphorylated and thus 'primed' (Casamayor, A., Morrice, N. A., and Alessi, D. R., 1999, Phosphorylation of Ser-241 is essential for the activity of 3-phosphoinositide-dependent protein kinase-1: identification of five sites of phosphorylation in vivo, *Biochem J* 342 (Pt 2):287-292). The experiments described herein indicate that p-PDK levels are constitutively high in $C_2C_{12}$ cells and not boosted further by insulin action (FIG. 9E, top). p-PDK levels were not modulated by extracellular (FIG. 9E lower panel) or intracellular Aβ expression (not shown).

In FIG. 9A Akt1 was immunoprecipitated from control and insulin treated $C_2C_{12}$ myotubes for in vitro kinase assay. Insulin treatment before Akt1 IP and Aβ addition showed the expected increased activity and phosphorylation, but was not inhibited by a range of Aβ42 doses (Lanes 4-6). R=reverse peptide (42-1); F=Aβ 1-42.

In FIG. 9B Aβ42 (10 µM) and scrambled Aβ42 had no effect on insulin-conditioned Akt1 activity. Protein phosphatase 2A (PP2A; 5 µg/ml) decreased levels of both p-Akt (Ser473) and Akt activity (p-GSK-3 α/β), quantified by densitometry below.

Figure 9C:
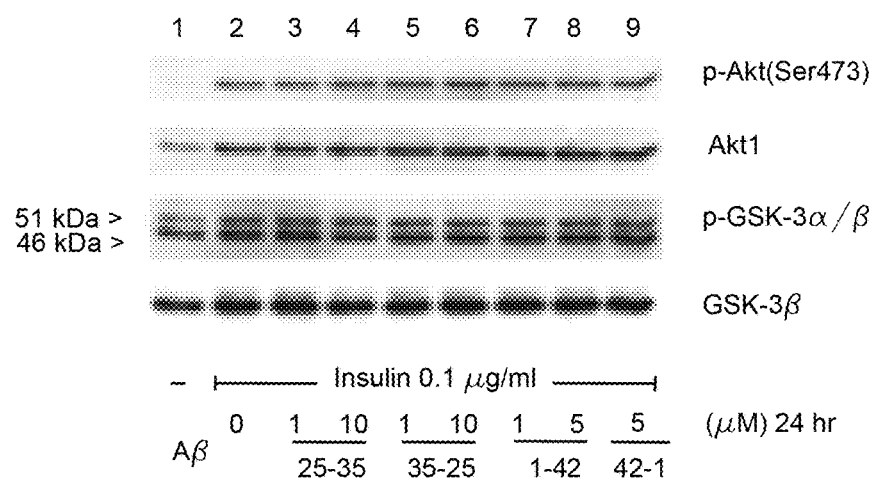
Figure 9D:
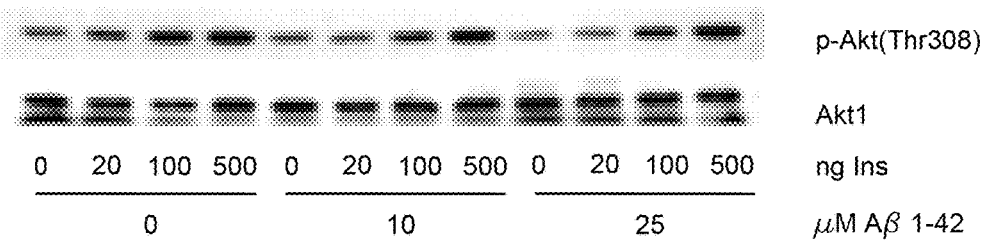

In FIG. 9C $C_2C_{12}$ myotubes were bath exposed to AP25-35, reverse AP35-25, AP1-42 and reverse Aβ42-1 peptides for 24 hours before treatment with insulin (0.1 µg/ml, 15 min) Whole cell extracts were subjected to Western analysis for p-Akt (Ser473) (Akt activation) and total Akt levels (top) as well as for endogenous levels of pGSK-3a/p, indicative of Akt activity, and total GSK-3β (lower two blots). Insulin stimulation significantly increased levels of p-Akt (Ser473) and Akt activity (p-GSK-3 α/β). The increase was not affected by pre-treatment with extracellular AR.

In FIG. 9D $C_2C_{12}$ myotube cultures were exposed to increasing doses of A[i1-42 (0, 10 and 25 µM) for 2 hours before treatment with insulin (0, 20, 100 and 500 ng/ml) for 15 min Harvested cell extracts were used for western blot for p-Akt (Thr308).

Figure 9E:
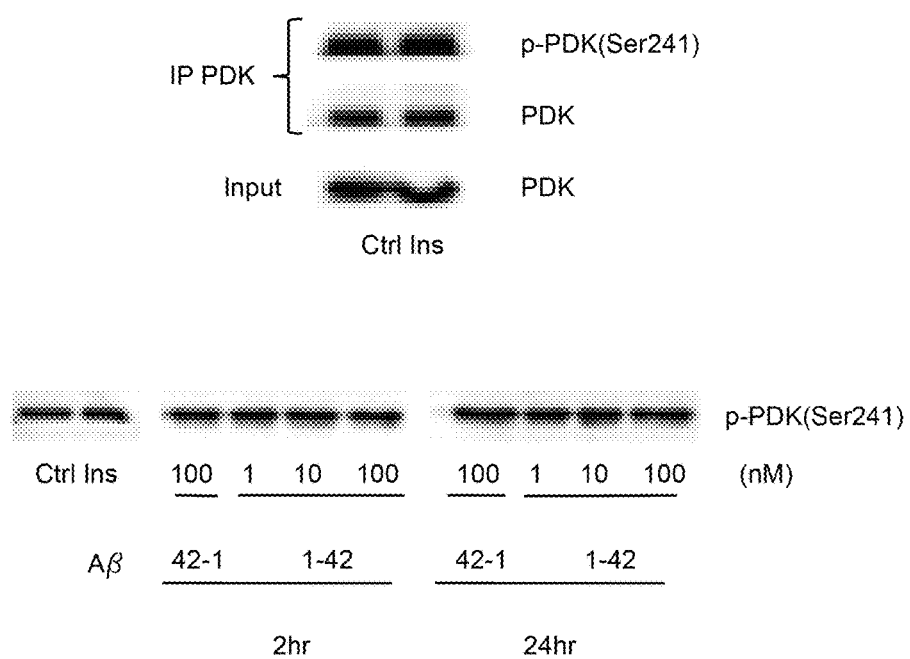

In FIG. 9E insulin treatment did not further increase high resting levels of constitutively phosphorylated PDK (Ser241) in $C_2C_{12}$ myotubes (top and Lanes 1, 2 bottom). $C_2C_{12}$ myotube cultures were treated with insulin (500 ng/ml, 30 min) after either 2 or 24-hour treatments consisting of Aβ42 at from 1-100 nM. p-PDK (Ser241) levels remain unaffected.

Example 8

In vitro PI3K Activity is not Affected by the Addition of Aα

Figure 10A:
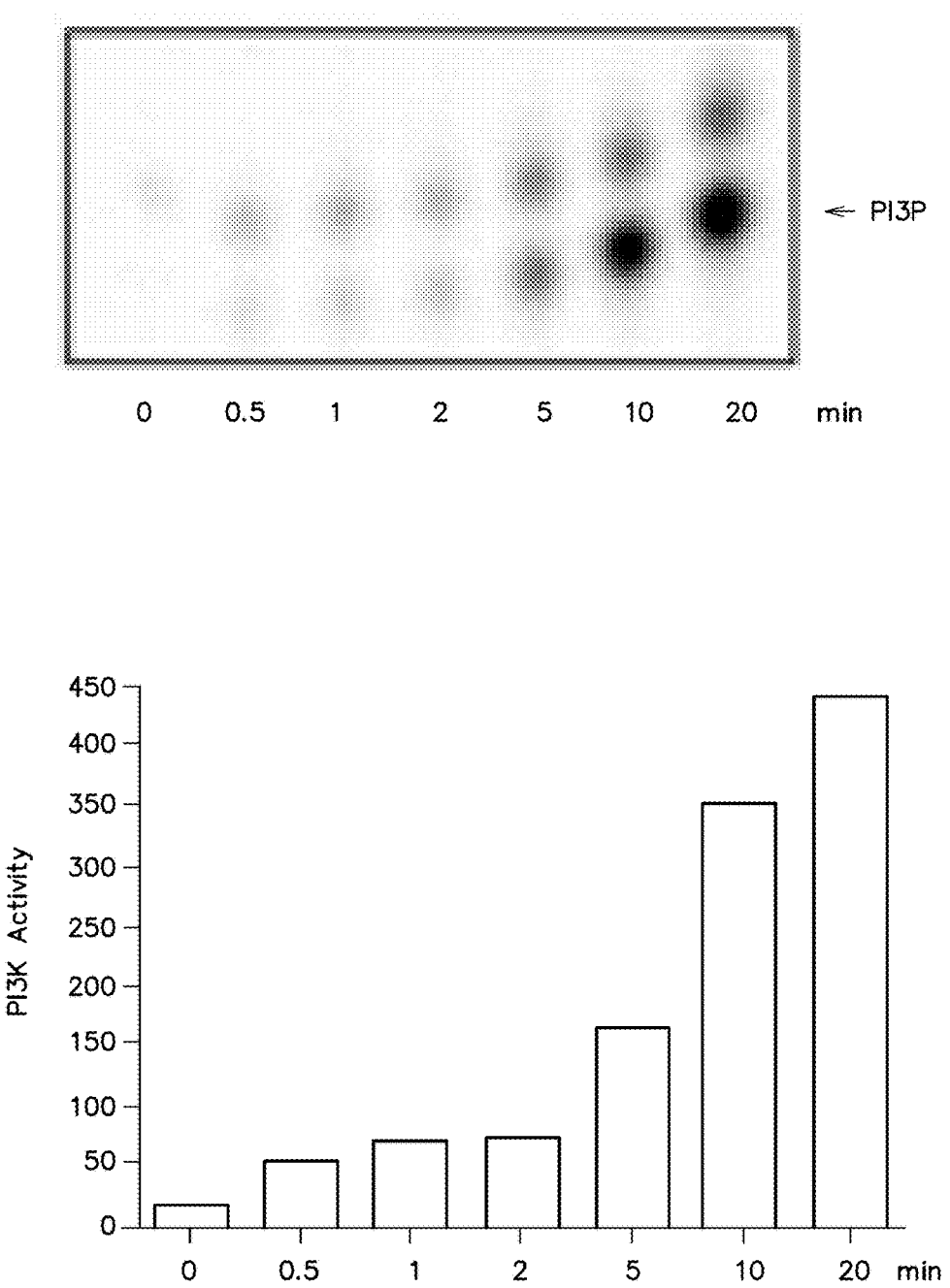
FIGS. 10A-10D show that intracellular Aβ expression does not affect PI3K Activity
Figure 10B:
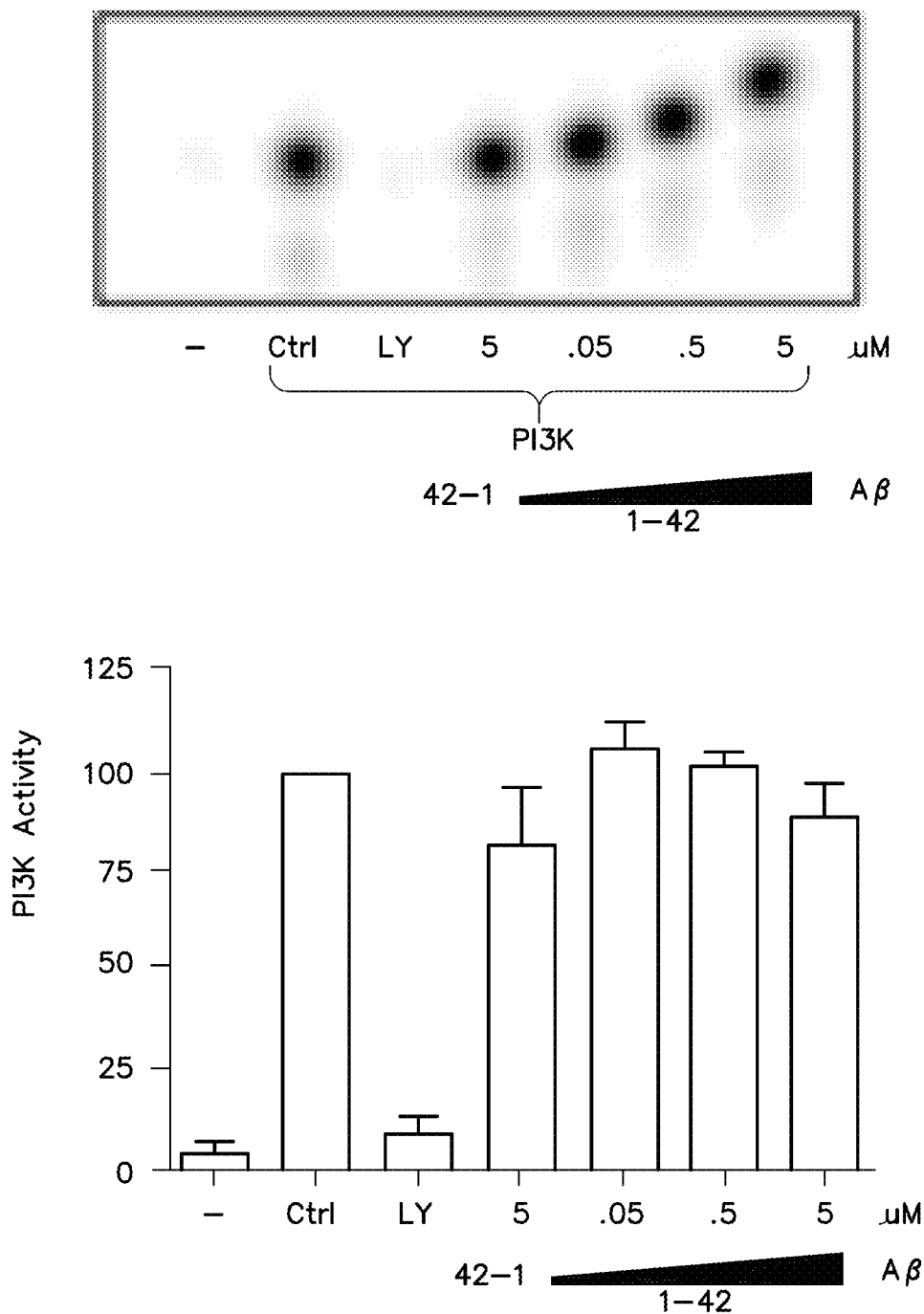
Figure 10C:
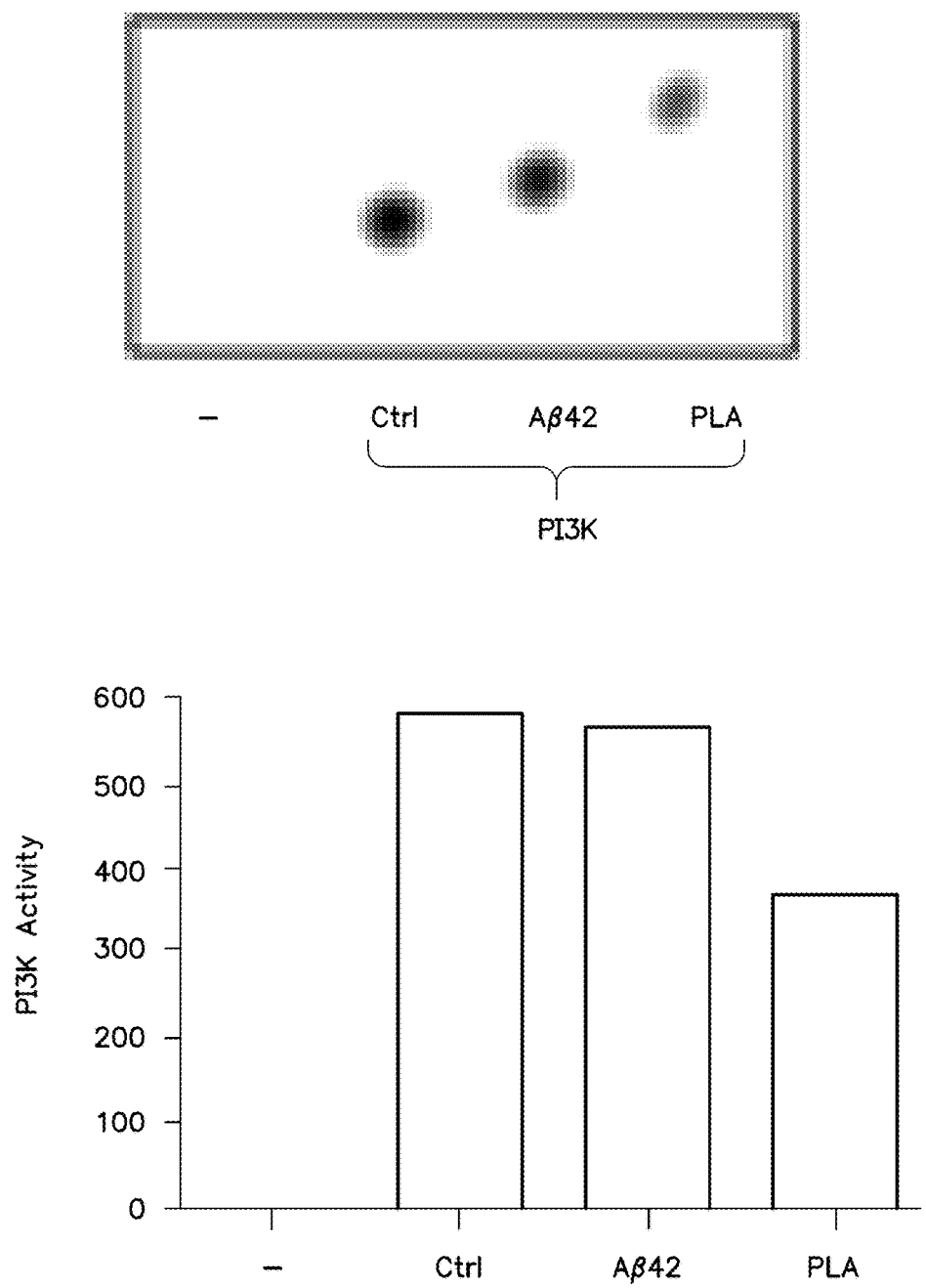
Figure 10D:
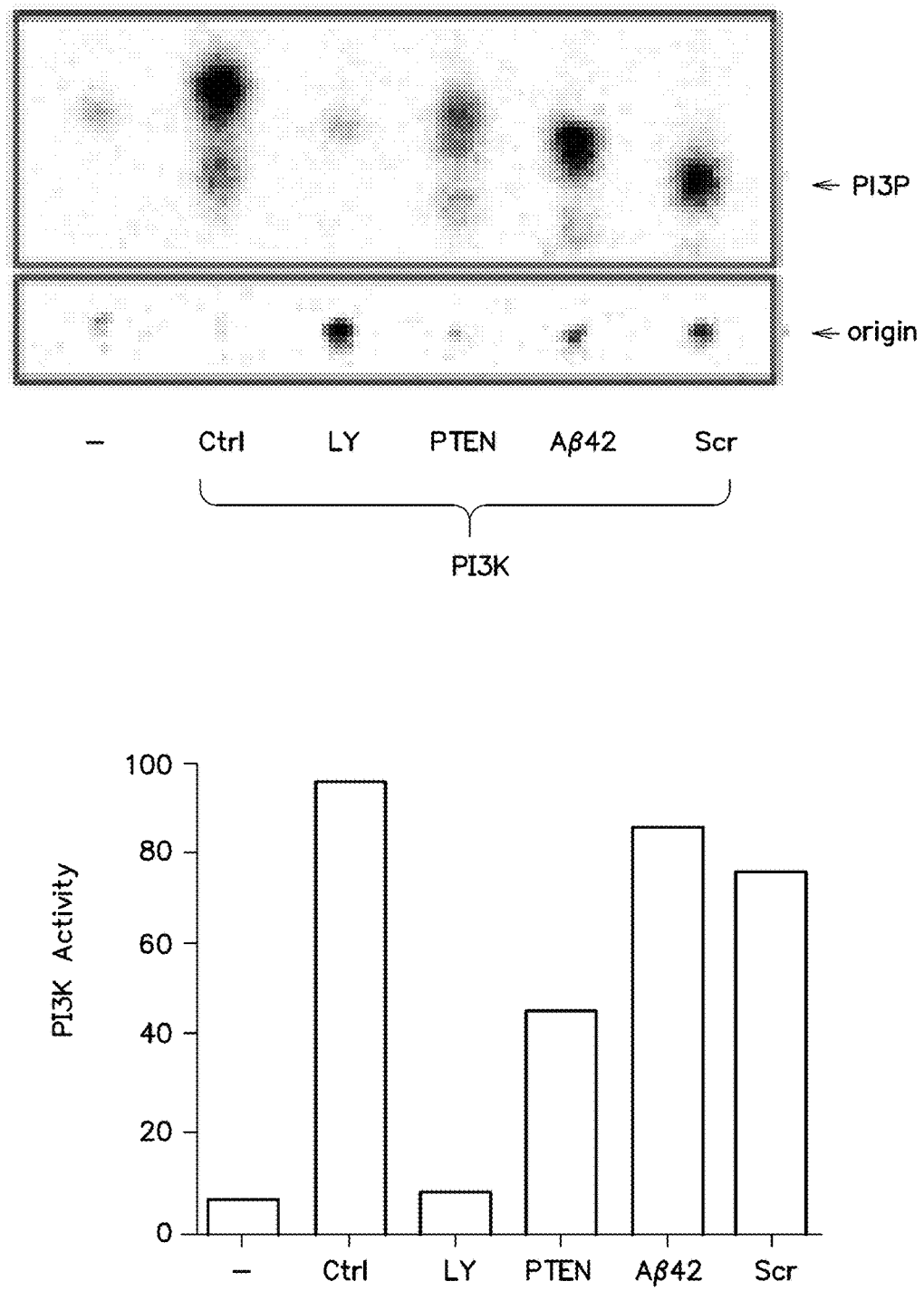

Akt and PDK interactions are hosted by the second messenger lipid PIP3, the product of PI3K (phosphoinositide-3 kinase) activation. Results of FIG. 7C suggest PIP3 concentrations are not limiting. However, it remains possible that Aβ induced interference with Akt activation involves a reduction in the critical availability of this phosphorylated membrane-bound lipid product. To test this, NIH-3T3 cells were grown to confluence and harvested and PI3K activity was obtained by immunoprecipitation onto Sepharose beads. Phosphatidylinositol (PI) was used as substrate in a PI3K activity assay with $^{32}$P-ATP. The products were spotted onto TLC plates. FIG. 10A shows a time-dependent increase in PI3K activity. A 10 minute incubation was chosen for subsequent experiments. Aβ reverse (42-1) and forward (1-42) peptides were tested in a dose-response paradigm in FIG. 10B. As a control, the compound LY294002, a competitive inhibitor of PI3K activity, was tested in the same experiment. Aβ additions had no effect on PI3K activity, whereas LY completely abolished it (FIG. 10B). Addition of phospholipase A2 (PLA2), an enzyme that converts phospholipids (including PIP3) into constituent fatty acids and other lipophilic substances, also showed the expected decrease in levels of PIP3. Aβ42 again had no affect on PI3K activity (FIG. 10C). Finally, Aβ was compared side-by-side with PTEN, a lipid phosphatase, in FIG. 10D. Recombinant PTEN blocked PI3K activity by 50%, whereas Aβ42 (10 µM) and scrambled Aβ (10 µM) did not (FIG. 10D). This indicates that Aβ cannot be interfering with the crucial activation or activity of PI3K to produce PIP3, in its effect to block the stimulation of Akt by insulin.

In FIG. 10A PI3K (p85) was immunopurified from NIH-3T3 cell extracts. Phosphatidylinositol (PI), including phosphatidylserine (PS) as a carrier, was used as a substrate for PI3K activity assay. [γ-32P]ATP and kinase buffer were added to the IP and lipid mixture at room temperature to start the reaction. Phospholipids were extracted in 100 µl of $CHCl_3$/methanol and separated by TLC. Bar charts give quantified results using a phosphorimager. The indicated spot identifies the PI3P product shown accumulating over the times indicated.

In FIG. 10B PI3K assay was performed in the presence of the specific inhibitor compound LY294002 (LY, 100 µM), reverse Aβ42-1 (5 µM), or increasing doses of Aβ1-42 (0.05 0.5, 5 µM).

In FIG. 10C Phospholipase A2 (500 µg/ml) or reverse Aβ42-1 (10 µM) were added just prior to extraction in $CHCl_3$/methanol.

In FIG. 10D the PI3K activity assay was performed in the presence of PTEN (10.6 µg/ml) or Aβ42 (10 µM). The PTEN phosphatase inhibited PI3K activity by approximately 50%, while Aβ42 (10 µM) had no effect. Scrambled peptide (Scr; 10 µM) served as a control. These experiments demonstrate that Aβ acts neither as a direct inhibitor of PI3K nor as a phosphatase to reverse insulin signaling.

Example 9

Akt-Dependent Substrate Phosphorylation

Assays for determining the level of Aβ inhibition of the activation of Akt, and/or the extent to which a candidate compound reduces the level of Aβ inhibition, may include techniques for determining levels of substrate phosphorylation. Non-limiting examples of techniques for determining levels of substrate phosphorylation are described herein.

9A) Colorimetric detection of Akt activity: Streptavidin coated 96 (or 384) well plates are preincubated with synthetic biotinylated Akt substrate peptide (GRPRTSSFAEG-biotin; Calbiochem; also referred to a paramyosin Crosstide) and the plates blocked with Pierce blocking buffer. A master mix consisting of immunoprecipitated Akt and PDK prepared from SH-SY5Y or $C_2C_{12}$ cells, lipid mixture (PIP3, phosphatidylserine and phosphatidylcholine), ATP, kinase buffer and 5 µM synthetic Aβ is delivered to each well and incubated in the presence of the compound library (total volume=50 µl). One set of wells on each plate is left without Aβ or small molecule compounds in order to measure the maximal, native signal capacity of the assay. The plates are incubated for 30 minutes at 30° C. with mixing. The reactions are stopped by the addition of kinase stop solution (Calbiochem), and the plates are washed 3 times and excess liquid is removed. Monoclonal anti-phosphoserine antibody is added and the plates incubated for 1 h at room temperature. The plates are washed and then incubated with HRP-conjugated goat anti-mouse secondary antibody. After a final washing step, incubation proceeds for 30 minutes in the dark in the presence of tetramethylbenzidine liquid substrate (TMB; Sigma). The absorbance is read at 450 nm, with a subtracted reference wavelength set at 540-595 nm.

9B) Europium based time resolved fluorometry detection of Akt activity: As a non-limiting alternative to the assay described in 9A, lanthanide-chelate labels may be used in time-resolved fluorometry. Because of the long decay time and large Stokes shift of lanthanide chelates, interference caused by background fluorescence can essentially be eliminated. As described in 9A, plates are generated that are precoated with Akt substrate peptide and processed as above. After the monoclonal anti-phosphoserine incubation and washing steps, plates are incubated in the presence of Europium labeled rabbit anti-mouse IgG (PerkinElmer). Enhancement solution is added to free the europium label into a highly fluorescent micelle and fluorescence is measured by excitation at 340 nm and emission at 620 nm.

9C) Superquenching based fluorometry detection of Akt activity: Another non-limiting alternative to the techniques described in 9A and 9B is the use of the QTL Lightspeed system for detection (BD Biosciences). Assays are prepared as described above. However; the detection phase is unique and highly sensitive. After Akt activity is induced with ATP and lipids, the samples are washed, and the wells are incubated with the 'QTL Sensor'. The latter consists of microspheres, embedded with a conjugated fluorescent polymer and a phosphate coordinating metal ion. The intrinsically fluorescent sensing spheres interact with the phosphoserine residues formed on the substrate peptide which has an attached quenching moiety. The result is inhibition (or superquench) of the native fluorescence of the polymers by the Akt phosphorylated substrate-quencher conjugate. The drop in fluorescence is directly proportional to the activity of Akt on the substrate peptide. Aβ42 is expected to inhibit superquenching. According to the invention, a candidate compound of interest may be identified as one that maintains superquenching in the presence of an Aβ polypeptide.

Accordingly, in any of the different assay configurations specifically described herein or in any other substrate-based assays for determining levels of Akt activity, one or more candidate compounds may be identified as compounds that prevent or neutralize the reduction of Akt activity in the presence of Aβ.

According to aspects of the invention, candidate compounds can be further evaluated to determine whether they specifically reduce or neutralize the negative effect of Aβ on the association between Akt and PDK-1 (e.g., as opposed to non-specifically increasing Akt activity or substrate phosphorylation).

Example 10

Direct Detection of Akt-PDK Interactions

Assays for determining the level of Aβ inhibition of the activation of Akt, and/or the extent to which a candidate compound reduces the level of Aβ inhibition, may include techniques for directly detecting levels of Akt-PDK interactions (e.g., levels of Akt associated with PDK or levels of PDK-dependent Akt phosphorylation). Non-limiting examples of techniques for determining levels of Akt-PDK interactions are described herein.

10A) Colorimetric detection of Akt-PDK1 interaction: In these assays, multiwell plates are precoated with goat anti-total-Akt and then blocked as described for the assays in Example 9 above. Cell extracts are prepared from SH-SY5Y cells or $C_2C_{12}$ myotubes that have been either: 1) infected with Ad-wtAkt (m.o.i. 25-50) or 2) transfected with pcDNA3.1-mycPDK1 plasmid (1-3 µg/ml). These systems have been used successfully to increase the available amount of these wild type proteins from a modest number of cells. Multiwell plates are loaded with both extracts, Aβ and a chemical library of compounds are added for 30 minutes at 30° C. with mixing. Following this reaction, the wells are washed and incubated with monoclonal mouse anti-PDK1. After incubation for 1 hour at room temperature the wells are washed and then incubated with the secondary HRP-conjugated antibody for 30 minutes. Following final washes, the plates are incubated with TMB substrate solution and allowed to develop for 30 minutes at room temperature in the dark and the absorbance read as described above. A compound that increases the ability of Akt and PDK1 to interact in the presence of added Aβ will increase the level of sample absorbance.

10B) Colorimetric ELISA-type detection of direct Akt activation (phosphorylation) by PDK1: In this assay the ability of PDK1 to interact with Akt and phosphorylate it will be measured directly. In some embodiments, phospho-site specific antibodies for Akt pSer473 and pThr308 show a very high degree of detection fidelity. Multiwell plates are precoated with capture antibody goat anti-total Akt as in 10A. After blocking, Akt is bound by incubating the wells for 2 hours at room temperature with cell extract from Adv-wtAkt overexpression. Following a wash, the master mix, which contains synthetic Aβ, immunoprecipitated PDK1, lipid mixture, ATP and kinase buffer is added to all wells plus the test compounds. The plates are incubated for 30 minutes at 30° C. with mixing. After the wells are washed there follows an incubation with rabbit anti-pAkt (Ser473 and Thr308; Cell Signal) for 1 hour at room temperature. Following washing, the plates are incubated with goat anti-rabbit-HRP conjugated antibody for 1 hour at room temperature and developed using TMB as described above. Any compound that is capable of either increasing PDK1 activity directly or inhibiting the negative effects of Aβ will be identified by an increase in detectable pAkt.

According to aspects of the invention, candidate compounds can be further evaluated to determine whether they specifically reduce or neutralize the negative effect of Aβ on the association between Akt and PDK-1 (e.g., as opposed to non-specifically increasing Akt activity or substrate phosphorylation).

Example 11

Cell-Based Assay for Maintaining Akt Signaling

Assays for determining the level of Aβ inhibition of the activation of Akt, and/or the extent to which a candidate compound reduces the level of Aβ inhibition, may include cell-based techniques for determining the level of Akt signaling in the presence of intracellular Aβ. In some embodiments, test compounds are evaluated for their ability to restore Akt activation in cells expressing intracellular Aβ. Non-limiting examples of cell-based techniques are described herein.

11A) Colorimetric detection of cell permeant compound antagonism of Aβ: About $1.5 \times 10^5$ SH-SY5Y human neuroblastoma cells or mouse $C_2C_{12}$ myotubes can be grown per well in a multi-well format (e.g., in either a 96 or 384 well format. Cultures are infected with the doxycycline inducible Ad-TRE-Aβ and amyloid expression is induced by the addition of doxycycline at 1 µg/ml for 24 hours. Test compounds are added to the cultures 12 hours after β-amyloid induction. This will eliminate untoward effects of the compounds on viral transcription or RNA stability. The inducer will be maintained for the entire time. Cells are lysed in situ in lysis buffer containing deoxycholate and NP-40 and the plates are centrifuged for 10 minutes at 10,000×g to pellet insoluble material. Extract aliquots are transferred by low speed spin to a total Akt antibody coated plate and incubated for either 2 h at room temperature or overnight at 4° C. Activation of Akt will be assayed directly by measuring site-specific phosphorylation as described above in assay 10B. Washing, processing and detection will be the same as described. This assay will identify compounds that are not only able to alter the effects of Aβ when processed in vivo by the living cell (non-synthetic Aβ), but may also identify those that can freely traverse the intact membrane. An alternative method will be to transfer the lysate to a plate designed for an Akt activity determination, as in 9B or C.

According to aspects of the invention, candidate compounds can be further evaluated to determine whether they specifically reduce or neutralize the negative effect of Aβ on the association between Akt and PDK-1 (e.g., as opposed to non-specifically increasing Akt activity or substrate phosphorylation).

Incorporation by Reference

All of the scientific and patent publications referred to herein and in the attachment are incorporated herein by reference in their entirety. In the event of conflicting disclosures, the present detailed description is controlling.

Those skilled in the art will recognize, or be able to ascertain using no more than routine experimentation, many equivalents to the specific embodiments of the invention described herein. Such equivalents are intended to be encompassed by the following claims.

I claim:

1. A method for detecting Akt (protein kinase B, PKB) activation in a cell, comprising
expressing a heterologous Aβ42 polypeptide in a cell in vitro using recombinant cDNA or by viral vector,
lysing the cell to produce an Akt containing lysate, and
determining whether Akt is activated by ELISA or Western blot by detecting whether or not Akt is phosphorylated (on serine 473 or threonine 308), wherein the lysate is fractionated using gel electrophoresis and phosphorylated forms of Akt are directly identified by Western blot or Akt is immobilized onto a solid support and activation is determined using antibodies by ELISA or Akt is immunoprecipitated onto beads in solution from the lysates prepared from the cells and then subjected to Western blot.

2. The method of claim 1, wherein the cell is treated with insulin or insulin-like growth factor (IGF-1) to stimulate Akt activation relative to a cell according to claim 1 that is not treated with insulin or IGF-1.

3. The method of claim 1, further comprising measuring enzyme activity level of Akt in response to a test compound in the Akt containing cellular lysate by determining a level of substrate phosphorylation, comprising
adding the test compound and an Akt substrate to the cell culture expressing Aβ42 polypeptide,
determining a level of Akt substrate phosphorylation by Western or ELISA,
determining whether the test compound has increased Akt activity relative to the absence of the test compound.

4. The method of claim 3, further comprising identifying the test compound as a candidate compound for treating Alzheimer's disease if the test compound reduces Aβ-mediated inhibition of Akt activity or activation state relative to the absence of the test compound.

5. The method of claim 1, wherein the cell is a neuronal cell or a muscle cell.

6. The method of claim 3, further comprising comparing the increased activity level of Akt in the presence of the test compound with a control (baseline) Akt activity level, wherein the control (baseline) Akt activity level is an Akt activation level measured in a heterologous Aβ42 polypeptide expressing cell that has been treated with insulin.

* * * * *